United States Patent
Roessler et al.

(10) Patent No.: US 10,233,470 B2
(45) Date of Patent: Mar. 19, 2019

(54) SECRETION OF FATTY ACIDS BY PHOTOSYNTHETIC MICROORGANISMS

(75) Inventors: Paul Gordon Roessler, San Diego, CA (US); You Chen, San Diego, CA (US); Bo Liu, San Diego, CA (US); Corey Neal Dodge, Cardiff, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 13/340,350

(22) Filed: Dec. 29, 2011

(65) Prior Publication Data

US 2013/0005003 A1 Jan. 3, 2013

Related U.S. Application Data

(62) Division of application No. 12/333,280, filed on Dec. 11, 2008.

(60) Provisional application No. 61/007,333, filed on Dec. 11, 2007.

(51) Int. Cl.
C12P 7/64 (2006.01)
C12N 9/16 (2006.01)

(52) U.S. Cl.
CPC .......... *C12P 7/649* (2013.01); *C12N 9/16* (2013.01); *C12P 7/6409* (2013.01); *Y02E 50/13* (2013.01); *Y02P 20/582* (2015.11); *Y02T 50/678* (2013.01)

(58) Field of Classification Search
USPC .............. 435/196, 243, 257.2, 440, 134
See application file for complete search history.

(56) References Cited

U.S. PATENT DOCUMENTS

| | | | | |
|---|---|---|---|---|
| 5,179,219 A | * | 1/1993 | Priegnitz | 554/193 |
| 5,298,421 A | | 3/1994 | Davies et al. | |
| 6,150,512 A | | 11/2000 | Yuan | |
| 6,495,140 B1 | * | 12/2002 | Collins et al. | 424/745 |
| 6,699,696 B2 | | 3/2004 | Woods et al. | |
| 2004/0111763 A1 | * | 6/2004 | Heinz et al. | 800/281 |
| 2004/0197882 A1 | * | 10/2004 | Saitoh et al. | 435/166 |
| 2005/0191679 A1 | * | 9/2005 | Metz et al. | 435/6 |
| 2006/0117414 A1 | | 6/2006 | MaCool et al. | |
| 2007/0087420 A1 | | 4/2007 | Qiu | |
| 2008/0182308 A1 | * | 7/2008 | Donaldson et al. | 435/160 |
| 2009/0298143 A1 | | 12/2009 | Roessler et al. | |

FOREIGN PATENT DOCUMENTS

| | | |
|---|---|---|
| EP | 1752532 A1 | 2/2007 |
| EP | 08860168.7 | 9/2010 |
| JP | Hei 08-168389 A | 7/1996 |
| WO | WO 1994/010288 | 5/1994 |
| WO | WO 2007/136762 | * 11/2007 |
| WO | WO 2007/136762 A2 | 11/2007 |
| WO | WO 2008/119082 | 10/2008 |
| WO | WO 2008/151149 | 12/2008 |
| WO | WO 2010/033921 | 3/2010 |

OTHER PUBLICATIONS

Pierce et al., Photosynthesis Research 16:141-154, 1988.*
Starai et al., Cell Mol Life Sci 61(16):2020-2030, 2004.*
Cho et al., J. Biol. Chem. 270(9):4216-4219, 1995.*
Koo et al., The Plant Journal 44:620-632, 2005.*
Zhou et al., Cell Mol Life Sci 63(19-20):2260-2290, 2006.*
Kozak, M., Gene 234:187-208, 1999.*
Lem et al., Plant Physiology 74:134-138, 1984.*
Goldman et al., Biotechnology and Bioengineering 24:619-631, 1982.*
Rippka et al., Journal of General Microbiology 111:1-61, 1979.*
Branch, TIBS 23:45-50, 1998.*
Yoo et al., Carbohydrate Research 337:2195-2203, 2002.*
Bhattacharyya et al., Cell 60:115-122, 1990.*
Webster's Ninth New Collegiate Dictionary, p. 1176, 1985.*
Anspach et al., Journal of Chromatography 865:129-144, 1999.*
Markov et al., Enzyme and Microbial Technology 17:306-310, 1995.*
Welker et al., FEMS Microbiology Reviews 30(4):530-563, 2006.*
Alamsjah et al., "Algicidal activity of polyunsaturated fatty acids derived from Ulva fasciata and U. pertusa (Ulvaceae, Chlorophyta) on phytoplankton" (2008) *J. Appl Phycol* 20:713-720.
Chiang et al., "Allelochemicals of Botryococcus braunii (Chlorophyceae)" (2004), *J. Phycol.* 40:474-480.
Collier et al., "A small polypeptide . . . in nutrient-deprived cyanobacteria", (1994) *EMBO J.* 13:1039-1047.
Furhman et al., "The abundant retinal protein . . . and photophobic responses", (2001), *J. Cell Sci.* 114:3857-3863.
Gumpel et al., "Studies on homologous recombination in the green alga *Chlamydomonas reinhardtii*", (1994), *Curr. Genet.* 26:438-442.
Ikawa et al., "Inhibition of Chlorella growth by degradation and related products of . . . polyunsaturated fatty acids in phytoplankton ecology", (1997) *Hydrobiologia* 356:143-148.
Matsuoka et al., "Gene replacement in cyanobacteria mediated by a dominant streptomycin-sensitive rps12 gene . . . drug resistance markers", (2001) *Microbiol.* 147:2077-2087.
Shroda et al., "RNA silencing in Chlamydomonas: mechanisms and tools", (2006), *Curr. Genet.* 49:69-84.
Sodeinde et al., "Homologous recombination in the nuclear genome of *Chlamydomonas reinhardtii*", (1993), *Proc. Natl. Acad. Aci.* 90:9199-9203.
Wu et al., "Cytotoxic effects of free fatty acids on phytoplankton algae and cyanobacteria", (2006), *Aquatic Toxicology* 80:338-345.
Binderup et al., "Limited proteolysis of branching enzyme from *Escherichia coli*", *Arch. Biochem. Biophys.*, 377(2):366-71 (2000).
Branden et al., Introduction to Protein Structure, *Garland Publishing Inc.*, New York, p. 247 (1991).

(Continued)

*Primary Examiner* — Delia M Ramirez
(74) *Attorney, Agent, or Firm* — DLA Piper LLP (US)

(57) ABSTRACT

Recombinant photosynthetic microorganisms that convert inorganic carbon to secreted fatty acids are described. Methods to recover the secreted fatty acids from the culture medium without the need for cell harvesting are also described.

21 Claims, 6 Drawing Sheets

Specification includes a Sequence Listing.

(56) References Cited

OTHER PUBLICATIONS

Chisti, "Biodiesel from microalgae beats bioethanol", *Trends in Biotechnology*, 26:126-131 (2008).
Chisti, "Biodiesel from microalgae", *Biotechnology Advances*, 25:294-309 (2007).
Dehesh et al., "Production of High levels of 8:0 and 10:0 fatty acids in transgenic canola by overexpression of Ch FatB2, a thioesterase cDNA from Cuphea hookeriana", *The Plant Journal*, 9(2):167-172 (1996).
Dehesh et al., "Production of high levels of 8:0 and 10:0 fatty acids in transgenic canola by overexpression of Ch FatB2, a thioesterase cDNA from Cuphea hookeriana", *The Plant Journal*, 9:167-172 (1996).
Dehesh et al., "Two novel thioesterases are key determinants of the bimodal distribution of acyl chain length of Cuphea palustris seed oil", *Plant Physiology*, 110:203-210 (1996).
Dillon et al, "The Hotdog fold: wrapping up a superfamily of thioesterases and dehydratases", *BMC Bioinformatics*, 5:109, 2004.
Fischer et al., "Selection and optimization of microbial hosts for biofuels production", *Metabolic Engineering*, 10:295-304 (2008).
Greenwell et al., "Placing microalgae on the biofuels priority list: a review of the technological challenges", *J. R. Soc. Interface*, 7:703-726 (2010).
Grima et al., "Recovery of microalgal biomass and metabolites: process options and economics", *Biotechnology Advances*, 20:491-515 (2003).
Guo et al., "Protein tolerance to random amino acid change", *PNAS*, 101(25):9205-9210 (2004).
Hitz et al., "Cloning of a Higher-Plant Plastid w-6 Fatty Acid Desaturase cDNA and Its Expression in a Cyanobacterium", *Plant Physiol.*, 105:635-641 (1994).
Hu et al., "Microalgal triacylglycerols as feedstocks for biofuel production: perspectives and advances", *The Plant Journal*, 54:621-639 (2008).
Ladygina et al., "A review on microbial synthesis of hydrocarbons", *Process Biochemistry*, 41:1001-1014 (2006).
Li et al., "Perspectives of microbial oils for biodiesel production", *Appl. Microbiotechnol. Biotechnol.*, 80:749-756 (2008).
Lo et al., "Substrate Specificities of *E. coli* Thioesterase I/Proteasel/Lysophospholipase L1 are Governed by Its Switch Loop Movement", *Biochemistry*, 44:1971-1979 (2005).
Lu et al., "Overproduction of free fatty acids in *E. coli*: Implications for biodiesel production", *Metabolic Engineering*, 10:333-339 (2008).
Lykidis, "Genomic Prospecting for Microbial Biodiesel Production", *Lawrence Berkeley National Laboratory: Lawrence Berkeley National*, 2008. Laboratory,(scholarship.org/uchtem/04h4d5dp).
Mayer et al., "A Structural Model of the Plant Acyl-Acyl Carrier Protein . . . ", *J. Biol. Chemistry*, 280(5):3621-3627 (2005).
Mayer et al., "Identification of amino acid residues involved in substrate specificity of plant acyl-ACP thioesterases using a bioinformatics-guided approach", *BMC Plant Biology*, 7:1 (2007).
Ng et al., "SIFT: predicting amino acid changes that affect protein function", *Nucleic Acids Research*, 31(13):3812-3814 (2003).
Pienkos et al., "The promise and challenges of microalgal-derived biofuels", *Biofuels Bioproducts & Biorefining*, 3:431-440 (2009).
Radakovits et al., "Genetic Engineering of Algae for Enhanced Biofuel Production", *Eukaryotic Cell*, 9(4):486-501 (2010).
Seffernick et al., "Melamine deaminase and atrazine chlorohydrolase: 98 percent identical but functionally different", *J. Bacteriol.*, 183(8):2405-2410 (2001).
Sheridan, Nature America, Inc., *Nature Biotechnology*, 27(12):1075-1076 (2009).
Stal et al., "Fermentation in cyanobacteria", *FEMS Microbiology Reviews*, 21:179-211, (1997).
Stephens et al., "Future prospects of microalgal biofuel production systems", *Trends in Plant Science*, 15:1360-1385 (2010).
Synthetic Genomics, Inc., European Search Report, PCT/US2008/086485, dated Jan. 4, 2011.

Voelker and Davies, "Alteration of the specificity and regulation of fatty acid synthesis of *Escherichia coli* by expression of a plant medium-chain acyl-acyl carrier protein thioesterase", *Journal of Bacteriology*, 176:7320-7327 (1994).
Voelker et al., "Plant Acyl-Acp Thioesterases: Chain-Length Determining Enzymes in Plant Fatty Acid Biosynthesis", *Genetic Engineering*, 18:111-133 (1996).
Voelker et al., "Fatty acid biosynthesis redirected to medium chains in transgenic oilseed plants", *Science*, 257:72-74 (1992).
Witkowski et al., "Conversion of a beta-ketoacyl synthase to a malonyl decarboxylase by replacement of the active-site cysteine with glutamine", *Biochemistry*, 38:11643-11650 (1999).
Angelidaki and Ahring, "Effects of free long-chain fatty acids on thermophilic anaerobic digestion", *Appl. Microbiol. Biotechnol.*, 37:808-812 (1992).
Barclay et al., "Heterotrophic production of long chain omega-3 fatty acids utilizing algae and algae-like microorganisms", *J. Appl. Phycology*, 6:123-129 (1994).
Chen and Johns, "Effect of C/N ratio and aeration on the fatty acid composition of heterotrophic Chlorella sorokiniana", *J. Appl. Phycol.*, 3:203-209 (1991).
Chen and Johns, "A strategy for high cell density culture of heterotrophic microalgae with inhibitory substrates", *J. Appl. Phycology*, 7:43-46 (1995).
Chen and Zhang, "High Cell Density Mixotrophic culture of Spirulina plantensis on glucose for phycocyanin production using a fed-batch system", Enzyme and Microbial Technology, 20:221-224 (1997).
Desai and Banat, "Microbial Production of Surfactants and Their Commercial Potential", Microbiology and Molecular Biology Reviews, 61(1):47-64 (1997).
Graverholt and Eriksen, "Heterotrophic high-cell-density fed-batch and continuous-flow cultures of Galdieria sulphuraria and production of phycocyanin", *Appl. Microbiol. Biotechnol.*, 77(1):69-75 (2007). Epub.: Sep. 5, 2007.
Hai et al., (2001) "Multiple evidence for widespread and general occurrence of type-III PHA synthases in cyanobacteria and molecular characterization of the PHA synthases from two thermophilic cyanobacteria: Chlorogloeopsis fritschii PCC 6912 and *Synechococcus* sp. strain MA19", Microbiology, 147(Pt 11):3047-3060 (2001).
Hoiczyk and Hansel, "Cyanobacterial Cell Walls: News from an Unusual Prokaryotic Envelope", *J. Bacteriol.*, 182(5):1191-1199 (2000).
Jones et al., "Palmitoyl-acyl carrier protein (ACP) thioesterase and the evolutionary origin of plant acyl-ACP thioesterases", The Plant Cell, 7(3):359-371 (1995).
Lee, "Microalgal mass culture systems and methods: Their limitation and potential", J. Applied Phycology, 13(4):307-315 (2001).
Lem et al., "In Vitro Fatty Acid Synthesis and Complex Lipid Metabolism in the Cyanobacterium, Anabaena Variabilis: II. Acyl Transfer and Complex Lipid Formation", Plant Physiol., 75(3):700-704 (1984).
Margalith P.Z., "Production of ketocarotenoids by microalgae", *Appl. Microbiol. Biotechnol.*, 51(4):431-438 (1999).
Martinez and Orús, "Interactions between Glucose and Inorganic Carbon Metabolism in Chlorella Vulgaris Strain UAM 101", Plant Physiol., 95(4):1150-1155 (1991).
Mukherjee et al., "Towards commercial production of microbial surfactants", Trends Biotechnol., 24(11):509-515 (2006). Epub.: Sep. 25, 2006.
Nishida and Murata, "Chilling Sensitivity in Plants and Cyanobacteria: The Crucial Contribution of Membrane Lipids", Annu. Rev. Plant Physiol. Plant Mol. Biol., 47:541-568 (1996).
Panda and Mallick, "Enhanced poly-beta-hydroxybutyrate accumulation in a unicellular cyanobacterium, *Synechocystis* sp. PCC 6803", Letters in Applied Microbiology, 44(2):194-198 (2007).
Paulsen et al., "Microbial Genome Analyses: Global Comparisons of Transport Capabilities Based on Phylogenies, Bioenergetics and Substrate Specificities", J. Mol. Biol., 277(3):573-592 (1998).
Schmidt et al., "Heterotrophic High Cell-Density Fed-Batch Cultures of the Phycocyanin-Producing Red Alga *Galdieria sulphuraria*", Biotechnol. Bioeng., 90(1):77-84 (2005).

(56) References Cited

OTHER PUBLICATIONS

Sharma and Mallick, "Enhancement of poly-Beta-hydroxybutyrate accumulation in Nostoc muscorum under mixotrophy, chemoheterotrophy, and limitation of gas-exchange", Biotechnology Letters, 27:59-62 (2005).

Vazhappilly and Chen, "Eicosapentaenoic Acid and Docosahexaenoic Acid Production Potential of Microalgae and Their Potential for Heterotrophic Growth", JAOCS, 75(3):393-397 (1998).

Wang et al., "Characteristics of mixotrophic growth of *Synechocystis* sp. in an enclosed photobioreactor", Biotechnology Letters, 24:1593-1597 (2002).

Wen and Chen, "A perfusion-cell bleeding culture strategy for enhancing the productivity of eicosapentaenoic acid by Nitzschia laevis", Appl. Microbiol. Biotechnol., 57(3):316-322 (2001).

Sushchik et al., "A Temperature Dependence of the Intra- and Extracellular Fatty-Acid Composition of Green Algae and Cyanobacterium", Russian Journal of Plant Physiology, 50(3):374-380 (2003). Translated from Fiziologiya Rastenii, 50(3):420-427 (2003).

Welker et al.: "*Cyanobacterial peptides—Nature's own combinatorial biosynthesis*"; FEMS Microbiology Reviews 30(4):530-563, 2006.

Michinaka et al.: "*Extracellular Secretion of Free Fatty Acids by Disruption of a Fatty Acyl-CoA Synthetase Gene in Saccharornyces cervisiae*"; (2003) J. Bioscience and Bioengineering 95: 435-440.

Issued (translated) claims, Chinese Patent No. ZL 200880126568.0.

European Office Action and Claims regarding EP 08860168.7.

Issued (translated) claims Japanese Patent No. 5465183.

Chen et al.: "*Controlled Expression of an rpoS Antisense RNA Can Inhibit RpoSFunction in Escherichia coil*"; Antimicrobial Agents and Chemotherapy, (2003) 47:3485-3493.

Kedar et al.: "*Evaluation of the metS and murB Loci for Antibiotic Discovery Using Targeted Antisense RNA Expression Analysis in Bacillus anthracis*"; Antimicrobial Agents and Chemotherapy (2007) 51:1708-1718.

Kernodle et al.: "*Expression of an Antisense hla Fragment in Staphylococcus aureus Reduces Alpha-Toxin Production In Vitro and Attenuates Lethal Activity in a Murine Model*"; Infection and Immunity (1997) 65:179-184.

Lo et al.: "*Crystal Structure of Escherichia coli Thioesterasel/ Protease I/Lysophospholipase Consensus Sequence Blocks Constitute the Catalytic Center of SGNH-hydrolases through a Conserved Hydrogen Bond Network*"; J. Mol. Biol. (2003) 330:539-551.

Tummala et al.: "*Design of Antisense RNA Constructs for Downregulation of the Acetone Formation Pathway of Clostridium acetobutylicum*"; J. Bacteriol. (2003) 185:1923-1934.

\* cited by examiner

Integrated CO₂ delivery and product recovery schematic

CO$_2$-mediated acidification of hydrophobic adsorption column load

SECRETION OF FATTY ACIDS BY PHOTOSYNTHETIC MICROORGANISMS

CROSS-REFERENCE TO RELATED APPLICATIONS

This application is a divisional application of U.S. application Ser. No. 12/333,280 filed Dec. 11, 2008, now pending; which claims the benefit under 35 USC § 119(e) to U.S. Application Ser. No. 61/007,333 filed Dec. 11, 2007, now expired. The disclosure of each of the prior applications is considered part of and is incorporated by reference in the disclosure of this application.

BACKGROUND OF THE INVENTION

Field of the Invention

This invention relates to photosynthetic microorganisms that convert inorganic carbon to fatty acids and secrete them into the culture medium, methods of production of fatty acids using such organisms, and uses thereof. The fatty acids may be used directly or may be further modified to alternate forms such as esters, reduced forms such as alcohols, or hydrocarbons, for applications in different industries, including fuels and chemicals.

Background Information

Photosynthetic microorganisms, including eukaryotic algae and cyanobacteria, contain various lipids, including polar lipids and neutral lipids. Polar lipids (e.g., phospholipids, glycolipids, sulfolipids) are typically present in structural membranes whereas neutral lipids (e.g., triacylglycerols, wax esters) accumulate in cytoplasmic oil bodies or oil globules. A substantial research effort has been devoted to the development of methods to produce lipid-based fuels and chemicals from photosynthetic microorganisms. Typically, eukaryotic microalgae are grown under nutrient-replete conditions until a certain cell density is achieved, after which the cells are subjected to growth under nutrient-deficient conditions, which often leads to the accumulation of neutral lipids. The cells are then harvested by various means (e.g., settling, which can be facilitated by the addition of flocculants, followed by centrifugation), dried, and then the lipids are extracted from the cells by the use of various non-polar solvents. Harvesting of the cells and extraction of the lipids are cost-intensive steps. It would be desirable to obtain lipids from photosynthetic microorganisms without the requirement for cell harvesting and extraction.

PCT publication numbers WO2007/136762 and WO2008/119082 describe the production of biofuel components using microorganisms. These documents disclose the production by these organisms of fatty acid derivatives which are, apparently, short and long chain alcohols, hydrocarbons, fatty alcohols and esters including waxes, fatty acid esters or fatty esters. To the extent that fatty acid production is described, it is proposed as an intermediate to these derivatives, and the fatty acids are therefore not secreted. Further, there is no disclosure of converting inorganic carbon directly to secreted fatty acids using a photosynthetic organism grown in a culture medium containing inorganic carbon as the primary carbon source. The present invention takes advantage of the efficiency of photosynthetic organisms in secreting fatty acids into the medium in order to recover these valuable compounds.

The invention includes the expression of heterologous acyl-ACP thioesterase (TE) genes in photosynthetic microbes. Many of these genes, along with their use to alter lipid metabolism in oilseeds, have been described previously. Genes encoding the proteins that catalyze various steps in the synthesis and further metabolism of fatty acids have also been extensively described.

The two functional classes of plant acyl-ACP thioesterases (unsaturated fatty acid-recognizing Fat A versus saturated fatty acid-recognizing FatB) can be clustered based on amino acid sequence alignments as well as function. FatAs show marked preference for 18:1-ACP with minor activity towards 18:0- and 16:0-ACPs, and FatBs hydrolyze primarily saturated acyl-ACPs with chain lengths that vary between 8-16 carbons. Several studies have focused on engineering plant thioesterases with perfected or altered substrate specificities as a strategy for tailoring specialty seed oils.

As shown in FIG. 1, fatty acid synthetase catalyzes a repeating cycle wherein malonyl-acyl carrier protein (ACP) is condensed with a substrate, initially acetyl-CoA, to form acetoacetyl-ACP, liberating $CO_2$. The acetoacetyl-ACP is then reduced, dehydrated, and reduced further to butyryl-ACP which can then itself be condensed with malonyl-ACP, and the cycle repeated, adding a 2-carbon unit at each turn. The production of free fatty acids would therefore be enhanced by a thioesterase that would liberate the fatty acid itself from ACP, breaking the cycle. That is, the acyl-ACP is prevented from reentering the cycle. Production of the fatty acid would also be encouraged by enhancing the levels of fatty acid synthetase and inhibiting any enzymes which result in degradation or further metabolism of the fatty acid.

FIG. 2 presents a more detailed description of the sequential formation of acyl-ACPs of longer and longer chains. As shown, the thioesterase enzymes listed in FIG. 2 liberate the fatty acid from the ACP thioester.

Taking advantage of this principle, Dehesh, K., et al., *The Plant Journal* (1996) 9:167-172, describe "Production of high levels of octanoic (8:0) and decanoic (10:0) fatty acids in transgenic canola by overexpression of ChFatB2, a thioesterase cDNA from *Cuphea hookeriana*." Dehesh, K., et al., *Plant Physiology* (1996) 110:203-210, and report "Two novel thioesterases are key determinants of the bimodal distribution of acyl chain length of *Cuphea palustris* seed oil."

Voelker, T., et al., *Science* (1992) 257:72-74, describe "Fatty acid biosynthesis redirected to medium chains in transgenic oilseed plants." Voelker, T., and Davies, M., *Journal of Bacteriology* (1994) 176:7320-7327, describe "Alteration of the specificity and regulation of fatty acid synthesis of *Escherichia coli* by expression of a plant medium-chain acyl-acyl carrier protein thioesterase."

SUMMARY OF THE INVENTION

The present invention is directed to the production of recombinant photosynthetic microorganisms that are able to secrete fatty acids derived from inorganic carbon into the culture medium. Methods to remove the secreted fatty acids from the culture medium without the need for cell harvesting are also provided. It is anticipated that these improvements will lead to lower costs for producing lipid-based fuels and chemicals from photosynthetic microorganisms. In addition, this invention enables the production of fatty acids of defined chain length, thus allowing their use in the formulation of a variety of different products, including fuels and chemicals.

Carbon dioxide (which, along with carbonic acid, bicarbonate and/or carbonate define the term "inorganic carbon") is converted in the photosynthetic process to organic compounds. The inorganic carbon source includes any way of delivering inorganic carbon, optionally in admixture with any other combination of compounds which do not serve as the primary carbon feedstock, but only as a mixture or carrier (for example, emissions from biofuel (e.g., ethanol) plants, power plants, petroleum-based refineries, as well as atmospheric and subterranean sources).

One embodiment of the invention relates to a culture of recombinant photosynthetic microorganisms, said organisms comprising at least one recombinant expression vector encoding at least one exogenous acyl-ACP thioesterase, wherein the at least one exogenous acyl-ACP thioesterase preferentially liberates fatty acid chains containing 6 to 20 carbons from these ACP thioesters. The fatty acids are formed from inorganic carbon as their carbon source and the culture contains substantially only inorganic carbon as a carbon source. The presence of the exogenous thioesterase will increase the secretion levels of desired fatty acids by at least 2-4 fold.

Specifically, in one embodiment, the invention is directed to a cell culture of a recombinant photosynthetic microorganism where the microorganism has been modified to contain a nucleic acid molecule comprising at least one recombinant expression system that produces at least one exogenous acyl-ACP thioesterase, wherein said acyl-ACP thioesterase preferentially liberates a fatty acid chain that contains 6-20 carbons, and wherein the culture medium provides inorganic carbon as substantially the sole carbon source and wherein said microorganism secretes the fatty acid liberated by the acyl-ACP thioesterase into the medium. In alternative embodiments, the thioesterase preferentially liberates a fatty acid chain that contains 6, 7, 8, 9, 10, 11, 12, 13, 14, 15, 16, 17, 18, 19 or 20 carbons.

In other aspects, the invention is directed to a method to produce fatty acids of desired chain lengths by incubating these cultures and recovering these secreted fatty acids from the cultures. In one embodiment, the recovery employs solid particulate adsorbents to harvest the secreted fatty acids. The fatty acids thus recovered can be further modified synthetically or used directly as components of biofuels or chemicals.

DETAILED DESCRIPTION OF THE INVENTION

The present invention provides photosynthetic microorganisms that secrete fatty acids into the culture medium, along with methods to adsorb the fatty acids from the culture medium and collect them for processing into fuels and chemicals. The invention thereby eliminates or greatly reduces the need to harvest and extract the cells, resulting in substantially reduced production costs.

Figure 1:
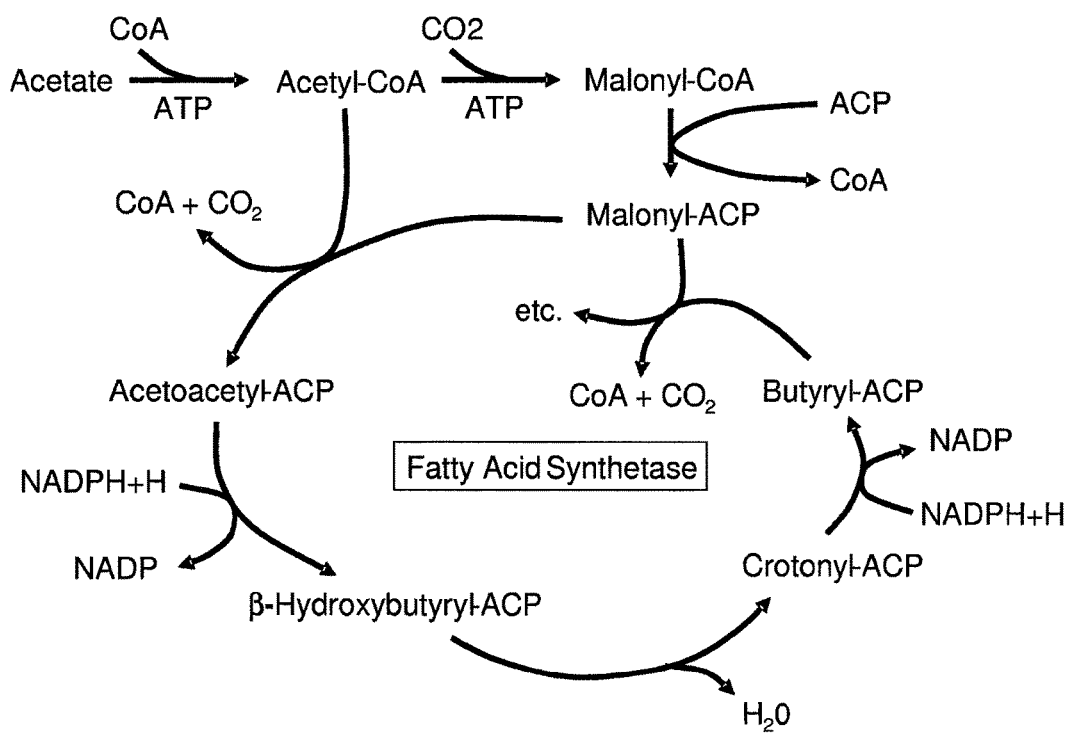
FIG. 1 is a diagram of the pathway of fatty acid synthesis as is known in the art.
Figure 2:
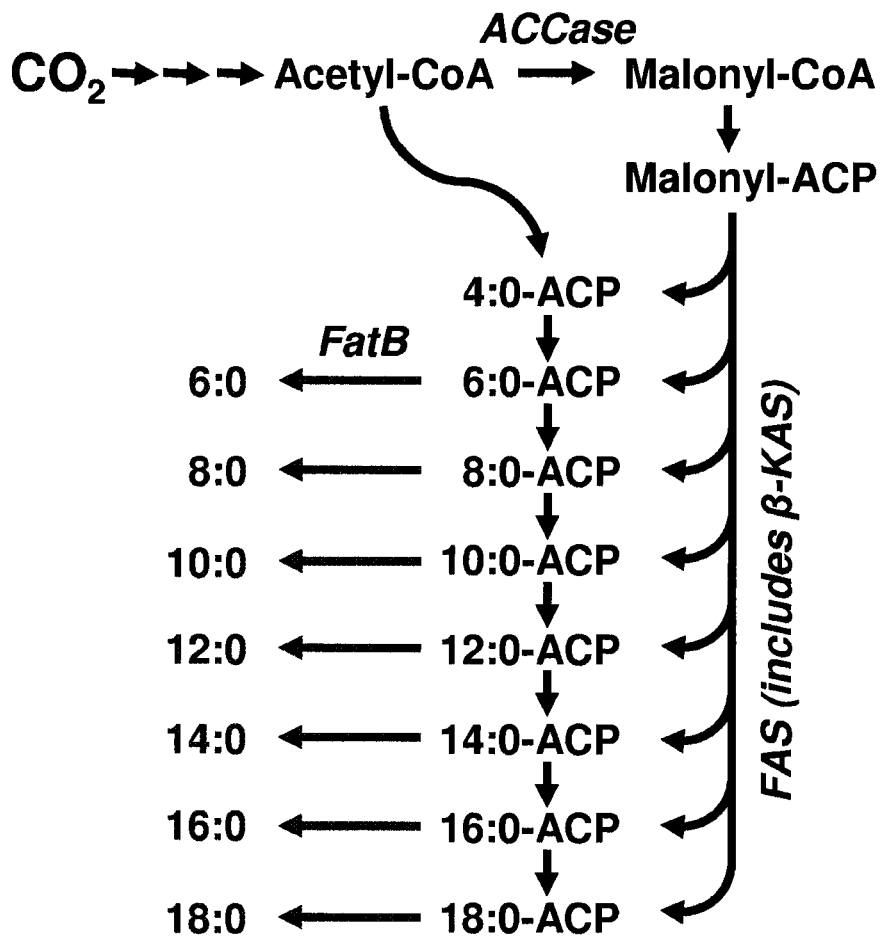
FIG. 2 is a more detailed diagram of the synthesis of fatty acids of multiple chain lengths as is known in the art.
Figure 3:
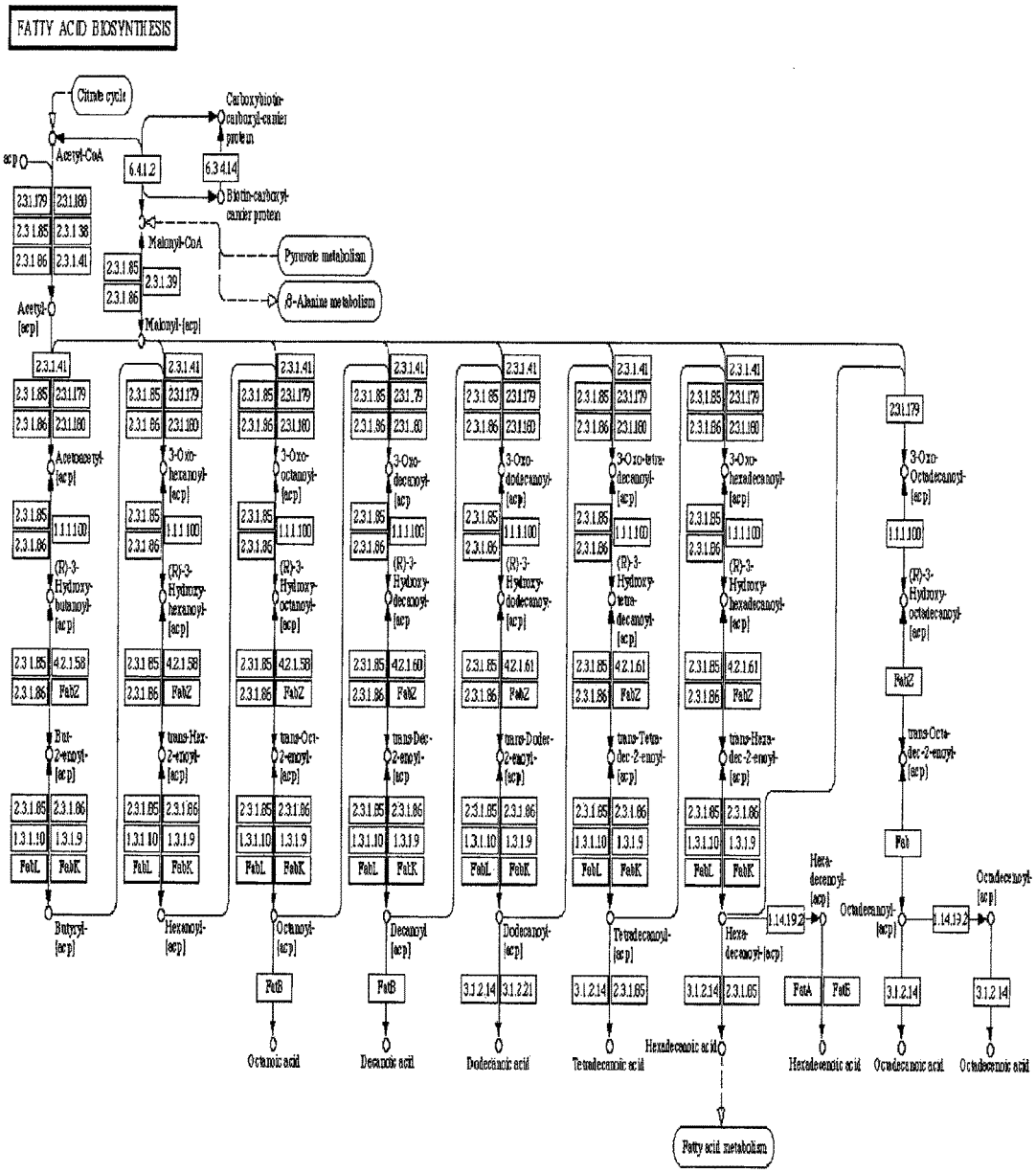
FIG. 3 is an enzymatic overview of fatty acid biosynthesis identifying enzymatic classes for the production of various chain length fatty acids.
Figure 4:
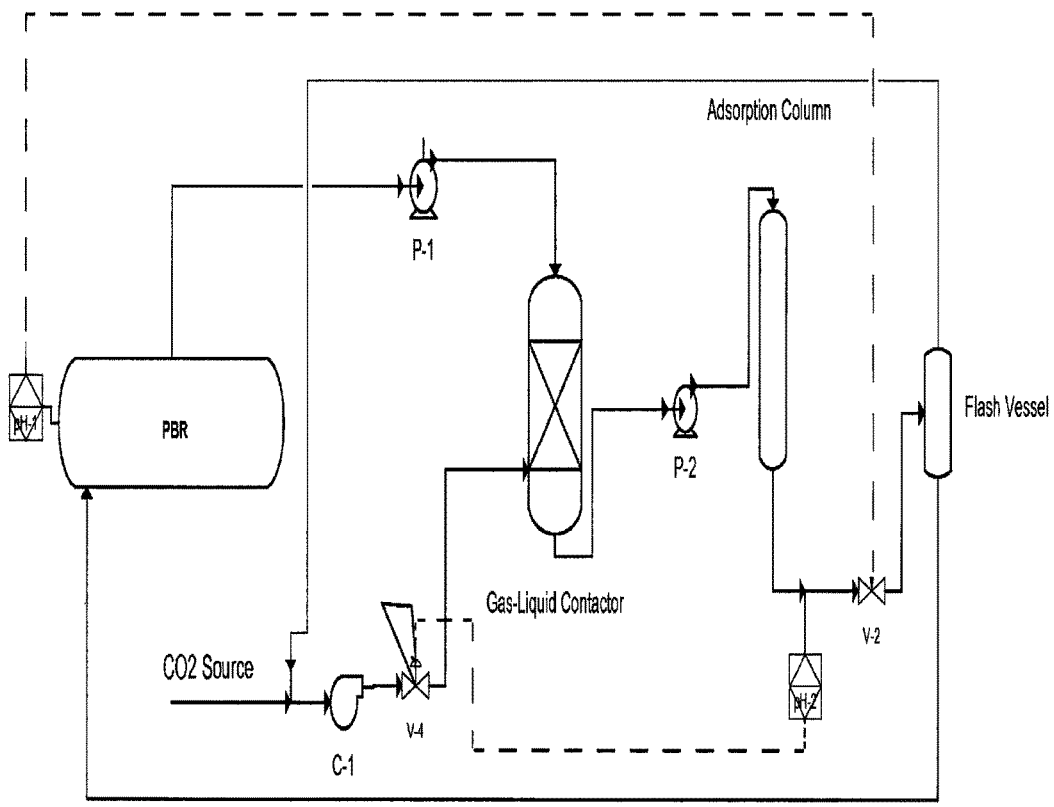
FIG. 4 is a schematic diagram of a recovery system for fatty acids from the medium.

FIG. 2 is an overview of one aspect of the invention. As shown in FIG. 2, carbon dioxide is converted to acetyl-CoA using the multiple steps in the photosynthetic process. The acetyl-CoA is then converted to malonyl-CoA by the action of acetyl-CoA carboxylase. The malonyl-CoA is then converted to malonyl-ACP by the action of malonyl-CoA:ACP transacylase which, upon progressive action of fatty acid synthetase, results in successive additions of two carbon units. In one embodiment of the invention, the process is essentially halted at carbon chain lengths of 6 or 8 or 10 or 12 or 14 or 16 or 18 carbons by supplying the appropriate thioesterase (shown in FIG. 2 as FatB). To the extent that further conversions to longer chain fatty acids occur in this embodiment, the cell biomass can be harvested as well. The secreted fatty acids can be converted to various other forms including, for example, methyl esters, alkanes, alkenes, alpha-olefins and fatty alcohols.

Thioesterases (Acyl-ACP TEs)

In order to effect secretion of the free fatty acids, the organism is provided at least one expression system for at least one thioesterase that operates preferentially to liberate fatty acids of the desired length. Many genes encoding such thioesterases are available in the art. Some of these are subjects of U.S. patents as follows:

Examples include U.S. Pat. No. 5,298,421, entitled "Plant medium-chain-preferring acyl-ACP thioesterases and related methods," which describes the isolation of an acyl-ACP thioesterase and the gene that encodes it from the immature seeds of *Umbellularia californica*. Other sources for such thioesterases and their encoding genes include U.S. Pat. No. 5,304,481, entitled "Plant thioesterase having preferential hydrolase activity toward C12 acyl-ACP substrate," U.S. Pat. No. 5,344,771, entitled "Plant thioesterases," U.S. Pat. No. 5,455,167, entitled "Medium-chain thioesterases in plants," U.S. Pat. No. 5,512,482, entitled "Plant thioesterases," U.S. Pat. No. 5,530,186, entitled "Nucleotide sequences of soybean acyl-ACP thioesterase genes," U.S. Pat. No. 5,639,790, entitled "Plant medium-chain thioesterases," U.S. Pat. No. 5,667,997, entitled "C8 and C10 medium-chain thioesterases in plants," U.S. Pat. No. 5,723,761, entitled "Plant acyl-ACP thioesterase sequences," U.S. Pat. No. 5,807,893, entitled "Plant thioesterases and use for modification of fatty acid composition in plant seed oils," U.S. Pat. No. 5,850,022, entitled "Production of myristate in plant cells," U.S. Pat. No. 5,910,631, entitled "Middle chain-specific thioesterase genes from *Cuphea lanceolata*," U.S. Pat. No. 5,945,585, entitled "Specific for palmitoyl, stearoyl and oleoyl-alp thioesters nucleic acid fragments encoding acyl-ACP thioesterase enzymes and the use of these fragments in altering plant oil composition," U.S. Pat. No. 5,955,329, entitled "Engineering plant thioesterases for altered substrate specificity," U.S. Pat. No. 5,955,650, entitled "Nucleotide sequences of canola and soybean palmitoyl-ACP thioesterase genes and their use in the regulation of fatty acid content of the oils of soybean and canola plants," and U.S. Pat. No. 6,331,664, entitled "Acyl-ACP thioesterase nucleic acids from maize and methods of altering palmitic acid levels in transgenic plants therewith."

Others are described in the open literature as follows:

Dörmann, P. et al., *Planta* (1993) 189:425-432, describe "Characterization of two acyl-acyl carrier protein thioesterases from developing *Cuphea* seeds specific for medium-chain and oleoyl-acyl carrier protein." Dörmann, P., et al., *Biochimica Biophysica Acta* (1994) 1212:134-136, describe "Cloning and expression in *Escherichia coli* of a cDNA coding for the oleoyl-acyl carrier protein thioesterase from coriander (*Coriandrum sativum* L.)." Filichkin, S., et al., *European Journal of Lipid Science and Technology* (2006) 108:979-990, describe "New FATB thioesterases from a high-laurate *Cuphea* species: Functional and complementation analyses." Jones, A., et al., *Plant Cell* (1995) 7:359-371, describe "Palmitoyl-acyl carrier protein (ACP) thioesterase and the evolutionary origin of plant acyl-ACP thioesterases." Knutzon, D. S., et al., *Plant Physiology* (1992) 100:1751-1758, describe "Isolation and characterization of two safflower oleoyl-acyl carrier protein thioesterase cDNA clones." Slabaugh, M., et al., *The Plant Journal* (1998) 13:611-620, describe "Condensing enzymes from *Cuphea wrightii* associated with medium chain fatty acid biosynthesis."

Additional genes, not previously isolated, that encode these acyl-ACP TEs can be isolated from plants that naturally contain large amounts of medium-chain fatty acids in their seed oil, including certain plants in the Lauraceae, Lythraceae, Rutaceae, Ulmaceae, and Vochysiaceae families. Typically, the fatty acids produced by the seeds of these plants are esterified to glycerol and retained inside the cells. The seeds containing the products can then be harvested and processed to isolate the fatty acids. Other sources of these enzymes, such as bacteria may also be used.

The known acyl-ACP TEs from plants can be divided into two main classes, based on their amino acid sequences and their specificity for acyl-ACPs of differing chain lengths and degrees of unsaturation. The "FatA" type of plant acyl-ACP TE has preferential activity on oleoyl-ACP, thereby releasing oleic acid, an 18-carbon fatty acid with a single double bond nine carbons distal to the carboxyl group. The "FatB" type of plant acyl-ACP TE has preferential activity on saturated acyl-ACPs, and can have broad or narrow chain length specificities. For example, FatB enzymes from different species of *Cuphea* have been shown to release fatty acids ranging from eight carbons in length to sixteen carbons in length from the corresponding acyl-ACPs. Listed below in Table 1 are several plant acyl-ACP TEs along with their substrate preferences. (Fatty acids are designated by standard shorthand notation, wherein the number preceding the colon represents the acyl chain length and the number after the colon represents the number of double bonds in the acyl chain).

TABLE 1

Plant Acyl-ACP Thioesterase

| | |
|---|---|
| *Garcinia mangostana* FatA | 18:1 and 18:0 |
| *Carthamus tinctorius* FatA | 18:1 |
| *Coriandrum sativum* FatA | 18:1 |
| *Cuphea hookeriana* FatB1 | 16:0 |
| *Cuphea hookeriana* FatB2 | 8:0 and 10:0 |
| *Cuphea wrightii* FatB1 | 12:0 to 16:0 |
| *Cuphea palustris* FatB1 | 8:0 and 10:0 |
| *Cuphea palustris* FatB2 | 14:0 and 16:0 |
| *Cuphea calophylla* FatB1 | 12:0 to 16:0 |
| *Umbellularia californica* FatB1 | 12:0 |
| *Ulmus americana* FatB1 | 8:0 and 10:0 |

The enzymes listed in Table 1 are exemplary and many additional genes encoding acyl-ACP TEs can be isolated and used in this invention, including but not limited to genes such as those that encode the following acyl-ACP TEs (referred to by GenPept Accession Numbers):

CAA52069.1, CAA52070.1, CAA54060.1, CAA85387.1, CAA85388.1, CAB60830.1, CAC19933.1, CAC19934.1, CAC39106.1, CAC80370.1, CAC80371.1, CAD32683.1, CAL50570.1, CAN60643.1, CAN81819.1, CAO17726.1, CAO42218.1, CAO65585.1, CAO68322.1, AAA33019.1, AAA33020.1, AAB51523.1, AAB51524.1, AAB51525.1, AAB71729.1, AAB71730.1, AAB71731.1, AAB88824.1, AAC49001.1, AAC49002.1, AAC49179.1, AAC49180.1, AAC49269.1, AAC49783.1, AAC49784.1, AAC72881.1, AAC72882.1, AAC72883.1, AAD01982.1, AAD28187.1, AAD33870.1, AAD42220.2, AAG35064.1, AAG43857.1, AAG43858.1, AAG43859.1, AAG43860.1, AAG43861.1, AAL15645.1, AAL77443.1, AAL77445.1, AAL79361.1, AAM09524.1, AAN17328.1, AAQ08202.1, AAQ08223.1, AAX51636.1, AAX51637.1, ABB71579.1, ABB71581.1, ABC47311.1, ABD83939.1, ABE01139.1, ABH11710.1, ABI118986.1, ABI20759.1, ABI20760.1, ABL85052.1, ABU96744.1, EAY74210.1, EAY86874.1, EAY86877.1, EAY86884.1, EAY99617.1, EAZ0.1545.1, EAZ09668.1, EAZ12044.1, EAZ23982.1, EAZ37535.1, EAZ45287.1, NP_001047567.1, NP_001056776.1, NP_001057985.1, NP_001063601.1, NP_001068400.1, NP_172327.1, NP_189147.1, NP_193041.1, XP_001415703.1, Q39473, Q39513, Q41635, Q42712, Q9SQI3, NP_189147.1, AAC49002, CAA52070.1, CAA52069.1, 193041.1, CAC39106, CAO17726, AAC72883, AAA33020, AAL79361, AAQ08223.1, AAB51523, AAL77443, AAA33019, AAG35064, and AAL77445.

Figure 6:
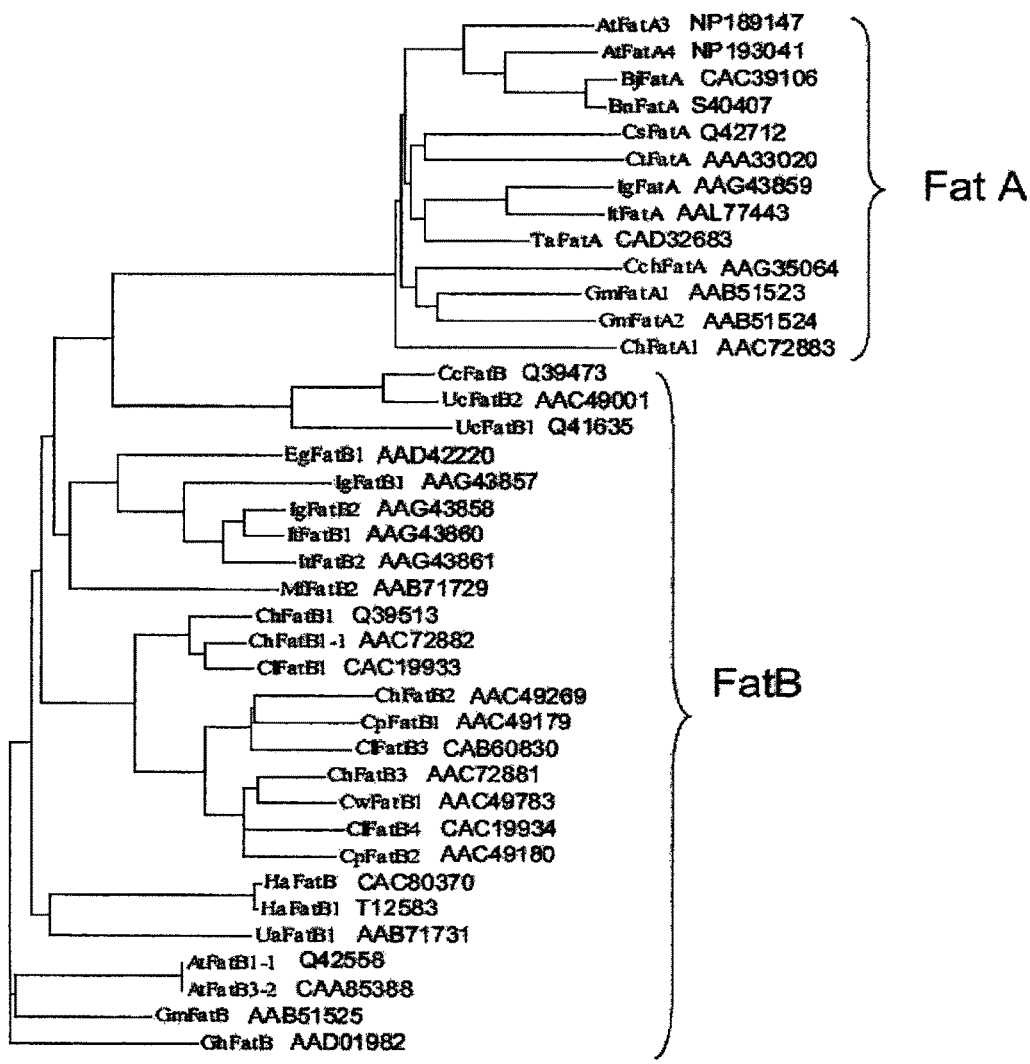
FIG. 6 shows representative acyl-ACP thioesterase from a variety of organisms.

Additional sources of acyl-ACP TEs that are useful in the present invention include: *Arabidopsis thaliana* (At); *Bradyrhizobium japonicum* (Bj); *Brassica napus* (Bn); *Cinnamonum camphorum* (Cc); *Capsicum chinense* (Cch); *Cuphea hookeriana* (Ch); *Cuphea lanceolata* (Ct); *Cuphea palustris* (Cp); *Coriandrum sativum* (Cs); *Carthamus tinctorius* (Ct); *Cuphea wrightii* (Cw); *Elaeis guineensis* (Eg); *Gossypium hirsutum* (Gh); *Garcinia mangostana* (Gm); *Helianthus annuus* (Ha); *Iris germanica* (Ig); *Iris tectorum* (It); *Myristica fragrans* (Mf); *Triticum aestivum* (Ta); *Ulmus Americana* (Ua); and *Umbellularia californica* (Uc). Exemplary TEs are shown in FIG. 6 with corresponding NCBI accession numbers.

In one embodiment, the present invention contemplates the specific production of an individual length of medium-chain fatty acid, for example, predominantly producing C8 fatty acids in one culture of recombinant photosynthetic microorganisms. In another embodiment, the present invention contemplates the production of a combination of two or more different length fatty acids, for example, both C8 and C10 fatty acids in one culture of recombinant photosynthetic microorganisms.

Illustrated below are manipulations of these art-known genes to construct suitable expression systems that result in production of effective amounts of the thioesterases in selected recombinant photosynthetic organisms. In such constructions, it may be desirable to remove the portion of the gene that encodes the plastid transit peptide region, as this region is inappropriate in prokaryotes. Alternatively, if expression is to take place in eukaryotic cells, the appropriate plastid transit peptide encoding region to the host organism may be substituted. Preferred codons may also be employed, depending on the host.

Other Modifications

In addition to providing an expression system for one or more appropriate acyl-ACP TE genes, further alterations in the photosynthetic host may be made. For example, the host may be modified to include an expression system for a heterologous gene that encodes a β-ketoacyl synthase (KAS) that preferentially produces acyl-ACPs having medium chain lengths. Such KAS enzymes have been described from several plants, including various species of *Cuphea*. See Dehesh, K., et al., *The Plant Journal* (1998) 15:383-390, describe "KAS IV: a 3-ketoacyl-ACP synthase from *Cuphea* sp. is a medium chain specific condensing enzyme."; Slabaugh, M., et al., *The Plant Journal* (1998) 13:611-620), and would serve to increase the availability of acyl-ACP molecules of the proper length for recognition and cleavage by the heterologous medium-chain acyl-ACP TE. Another example is that the photosynthetic host cell containing a heterologous acyl-ACP TE gene may be further modified to include an expression system for a heterologous gene that encodes a multifunctional acetyl-CoA carboxylase or a set of heterologous genes that encode the various subunits of a multi-subunit type of acetyl-CoA carboxylase. Other heterologous genes that encode additional enzymes or components of the fatty acid biosynthesis pathway could also be introduced and expressed in acyl-ACP TE-containing host cells.

The photosynthetic microorganism may also be modified such that one or more genes that encode beta-oxidation pathway enzymes have been inactivated or downregulated, or the enzymes themselves may be inhibited. This would prevent the degradation of fatty acids released from acyl-ACPs, thus enhancing the yield of secreted fatty acids. In cases where the desired products are medium-chain fatty acids, the inactivation or downregulation of genes that encode acyl-CoA synthetase and/or acyl-CoA oxidase enzymes that preferentially use these chain lengths as substrates would be beneficial. Mutations in the genes encoding medium-chain-specific acyl-CoA synthetase and/or medium-chain-specific acyl-CoA oxidase enzymes such that the activity of the enzymes is diminished would also be effective in increasing the yield of secreted fatty acids. An additional modification inactivates or down-regulates the acyl-ACP synthetase gene or inactivates the gene or protein. Mutations in the genes can be introduced either by recombinant or non-recombinant methods. These enzymes and their genes are well known, and may be targeted specifically by disruption, deletion, generation of antisense sequences, generation of ribozymes or other recombinant approaches known to the practitioner. Inactivation of the genes can also be accomplished by random mutation techniques such as UV, and the resulting cells screened for successful mutants. The proteins themselves can be inhibited by intracellular generation of appropriate antibodies or intracellular generation of peptide inhibitors.

The photosynthetic microorganism may also be modified such that one or more genes that encode storage carbohydrate or polyhydroxyalkanoate (PHA) biosynthesis pathway enzymes have been inactivated or down-regulated, or the enzymes themselves may be inhibited. Examples include enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

Expression Systems

Expression of heterologous genes in cyanobacteria and eukaryotic algae is enabled by the introduction of appropriate expression vectors. For transformation of cyanobacteria, a variety of promoters that function in cyanobacteria can be utilized, including, but not limited to the lac, tac, and trc promoters and derivatives that are inducible by the addition of isopropyl β-D-1-thiogalactopyranoside (IPTG), promoters that are naturally associated with transposon- or bacterial chromosome-borne antibiotic resistance genes (neomycin phosphotransferase, chloramphenicol acetyltransferase, spectinomycin adenyltransferase, etc.), promoters associated with various heterologous bacterial and native cyanobacterial genes, promoters from viruses and phages, and synthetic promoters. Promoters isolated from cyanobacteria that have been used successfully include the following:

secA (secretion; controlled by the redox state of the cell)
rbc (Rubisco operon)
psaAB (PS I reaction center proteins; light regulated)
psbA (D1 protein of PSII; light-inducible)

Likewise, a wide variety of transcriptional terminators can be used for expression vector construction. Examples of possible terminators include, but are not limited to, psbA, psaAB, rbc, secA, and T7 coat protein.

Expression vectors are introduced into the cyanobacterial strains by standard methods, including, but not limited to, natural DNA uptake, conjugation, electroporation, particle bombardment, and abrasion with glass beads, SiC fibers, or other particles. The vectors can be: 1) targeted for integration into the cyanobacterial chromosome by including flanking sequences that enable homologous recombination into the chromosome, 2) targeted for integration into endogenous cyanobacterial plasmids by including flanking sequences that enable homologous recombination into the endogenous plasmids, or 3) designed such that the expression vectors replicate within the chosen host.

For transformation of green algae, a variety of gene promoters and terminators that function in green algae can be utilized, including, but not limited to promoters and terminators from *Chlamydomonas* and other algae, promoters and terminators from viruses, and synthetic promoters and terminators.

Expression vectors are introduced into the green algal strains by standard methods, including, but not limited to, electroporation, particle bombardment, and abrasion with glass beads, SiC fibers, or other particles. The vectors can be 1) targeted for site-specific integration into the green algal chloroplast chromosome by including flanking sequences that enable homologous recombination into the chromosome, or 2) targeted for integration into the cellular (nucleus-localized) chromosome.

For transformation of diatoms, a variety of gene promoters that function in diatoms can be utilized in these expression vectors, including, but not limited to:
1) promoters from *Thalassiosira* and other heterokont algae, promoters from viruses, and synthetic promoters. Promoters from *Thalassiosira pseudonana* that would be suitable for use in expression vectors include an alpha-tubulin promoter (SEQ ID NO:1), a beta-tubulin promoter (SEQ ID NO:2), and an actin promoter (SEQ ID NO:3). Promoters from *Phaeodactylum tricornutum* that would be suitable for use in expression vectors include an alpha-tubulin promoter (SEQ ID NO:4), a beta-tubulin promoter (SEQ ID NO:5), and an actin promoter (SEQ ID NO:6). These sequences are deduced from the genomic sequences of the relevant organisms available in public databases and are merely exemplary of the wide variety of promoters that can be used. The terminators associated with these and other genes, or particular heterologous genes can be used to stop transcription and provide the appropriate signal for polyadenylation and can be derived in a similar manner or are known in the art.

Expression vectors are introduced into the diatom strains by standard methods, including, but not limited to, electroporation, particle bombardment, and abrasion with glass beads, SiC fibers, or other particles. The vectors can be 1) targeted for site-specific integration into the diatom chloroplast chromosome by including flanking sequences that enable homologous recombination into the chromosome, or 2) targeted for integration into the cellular (nucleus-localized) chromosome.

Host Organisms

The host cells used to prepare the cultures of the invention include any photosynthetic organism which is able to convert inorganic carbon into a substrate that is in turn converted to fatty acid derivatives. These organisms include prokaryotes as well as eukaryotic organisms such as algae and diatoms.

Host organisms include eukaryotic algae and cyanobacteria (blue-green algae). Representative algae include green algae (chlorophytes), red algae, diatoms, prasinophytes, glaucophytes, chlorarachniophytes, euglenophytes, chromophytes, and dinoflagellates. A number of cyanobacterial species are known and have been manipulated using molecular biological techniques, including the unicellular cyanobacteria *Synechocystis* sp. PCC6803 and *Synechococcus elongates* PCC7942, whose genomes have been completely sequenced.

The following genera of cyanobacteria may be used: one group includes

| |
|---|
| *Chamaesiphon* |
| *Chroococcus* |
| *Cyanobacterium* |
| *Cyanobium* |
| *Cyanothece* |
| *Dactylococcopsis* |
| *Gloeobacter* |
| *Gloeocapsa* |
| *Gloeothece* |
| *Microcystis* |
| *Prochlorococcus* |
| *Prochloron* |
| *Synechococcus* |
| *Synechocystis* |

Another group includes

| |
|---|
| *Cyanocystis* |
| *Dermocarpella* |
| *Stanieria* |
| *Xenococcus* |
| *Chroococcidiopsis* |
| *Myxosarcina* |
| *Pleurocapsa* |

Still another group includes

| |
|---|
| *Arthrospira* |
| *Borzia* |
| *Crinalium* |
| *Geitlerinema* |
| *Halospirulina* |
| *Leptolyngbya* |
| *Limnothrix* |
| *Lyngbya* |
| *Microcoleus* |
| *Oscillatoria* |
| *Planktothrix* |
| *Prochlorothrix* |
| *Pseudanabaena* |
| *Spirulina* |
| *Starria* |
| *Symploca* |
| *Trichodesmium* |
| *Tychonema* |

Still another group includes

| |
|---|
| *Anabaena* |
| *Anabaenopsis* |
| *Aphanizomenon* |
| *Calothrix* |
| *Cyanospira* |
| *Cylindrospermopsis* |
| *Cylindrospermum* |
| *Nodularia* |
| *Nostoc* |
| *Rivularia* |
| *Scytonema* |
| *Tolypothrix* |

And another group includes

| |
|---|
| *Chlorogloeopsis* |
| *Fischerella* |
| *Geitleria* |
| *Iyengariella* |
| *Nostochopsis* |
| *Stigonema* |

In addition, various algae, including diatoms and green algae can be employed.

Desirable qualities of the host strain include high potential growth rate and lipid productivity at 25-50° C., high light intensity tolerance, growth in brackish or saline water, i.e., in wide range of water types, resistance to growth inhibition by high $O_2$ concentrations, filamentous morphology to aid harvesting by screens; resistance to predation, ability to be flocculated (by chemicals or 'on-demand autoflocculation'), excellent inorganic carbon uptake characteristics, virus or cyanophage-resistance, tolerance to free fatty acids or other compounds associated with the invention method, and ability to undergo metabolic engineering.

Metabolic engineering is facilitated by the ability to take up DNA by electroporation or conjugation, lack of a restriction system and efficient homologous recombination in the event gene replacement or gene knockouts are required.

Fatty Acid Adsorption, Removal, and Recovery

The fatty acids secreted into the culture medium by the recombinant photosynthetic microorganisms described above can be recovered in a variety of ways. A straightforward isolation method by partition using immiscible solvents may be employed. In one embodiment, particulate adsorbents can be employed. These may be lipophilic particulates or ion exchange resins, depending on the design of the recovery method. They may be circulating in the separated medium and then collected, or the medium may be passed over a fixed bed column, for example, a chromatographic column containing these particulates. The fatty acids are then eluted from the particulate adsorbents by the use of an appropriate solvent. Evaporation of the solvent, followed by further processing of the isolated fatty acids and lipids can then be carried out to yield chemicals and fuels that can be used for a variety of commercial purposes.

The particulate adsorbents may have average diameters ranging from 0.5 mm to 30 mm which can be manufactured from various materials including, but not limited to, polyethylene and derivatives, polystyrene and derivatives, polyamide and derivatives, polyester and derivatives, polyurethane and derivatives, polyacrylates and derivatives, silicone and derivatives, and polysaccharide and derivatives. Certain glass and ceramic materials can also be used as the solid support component of the fat adsorbing objects. The surfaces of the particulate adsorbents may be modified so that they are better able to bind fatty acids and lipids. An example of such modification is the introduction of ether-linked alkyl groups having various chain lengths, preferably 8-30 carbons. In another example, acyl chains of various lengths can be attached to the surface of the fat adsorbing objects via ester, thioester, or amide linkages.

In one embodiment, the particulate adsorbents are coated with inorganic compounds known to bind fatty acids and lipids. Examples of such compounds include but are not limited to aluminum hydroxide, graphite, anthracite, and silica.

The particles used may also be magnetized or otherwise derivatized to facilitate recovery. For instance the particles may be coupled to one member of a binding pair and the adsorbed to a substrate containing the relevant binding partner.

The fatty acids may be eluted from the particulate adsorbents by the use of an appropriate solvent such as hexane or ethanol. The particulate adsorbents may be reused by returning them to the culture medium or used in a regenerated column. The solvent containing the dissolved fatty acids is then evaporated, leaving the fatty acids in a purified state for further conversion to chemicals and fuels. The particulate adsorbents can be designed to be neutrally buoyant or positively buoyant to enhance circulation in the culture medium. A continuous cycle of fatty acid removal and recovery can be implemented by utilizing the steps outlined above. The recovered fatty acids may be converted to alternative organic compounds, used directly, or mixed with other components. Chemical methods for such conversions are well understood in the art, and developments of biological methods for such conversions are also contemplated.

The present invention further contemplates a variety of compositions comprising the fatty acids produced by the recombinant photosynthetic microorganisms described herein, and uses thereof. The composition may comprise the fatty acids themselves, or further derivatives of the fatty acids, such as alcohols, alkanes, and alkenes which can be generated from the fatty acids produced by the microorganisms by any methods that are known in the art, as well as by development of biological methods of conversion. For examples, fatty acids may be converted to alkenes by catalytic hydrogenation and catalytic dehydration.

The composition may serve, for example, as a biocrude. The biocrude can be processed through refineries that will convert the composition compounds to various petroleum and petrochemical replacements, including alkanes, olefins and aromatics through processes including hydrotreatment, decarboxylation, isomerization and catalytic cracking and reforming. The biocrude can be also converted to ester-based fuels, such as fatty acid methyl ester (commercially known as biodiesel), through established chemical processes including transesterification and esterification.

In addition, one of skill in the art could contemplate a variety of other uses for the fatty acids of the present invention, and derivatives thereof, that are well known in the art, for example, the production of chemicals, soaps, surfactants, detergents, lubricants, nutraceuticals, pharmaceuticals, cosmetics, etc. For example, derivatives of the fatty acids of the present invention include C8 chemicals, such as octanol, used in the manufacture of esters for cosmetics and flavors as well as for various medical applications, and octane, used primarily as a co-monomer in production of polyethylene. Derivatives of the fatty acids of the present invention may also include C10 chemicals, such as decanol, used in the manufacture of plasticizers, surfactants and solvents, and decene, used in the manufacture of lubricants.

Biocrudes are biologically produced compounds or a mix of different biologically produced compounds that are used as a feedstock for refineries in replacement of, or in complement to, crude oil or other forms of petroleum. In general, but not necessarily, these feedstocks have been pre-processed through biological, chemical, mechanical or thermal processes in order to be in a liquid state that is adequate for introduction in a petroleum refinery.

The fatty acids of the present invention can be a biocrude, and further processed to a biofuel composition. The biofuel can then perform as a finished fuel or a fuel additive.

"Finished fuel" is defined as a chemical compound or a mix of chemical compounds (produced through chemical, thermochemical or biological routes) that is in an adequate chemical and physical state to be used directly as a neat fuel or fuel additive in an engine. In many cases, but not always, the suitability of a finished fuel for use in an engine application is determined by a specification which describes the necessary physical and chemical properties that need to be met. Some examples of engines are: internal combustion engine, gas turbine, steam turbine, external combustion engine, and steam boiler. Some examples of finished fuels include: diesel fuel to be used in a compression-ignited (diesel) internal combustion engine, jet fuel to be used in an aviation turbine, fuel oil to be used in a boiler to generate steam or in an external combustion engine, ethanol to be used in a flex-fuel engine. Examples of fuel specifications are ASTM standards, mainly used ion the US, and the EN standards, mainly used in Europe.

"Fuel additive" refers to a compound or composition that is used in combination with another fuel for a variety of reasons, which include but are not limited to complying with mandates on the use of biofuels, reducing the consumption of fossil fuel-derived products or enhancing the performance of a fuel or engine. For example, fuel additives can be used to alter the freezing/gelling point, cloud point, lubricity, viscosity, oxidative stability, ignition quality, octane level, and flash point. Additives can further function as antioxidants, demulsifiers, oxygenates, thermal stability improvers, cetane improvers, stabilizers, cold flow improvers, combustion improvers, anti-foams, anti-haze additives, icing inhibitors, injector cleanliness additives, smoke suppressants, drag reducing additives, metal deactivators, dispersants, detergents, demulsifiers, dyes, markers, static dissipaters, biocides, and/or corrosion inhibitors.

The following examples are offered to illustrate but not to limit the invention.

EXAMPLE 1

Secretion of Fatty Acids by Strains Derived from the Unicellular Photoautotrophic Cyanobacterium *Synechococcus elongatus* PCC 7942

The *Cuphea hookeriana* FatB2 gene encoding an acyl-ACP thioesterase (ChFatB2) enzyme was modified for optimized expression in *Synechococcus elongatus* PCC 7942. First, the portion of the gene that encodes the plastid transit peptide region of the native ChFatB2 protein was removed. The remainder of the coding region was then codon-optimized using the "Gene Designer" software program (version 1.1.4.1) provided by DNA2.0, Inc. The nucleotide sequence of this derivative of the ChFatB2 gene (hereafter ChFatB2-7942) is provided as SEQ ID NO:7. The protein sequence encoded by this gene is provided in SEQ ID NO:8.

Two different versions of the trc promoter, trc (Egon, A., et al., Gene (1983) 25:167-178) and "enhanced trc" (hereafter trcE, from pTrcHis A, Invitrogen) were used to drive the expression of ChFatB2-7942 in S. elongatus PCC 7942. The trc promoter is repressed by the Lac repressor protein encoded by the lacIq gene and can be induced by the addition of isopropyl β-D-1-thiogalactopyranoside (IPTG). The trcE promoter is a derivative of trc designed to facilitate expression of eukaryotic proteins in E. coli and is also inducible by IPTG.

The fusion fragments of ChFatB2-7942 operably linked to trc or trcE, together with the lacIq gene, were cloned into the shuttle vector pAM2314 (Mackey, S. R., et al., Methods Mol. Biol. (2007) 362:115-129), which enables transformation of S. elongatus PCC 7942 via double homologous recombination-mediated integration into the "NS1" site of the chromosome. The constructed plasmid containing the trcE::ChFatB2-7942 expression cassette and lacIq gene is designated pSGI-YC01. SEQ ID NO:9 represents the sequence between and including the NS1 recombination sites of pSGI-YC01. The constructed plasmid containing the trc::ChFatB2-7942 expression cassette and lacIq gene is designated pSGI-YC09. SEQ ID NO: 10 represents the sequence between and including the NS1 recombination sites of pSGI-YC09.

Each of the plasmids pSGI-YC01 and pSGI-YC09, along with the control vector pAM2314, were introduced into wild-type S. elongatus PCC 7942 cells as described by Golden and Sherman (J. Bacteriol. (1984) 158:36-42). Both recombinant and control strains were pre-cultivated in 100 mL of BG-11 medium supplied with spectinomycin (5 mg/L) to late-log phase ($OD_{730nm}$=1.0) on a rotary shaker (150 rpm) at 30° C. with constant illumination (60 µE m$^{-2}$ sec$^{-1}$). Cultures were then subcultured at initial $OD_{730nm}$=0.4-0.5 in BG-11 and cultivated overnight to $OD_{730nm}$=0.7-0.9. For time-course study, 60 mL aliquots of the culture were transferred into 250-mL flasks and induced by adding IPTG (final conc.=1 mM) if applicable. Cultures were sampled 0, 48, 96, and 168 hours after IPTG induction and then filtered through Whatman®GF/F filters using a Millipore vacuum filter manifold. Filtrates were collected in screw top culture tubes for gas chromatographic (GC) analysis.

Free fatty acids (FFAs) were separated from filtered cell cultures using liquid-liquid extraction. Five mL of the filtrate were mixed with 125 µL of 1 M $H_3PO_4$ and 0.25 mL of 5 M NaCl, followed by addition of 2 mL of hexane and thorough mixing. For GC-FID analyze, a 0.2 µl sample of the hexane was injected using a 40:1 split ratio onto a DB-FFAP column (J&W Scientific, 15 m×250 µm×0.25 µm), with a temperature profile starting at 150° C. for 0.5 min, then heating at 15° C./min to 230° C. and holding for 7.1 min (1.1 mL/min He).

GC analysis results indicating the levels of medium-chain FFAs (8:0 and 10:0) in cultures containing various Synechococcus elongatus strains 168 hours after IPTG induction are shown in Table 1-1.

TABLE 1-1

Medium-Chain Fatty Acid Secretion in Various Strains of S. elongatus

| Strain | Parent Strain | Plasmid Added | Transgenes | Fatty Acids (mg/L) 8:0 | 10:0 |
|---|---|---|---|---|---|
| SGC-YC2-5 | PCC 7942 | pAM2314 | none | ND | ND |
| SGC-YC1-2 | PCC 7942 | pSGI-YC01 | trcE::ChFatB2-7942 | 1.5 | 3.5 |
| SGC-YC14-4 | PCC 7942 | pSGI-YC09 | trc::ChFatB2-7942 | 5.1 | 10.1 |

Note:
ND represents "not detected" (<1 mg/L).

EXAMPLE 2

Secretion of Fatty Acids by Strains Derived from the Unicellular Photoheterotrophic Cyanobacterium Synechocystis sp. PCC 6803

The trcE::ChFatB2-7942 and trc::ChFatB2-7942 fusion fragments, together with the lacIq gene, were cloned into the shuttle vector pSGI-YC03 (SEQ ID NO: 11), which enables transformation of Synechocystis sp. PCC 6803 via double homologous recombination-mediated integration into the "RS1" site of the chromosome (Williams, Methods Enzymol. (1988) 167:766-778). The constructed plasmid containing the trcE::ChFatB2-7942 expression cassette and lacIq gene is designated pSGI-YC08. SEQ ID NO:12 represents the sequence between and including the RS1 recombination sites of pSGI-YC08. The constructed plasmid containing the trc::ChFatB2-7942 expression cassette and lacIq gene is designated pSGI-YC14. SEQ ID NO: 13 represents the sequence between and including the RS1 recombination sites of pSGI-YC14.

Each of the plasmids pSGI-YC08, pSGI-YC14, and the control vector pSGI-YC03, was introduced into wild-type Synechocystis PCC 6803 cells, as described by Zang, X. et al., J Microbiol. (2007) 45:241-245. Both recombinant and control strains were pre-cultivated in 100 mL of BG-11 medium supplied with kanamycin (10 mg/L) to late-log phase ($OD_{730nm}$=1.0) on a rotary shaker (150 rpm) at 30° C. with constant illumination (60 µE·m$^{-2}$·sec$^{-1}$). Cultures were then subcultured at initial $OD_{730nm}$=0.4-0.5 in BG-11 and cultivated overnight to $OD_{730nm}$=0.7-0.9. For time-course studies, 60-mL aliquots of the culture were transferred into 250-mL flasks and induced by adding IPTG (final conc.=1 mM) when applicable. Cultures were sampled 0, 72, and 144 hours after IPTG induction and then filtered through Whatman® GF/B filters using a Millipore vacuum filter manifold. Filtrates were collected in screw top culture tubes for gas chromatographic (GC) analysis. Free fatty acids (FFA) were separated from the filtered culture supernatant solutions by liquid-liquid extraction. For each sample, 2 mL filtered culture was extracted with a mixture of 50 µl phosphoric acid (1 M), 100 µl NaCl (5 M) and 2 mL hexane. A 0.2 µl sample was injected using a 40:1 split ratio on to a DB-FFAP column (J&W Scientific, 15 m×250 µm×0.25 µm), with a temperature profile starting at 150° C. for 0.5 min, then heating at 15° C./min to 230° C. and holding for 7.1 min (1.1 mL/min He).

GC analysis results indicating the levels of medium-chain FFAs (8:0 and 10:0) in cultures 144 hours after IPTG induction are shown in Table 2-1.

TABLE 2-1

Medium-Chain Fatty Acid Secretion in Various Strains of *Synechocystis*.

| Strain | Parent Strain | Plasmid Added | Transgenes | Fatty Acids (mg/L) | |
|---|---|---|---|---|---|
| | | | | 8:0 | 10:0 |
| SGC-YC9-8 | PCC 6803 | pSGI-YC03 | none | ND | ND |
| SGC-YC10-5 | PCC 6803 | pSGI-YC08 | trcE::ChFatB2-7942 | 61.3 | 52.7 |
| SGC-YC16-2 | PCC 6803 | pSGI-YC14 | trc::ChFatB2-7942 | 2.7 | 5.8 |

Note:
ND represents "not detected" (<1 mg/L).

EXAMPLE 3

Secretion of Fatty Acids by Strains Derived from the Filamentous Cyanobacterium *Anabaena variabilis* ATCC 29413

The trc::ChFatB2-7942 and trcE::ChFatB2-7942 fusion fragments, together with the lacIq gene, were PCR amplified using primers RS3-3F (SEQ ID NO:14) and 4YC-rrnBter-3 (SEQ ID NO:15) from pSGI-YC14 and pSGI-YC08, respectively, and then cloned into the shuttle vector pEL17, which enables transformation of *A. variabilis* ATCC 29413 via double homologous recombination-mediated integration into the nifU1 locus of the chromosome (Lyons and Thiel, J. Bacteriol. (1995) 177:1570-1575). The constructed plasmids are designated pSGI-YC69 and pSGI-YC70 for trc::ChFatB2-7942 and trcE::ChFatB2-7942, respectively.

Each of the plasmids pSGI-YC69, pSGI-YC70, along with the control vector pEL17, are introduced into wild-type *A. variabilis* ATCC 29413 cells via tri-parental conjugation, as described by Elhai and Wolk (*Methods Enzymol.* (1988) 167:747-754). Both recombinant and control strains are pre-cultivated in 100 mL of BG-11 medium supplied with 5 mM NH$_4$Cl and spectinomycin (3 mg/L) to late-log phase (OD$_{730nm}$=1.0) on a rotary shaker (150 rpm) at 30° C. with constant illumination (60 μE·m$^{-2}$·sec$^{-1}$). Cultures are then subcultured at initial OD$_{730nm}$=0.4-0.5 in BG-11 and cultivated overnight to OD$_{730nm}$=0.7-0.9. For time-course studies, 60-mL aliquots of the culture are transferred into 250 mL flasks and induced by adding IPTG (final conc.=1 mM) if applicable. Cultures are sampled every 72 hours and then filtered through Whatman® GF/F filters using a Millipore vacuum filter manifold. Filtrates are collected in screw top culture tubes for gas chromatographic (GC) analysis as described in Example 1.

EXAMPLE 4

Secretion of Fatty Acids in Strains Derived from *Synechococcus Elongatus* PCC 7942 Containing an Inactivated Acyl-ACP Synthetase Gene A putative acyl-ACP synthetase gene in *S. elongatus* PCC 7942, synpcc7942_0918 (Cyanobase gene designation), was disrupted via replacing of an internal 422-bp portion of its coding region with a 1,741-bp DNA sequence carrying the chloramphenicol resistance marker gene, cat (which encodes chloramphenicol acetyltransferase). Primer pairs 918-15 (SEQ ID NO:16)/918-13 (SEQ ID NO:17) and 918-25 (SEQ ID NO:18)/918-23 (SEQ ID NO:19) were used to amplify two DNA fragments corresponding to a 5' portion (1-480 bp) and a 3' portion (903-1521 bp) of the coding region of synpcc7942_0918, respectively. The cat fragment was amplified from plasmid pAM1573 (Mackey et al., Methods Mol. Biol. 362:115-29) using PCR with primers NS21-3Cm (SEQ ID NO:20) and ter-3Cm (SEQ ID NO:21), which overlap primers 918-13 and 918-25, respectively. The recombinant chimeric PCR technique was then used to amplify the complete disruption cassette with the three aforementioned PCR fragments, as well as primers 918-15 and 918-23. The resulting 2,840-bp blunt-end PCR fragment (SEQ ID NO:22) was then ligated into pUC19 (Yanisch-Perron et al., Gene 33:103-119), which has been digested with both HindIII and EcoRI to remove the multiple cloning sites and subsequently blunted with T4 DNA polymerase, to yield plasmid pSGI-YC04.

Plasmid pSGI-YC04 was introduced into *S. elongatus* strain SGC-YC1-2, which harbors a copy of trcE::ChFatB2-7942 integrated into NS1 (see Example 1). The resulting strain was designated SGC-YC4-7. Fatty acid production assays and GC analyses were performed as described in Example 1. The results of GC analyses indicating the levels of FFAs in cultures of various *S. elongatus* strains 168 hours after IPTG induction are shown in Table 4-1. It is possible that inactivation of the acyl-ACP synthetase gene has a larger impact on secretion of long-chain fatty acids than on secretion of medium-chain fatty acids.

TABLE 4-1

Medium-Chain Fatty Acid Secretion in Various Strains of *S. elongatus*.

| Strain | Parent Strain | Plasmid Added | Transgenes | Deletions | Fatty Acids (mg/L) | | | |
|---|---|---|---|---|---|---|---|---|
| | | | | | 8:0 | 10:0 | 16:0 | 16:1 |
| SGC-YC2-5 | PCC 7942 | pAM2314 | None | none | ND | ND | ND | 1.4 |
| SGC-YC1-2 | PCC 7942 | pSGI-YC01 | trcE::ChFatB2-7942 | none | 1.4 | 4.2 | ND | 1.6 |
| SGC-YC4-7 | SGC-YC1-2 | pSGI-YC04 | trcE::ChFatB2-7942 | synpcc7942_0918 | 1.0 | 3.1 | 1.1 | 3.9 |

Note:
ND represents "not detected" (<1 mg/L).

EXAMPLE 5

Secretion of Fatty Acids in Strains Derived from *Synechocystis* sp. PCC6803 Containing an Inactivated Acyl-ACP Synthetase Gene A ~1.7-kbp DNA fragment spanning an area upstream and into the coding region of the acyl-ACP synthetase-encoding gene, slr1609 (Cyanobase gene designation), from *Synechocystis* sp. PCC 6803 was amplified from genomic DNA using PCR with primers NB001 (SEQ ID NO:23) and NB002 (SEQ ID NO:24). This fragment was cloned into the pCR2.1 vector (Invitrogen) to yield plasmid pSGI-NB3 and subsequently cut with the restriction enzyme MfeI. A chloramphenicol resistance marker cassette containing the cat gene and associated regulatory control sequences was amplified from plasmid pAM1573 (Andersson, et al., *Methods Enzymol.* (2000) 305:527-542) to contain flanking MfeI restriction sites using PCR with primers NB010 (SEQ ID NO:25) and NB011 (SEQ ID NO:26). The cat gene expression cassette was then inserted into the MfeI site of pSGI-NB3 to yield pSGI-NB5 (SEQ ID NO:27).

The pSGI-NB5 vector was transformed into trcE:: ChFatB2-7942-containing *Synechocystis* strain SGC-YC10-5 (see Example 1) according to Zang et al., *J Microbiology* (2007) 45:241-245. Insertion of the chloramphenicol resistance marker into the Slr1609 gene through homologous recombination was verified by PCR screening of insert and insertion site. The resulting strain was designated SGC-NB10-4, which was tested in liquid BG-11 medium for fatty acid secretion. All liquid medium growth conditions used a rotary shaker (150 rpm) at 30° C. with constant illumination (60 µE·m$^{-2}$·sec$^{-1}$). Cultures were inoculated in 25 mL of BG-11 medium containing chloramphenicol and/or kanamycin (5 µg/mL) accordingly and grown to a sufficient density (minimal OD$_{730nm}$=1.6-2). Cultures were then used to inoculate 100 mL BG-11 medium in 250 mL polycarbonate flasks to OD$_{730nm}$=0.4-0.5 and incubated overnight. 45 mL of overnight culture at OD$_{730nm}$=0.7-0.9 were added to new 250 mL flasks, inducing with 1 mM IPTG or using as uninduced controls. 5 mL samples were taken at 0, 72 and 144 hours post induction and processed as described in Example 2.

Free fatty acids (FFA) were separated from the filtered culture supernatant solutions by liquid-liquid extraction for GC/FID (flame ionization detector) analysis. For each sample, 2 mL filtered culture was extracted with a mixture of 50 µl phosphoric acid (1 M), 100 µl NaCl (5 M) and 2 mL hexane. A 0.2 µl sample was injected using a 40:1 split ratio on to a DB-FFAP column (J&W Scientific, 15 m×250 µm×0.25 µm), with a temperature profile starting at 150° C. for 0.5 min, then heating at 15° C./min to 230° C. and holding for 7.1 min (1.1 mL/min He).

GC results indicating secreted levels of free fatty acids after 144 hours are shown in Table 5-1.

expression in *Synechococcus elongatus* PCC 7942, and the rps14 terminator (SEQ ID NO:28) from *Synechococcus* sp. WH8102. The nucleotide sequence of this entire functional operon, along with various flanking restriction enzyme recognition sites, is provided in SEQ ID NO:29.

Another DNA fragment comprising a functional operon was synthesized such that it contained the following elements in the given order: the trc promoter, the *Helianthus annuus* 3-ketoacyl-acyl carrier protein synthase III gene (HaKas-III, GenBank Accession No. ABP93352) codon-optimized for expression in both *Synechococcus elongatus* PCC 7942 and *Synechocystis* sp. PCC 6803, and rps14 terminator from *Synechococcus* sp. WH8102. The nucleotide sequence of this functional operon, along with various flanking restriction enzyme recognition sites, is provided in SEQ ID NO:30.

Codon optimization was performed by the use of the "Gene Designer" (version 1.1.4.1) software program provided by DNA2.0, Inc. The functional operon (expression cassette) containing the codon-modified ClKas-IV gene as represented in SEQ ID NO:29 was digested by the restriction enzymes SpeI and XbaI and inserted into plasmid pSGI-YC39 between the restriction sites SpeI and XbaI to form plasmid pSGI-BL26, which enables integration of the functional operon into the *Synechocystis* sp. PCC 6803 chromosome at the "RS2" recombination site (Aoki, et al., *J. Bacteriol* (1995) 177:5606-5611). The plasmid pSGI-BL27 containing the DNA fragment represented in SEQ ID NO:30 was constructed in the same way.

Plasmid pSGI-BL43 contains the trcE promoter, the codon-optimized ClKas-IV gene, and the rps14 terminator as represented in SEQ ID NO:31 and was made by inserting a SpeI/NcoI trcE fragment from pTrcHis A (Invitrogen) into SpeI/NcoI-digested pSGI-BL26. An additional plasmid, pSGI-BL44, contains the trcE promoter, the optimized ClKas-IV gene, the *S. elongatus* PCC 7942 kaiBC intergenic region, the optimized HaKas-III gene, and the rps14 terminator as represented in SEQ ID NO:32 and was made by inserting a BamHI/SacI fragment (containing the *S. elongatus* kaiBC intergenic region, the HaKas-III gene, and the rps14 terminator) generated via PCR amplification into BglII/SacI-digested pSGI-BL43. The PCR primers used to

TABLE 5.1

Medium-Chain Fatty Acid Secretion in Various Strains of *Synechocystis*.

| | | Plasmid | | | Fatty Acids (mg/L) | |
|---|---|---|---|---|---|---|
| Strain | Parent Strain | Added | Transgenes | Deletions | 8:0 | 10:0 |
| SGC-YC10-5 | PCC 6803 | pSGI-YC08 | trcE::ChFatB2-7942 | none | 58.3 | 67.7 |
| SGC-NB10-4 | SGC-YC10-5 | pSGI-NB5 | trcE::ChFatB2-7942 | slr1609 | 57.7 | 73.7 |

Note:
ND represents "not detected" (<1 mg/L).

EXAMPLE 6

Expression of *Cuphea lanceolata* Kas-IV and *Helianthus annuus* Kas-III Genes in *Synechocystis* sp A DNA fragment comprising a functional operon was synthesized such that it contained the following elements in the given order: the trc promoter, the *Cuphea* lanceolata 3-ketoacyl-acyl carrier protein synthase IV gene (ClKas-IV, GenBank Accession No. CAC59946) codon-optimized for generate the DNA fragment containing the kaiBC region, HaKas-III, and rps14 terminator are provided as SEQ ID NO:33 and SEQ ID NO:34.

Wild-type *Synechocystis* PCC 6803 cells and transgenic *Synechocystis* strain SGC-YC10-5, which contains the ChFatB2-7942 gene, were transformed with plasmids pSGI-BL26, pSGI-BL27, pSGI-BL43 and pSGI-BL44 as described by Zang, X. et al. *J. Microbiol.* (2007) 45:241-245. Both recombinant and wild-type control strains were pre-cultivated in 20 mL of BG-11 medium to mid-log phase (OD$_{730nm}$=0.7-0.9) on a rotary shaker (150 rpm) at 30° C.

with constant illumination (60 μE·m$^{-2}$·sec$^{-1}$). Kanamycin (5 μg/mL) and/or spectinomycin (10 g/mL) were included in recombinant cultures as appropriate. Cultures were then subcultured at initial OD$_{730nm}$=0.4-0.5 in BG-11 and cultivated overnight to OD$_{730nm}$=0.7-0.9. For a time-course study, 45-mL aliquots of the culture were transferred into 250 mL flasks and induced by adding IPTG (final conc.=1 mM) when applicable. Cultures were sampled 0, 72, and 144 hours after IPTG induction and then filtered through Whatman® GF/B filters using a Millipore vacuum filter manifold. Filtrates were collected in screw top culture tubes for gas chromatographic (GC) analysis as described in Example 2.

Results indicating the levels of secreted octanoic acid and decanoic acid in culture supernatants 144 hours after culture inoculation are shown in Table 6-1. The ClKas-IV and HaKas-III genes present in the indicated strains were under the control of the trc promoter.

TABLE 6-1

Medium-Chain Fatty Acid Secretion in (in mg/L) Various *Synechocystis* sp. Strains

| Strain | Parent Strain | Plasmid Added | Transgenes | Fatty Acids (mg/L) | |
|---|---|---|---|---|---|
| | | | | 8:0 | 10:0 |
| PCC 6803 | n/a | n/a | None | ND | ND |
| SGC-YC10-5 | PCC 6803 | pSGI-YC08 | trcE-ChFatB2-7942 | 69.8 | 68.4 |
| SGC-BL26-3 | PCC 6803 | pSGI-BL26 | trc-ClKas-IV | ND | ND |
| SGC-BL26-5 | SGC-YC10-5 | pSGI-BL26 | trcE-ChfatB2-7942 trc-ClKas-IV | 69.5 | 71.9 |
| SGC-BL27-1 | PCC 6803 | pSGI-BL27 | trc-HaKas-III | ND | ND |
| SGC-BL27-2 | SGC-YC10-5 | pSGI-BL27 | trcE-ChFatB2-7942 trc-HaKas-III | 65.7 | 66.6 |

Note:
ND represents "not detected" (<1 mg/L).

For a more optimized measurement of fatty acid secretion in these strains, the fatty acid secretion data shown in Table 6-1 were normalized to cell culture density, measured as optical density at 730 nm (OD$_{730nm}$); these data are presented in Table 6-2. Other experiments described in this application could be normalized in a similar fashion.

TABLE 6-2

Normalized Medium-Chain Fatty Acid Secretion (mg/L/OD$_{730\ nm}$) in Various *Synechocystis* sp. strains

| Strain | Parent Strain | Plasmid Added | Transgenes | Fatty Acids | |
|---|---|---|---|---|---|
| | | | | 8:0 | 10:0 |
| PCC 6803 | n/a | n/a | None | ND | ND |
| SGC-YC10-5 | PCC 6803 | pSGI-YC08 | trcE-ChFatB2-7942 | 11.7 | 11.4 |
| SGC-BL26-3 | PCC 6803 | pSGI-BL26 | trc-ClKas-IV | ND | ND |
| SGC-BL26-5 | SGC-YC10-5 | pSGI-BL26 | trcE-ChfatB2-7942 trc-ClKas-IV | 11.7 | 12.1 |
| SGC-BL27-1 | PCC 6803 | pSGI-BL27 | trc-HaKas-III | ND | ND |
| SGC-BL27-2 | SGC-YC10-5 | pSGI-BL27 | trcE-ChFatB2-7942 trc-HaKas-III | 12.2 | 12.3 |

Note:
ND represents "not detected" (<1 mg/L).

Results indicating the levels of secreted octanoic acid and decanoic acid in culture supernatants of additional strains 120 hours after culture inoculation are shown in Table 6-3. The ClKas-IV and HaKas-III genes present in the indicated strains were under the control of the trcE promoter.

TABLE 6-3

Medium-Chain Fatty Acid Secretion (in mg/L) in Various *Synechocystis* sp. Strains

| Strain | Parent Strain | Plasmid Added | Transgenes | Fatty Acids (mg/L) | |
|---|---|---|---|---|---|
| | | | | 8:0 | 10:0 |
| SGC-YC10-5 | PCC 6803 | pSGI-YC08 | trcE-ChFatB2-7942 | 34.8 | 43.5 |
| SGC-BL44 | PCC 6803 | pSGI-BL44 | trcE-ClKAS-IV + HaKAS-III | ND | ND |

TABLE 6-3-continued

Medium-Chain Fatty Acid Secretion (in mg/L) in Various *Synechocystis* sp. Strains

| Strain | Parent Strain | Plasmid Added | Transgenes | Fatty Acids (mg/L) 8:0 | 10:0 |
|---|---|---|---|---|---|
| SGC-YC10-5-BL43 | SGC-YC10-5 | pSGI-BL43 | trcE-ChFatB2-7942 trcE-ClKas-IV | 40.0 | 48.1 |
| SGC-YC10-5-BL44 | SGC-YC10-5 | pSGI-BL44 | trcE-ChfatB2-7942 trcE-ClKAS-IV + HaKAS-III | 38.5 | 47.1 |

Note:
ND represents "not detected" (<1 mg/L)

For a more optimized measurement of fatty acid secretion in these strains, the fatty acid secretion data shown in Table 6-1 were normalized to cell culture density, measured as optical density at 730 nm ($OD_{730nm}$); these data are presented in Table 6-4.

TABLE 6-4

Normalized Medium-Chain Fatty Acid Secretion ($mg/L/OD_{730\,nm}$) in Various *Synechocystis* sp. Strains

| Strain | Parent Strain | Plasmid Added | Transgenes | Fatty Acids 8:0 | 10:0 |
|---|---|---|---|---|---|
| SGC-YC10-5 | PCC 6803 | pSGI-YC08 | trcE-ChFatB2-7942 | 6.8 | 8.5 |
| SGC-BL44 | PCC 6803 | pSGI-BL44 | trcE-ClKAS-IV + HaKAS-III | ND | ND |
| SGC-YC10-5-BL43 | SGC-YC10-5 | pSGI-BL43 | trcE-ChFatB2-7942 trcE-ClKas-IV | 7.4 | 8.9 |
| SGC-YC10-5-BL44 | SGC-YC10-5 | pSGI-BL44 | trcE-ChfatB2-7942 trcE-ClKAS-IV + HaKAS-III | 8.3 | 10.2 |

EXAMPLE 7

Introduction of a Heterologous Acyl-ACP Thioesterase Gene into a Diatom

A synthetic gene that encodes a derivative of the ChFatB2 enzyme with specificity for medium-chain (8:0-10:0) acyl-ACPs is expressed in various diatoms (Bacillariophyceae) by constructing and utilizing expression vectors comprising the ChFatB2 gene operably linked to gene regulatory regions (promoters and terminators) that function in diatoms. In a preferred embodiment, the gene is optimized for expression in specific diatom species and the portion of the gene that encodes the plastid transit peptide region of the native ChFatB2 protein is replaced with a plastid transit peptide that functions optimally in diatoms. The nucleotide sequence provided as SEQ ID NO:35 represents a synthetic derivative of the ChFatB2 gene that has been optimized for expression in *Thalassiosira pseudonana* and in which the native plastid transit peptide-encoding region of the gene has been replaced with the plastid transit peptide (including coupled signal sequence) associated with the gamma subunit of the coupling factor portion (CF1) of the chloroplast ATP synthase from *T. pseudonana* (JGI Identifier=jgi/Thaps3/40156/est Ext_gwp_gwl.C_chr_40019). The protein encoded by this gene, referred to hereafter as ChFatB2-Thal,) is provided in SEQ ID NO:36.

To produce an expression vector for *T. pseudonana*, the ChFatB2-Thal gene was placed between the *T. pseudonana* alpha-tubulin promoter and terminator regulatory sequences. The alpha-tubulin promoter was amplified from genomic DNA isolated from *T. pseudonana* CCMP 1335 by use of primers PR1 (SEQ ID NO:37) and PR3 (SEQ ID NO:38), whereas the alpha-tubulin terminator was amplified by use of primers PR4 (SEQ ID NO:39) and PR8 (SEQ ID NO:40). The KpnI/BamHI fragment from the alpha-tubulin promoter amplicon, the BamHI/XbaI fragment from the alpha-tubulin terminator and the large fragment from KpnI/XbaI-cut pUC118 (Vieira and Messing, *Meth. Enzymol.* (1987) 153:3-11) were then combined to form pSGI-PR5. The NcoI/BamHI fragment from ChFatB2-Thal gene was then inserted into NcoI/BamHI-digested pSGI-PR5 to form pSGI-PR16. In addition, a codon-optimized gene that encodes the nourseothricin acetyltransferase (NAT) enzyme from *Streptomyces noursei* (SEQ ID NO:41) (Krugel, et al., *Gene* (1993) 127:127-131) was synthesized and the NcoI/BamHI fragment from this NAT-encoding DNA molecule was inserted into the large NcoI/BamHI fragment from pSGI-PR5 to form pSGI-PR7, which upon introduction into *T. pseudonana* and other diatoms can provide resistance to the antibiotic nourseothricin.

pSGI-PR16 and pSGI-PR7 were co-transformed into *T. pseudonana* CCMP 1335 by means of particle bombardment essentially as described by Poulsen, et al., (*J. Phycol.* (2006) 42:1059-1065). Transformed cells were selected on agar plates in the presence of 100 mg/L nourseothricin (ClonNAT, obtained from Werner BioAgents, Germany). The presence of the ChFatB2-Thal gene in cells was confirmed by the use of PCR. Transformants were grown in ASW liquid medium (Darley and Volcani, *Exp. Cell Res.* (1964) 58:334) on a rotary shaker (150 rpm) at 18° C. with constant illumination (60 $\mu E \cdot m^{-2} \cdot sec^{-1}$). Samples were removed seven days after inoculation and the culture medium was tested for the presence of FFAs as described in Example 1.

Although no fatty acid secretion was detected under these particular experimental conditions, optimization of the ChFatB2-Thal gene and diatom host strain can be performed to achieve fatty acid secretion in diatoms, which are known to have relatively impervious cell walls.

EXAMPLE 8

Secretion of Fatty Acids by Green Algae

A synthetic gene that encodes a derivative of the ChFatB2 enzyme with specificity for medium-chain (8:0-10:0) acyl-ACPs is expressed in green algae (Chlorophyceae) by constructing and utilizing expression vectors comprising the ChFatB2 gene operably linked to gene regulatory regions (promoters and terminators) that function in green algae. The gene is optimized for expression in specific green algal species and the portion of the gene that encodes the plastid transit peptide region of the native ChFatB2 protein is replaced with a plastid transit peptide that functions optimally in green algae. The nucleotide sequence provided as SEQ ID NO:42 represents a derivative of the ChFatB2 gene optimized for expression in *Chlamydomonas reinhardtii* and in which the native plastid transit peptide-encoding region of the gene has been replaced with the plastid transit peptide associated with the gamma subunit of the coupling factor portion (CF1) of the chloroplast ATP synthase from *C. reinhardtii* (GenPept Accession No. XP 001696335). The protein encoded by this gene is provided in SEQ ID NO:43.

EXAMPLE 9

Secretion of Fatty Acids in Strains of *Synechocystis* Sp. Containing a Disrupted 1,4-alpha-Glucan Branching Enzyme Gene A 1.4-kbp DNA fragment spanning an area upstream and into the coding region of the 1,4-alpha-glucan branching enzyme gene (glgB, Cyanobase gene designation=sll0158) from *Synechocystis* sp. PCC6803 was amplified from genomic DNA using PCR with primers glgB-5 (SEQ ID NO:44) and glgB-3 (SEQ ID NO:45). This fragment was cloned into the pCR4-Topo vector (Invitrogen) to yield plasmid pSGI-BL32 and subsequently cut with the restriction enzyme AvaI. A spectinomycin resistance marker cassette containing the aadA gene and associated regulatory control sequences was digested by HindIII from plasmid pSGI-BL27. Both of the linear fragments were treated with the Quick Blunting™ Kit (New England Biolabs). The aadA gene expression cassette was then inserted into the AvaI site of pSGI-BL32 to yield pSGI-BL33. The portion of pSGI-BL33 that inserts into and inactivates the glgB gene is provided as SEQ ID NO:46).

The pSGI-BL33 vector was transformed into wild-type *Synechocystis* PCC 6803 and into trcE::ChFatB2-7942-containing *Synechocystis* strain SGC-YC10-5 (see Example 1) according to Zang, et al., *J. Microbiology* (2007) 45:241-245. Insertion of the spectinomycin resistance marker into the Sll0158 (glgB) gene via homologous recombination was verified by PCR screening of insert and insertion site. Verified knockout strains were tested in liquid BG-11 medium for secretion of fatty acids. All liquid medium growth conditions used a rotary shaker (150 rpm) at 30° C. with constant illumination (60 $\mu E \cdot m^{-2} \cdot sec^{-1}$). Cultures were inoculated in 25 mL of BG-11 medium containing spectinomycin (10 µg/mL) and/or kanamycin (5 µg/mL) accordingly and grown to a sufficient density (minimal $OD_{730nm}$=1.6-2). Cultures were then used to inoculate 100 mL BG-11 medium in 250-mL polycarbonate flasks to $OD_{730nm}$=0.4-0.5 and incubated overnight. Forty-five mL of overnight culture at $OD_{730nm}$=0.5 were added to new 250-mL flasks; some cultures were induced with 1 mM IPTG or used as uninduced controls. Samples (0.5 mL) were taken at 0, 72, 144, and 216 hours post induction and processed as described in Example 2.

Free fatty acids (FFA) were separated from the filtered culture supernatant solutions by liquid-liquid extraction for GC/FID analysis. For each sample, 2 mL of filtered culture were extracted with a mixture of 50 µL phosphoric acid (1 M), 100 µL NaCl (5 M) and 2 mL hexane. A 0.2 µl sample was injected using a 40:1 split ratio on to a DB-FFAP column (J&W Scientific, 15 m×250 µm×0.25 µm), with a temperature profile starting at 150° C. for 0.5 min, then heating at 15° C./min to 230° C. and holding for 7.1 min (1.1 mL/min He).

GC results indicating secreted levels of free fatty acids after 216 hours are shown in Table 9-1.

TABLE 9-1

Medium-Chain Fatty Acid Secretion (in mg/L) in Various *Synechocystis* sp. Strains

| Strain | Parent Strain | Plasmid Added | Deletion | Transgenes | Fatty Acids 8:0 | 10:0 |
|---|---|---|---|---|---|---|
| PCC 6803 | n/a | n/a | None | None | ND | ND |
| SGC-BL33-1 | PCC 6803 | pSGI-BL33 | Sll0158 (glgB) | None | ND | ND |
| SGC-YC10-5 | PCC 6803 | pSGI-YC08 | None | trcE-ChFatB2-7942 | 70.0 | 68.7 |
| SGC-BL33-2 | SGC-YC10-5 | pSGI-BL33 | Sll0158 (glgB) | trcE-ChFatB2-7942 | 66.2 | 68.1 |

Note:
ND represents "not detected" (<1 mg/L).

For a more optimized measurement of fatty acid secretion in these strains, the fatty acid secretion data shown in Table 9-1 were normalized to cell culture density, measured as optical density at 730 nm ($OD_{730nm}$); these data are presented in Table 9-2. Other experiments described in this application could be normalized in a similar fashion.

TABLE 9-2

Normalized Medium-Chain Fatty Acid Secretion
(mg/L/OD$_{730\,nm}$) in Various *Synechocystis* sp. Strains

| Strain | Parent Strain | Plasmid Added | Deletion | Transgenes | Fatty Acids 8:0 | 10:0 |
|---|---|---|---|---|---|---|
| PCC 6803 | n/a | n/a | None | None | ND | ND |
| SGC-BL33-1 | PCC 6803 | pSGI-BL33 | Sll0158 (glgB) | None | ND | ND |
| SGC-YC10-5 | PCC 6803 | pSGI-YC08 | None | trcE-ChFatB2-7942 | 9.8 | 9.7 |
| SGC-BL33-2 | SGC-YC10-5 | pSGI-BL33 | Sll0158 (glgB) | trcE-ChFatB2-7942 | 10.4 | 10.7 |

Note:
ND represents "not detected" (<1 mg/L)

EXAMPLE 10

Capture of Free Fatty Acids from Model Solutions with Hydrophobic Adsorbent Resins A spike solution was formulated by dissolving 75 mg/L octanoic acid and 75 mg/L decanoic acid in BG-11 medium supplemented with 300 mM NaCl and adjusting the pH to 5.8. 50 mg of each of the resins listed in Table 1 were weighed into a 50 mL centrifuge tube and combined with 1.0 mL of methanol and shaken gently. The excess methanol was decanted and the resins were dried under a 25 in Hg vacuum, room temperature, overnight. 50 mL of the spike solution was then added to each of the resins and incubated with gentle shaking at 31° C. for 24 hours. Following incubation, the resins were removed by filtering over a Whatman® GF/F glass fiber filter and the filtrates were analyzed for octanoic acid and decanoic acid content by gas chromatography as described in Example 2. The capacity of each resin for octanoic and decanoic acid could then be determined by the difference in the concentration of each fatty acid before and after incubation with each resin. The results are shown in Table 10-1 below.

TABLE 10-1

Adsorption Capacities of Several Commercially-Available Adsorbents

| Description | Resin type | Adsorption Capacity (mg/g) Octanoic Acid | Decanoic acid | Total free fatty acids |
|---|---|---|---|---|
| Dowex Optipore ® V503 (Dow Chemical) | Post cross-linked macroporous polystyrene divinyl benzene | 26.3 | 69.8 | 96.0 |
| Lewatit 1064 MD (LanXess) | Macroporous polystyrene divinyl benzene | 1.1 | 46.7 | 47.8 |
| Zeolyst CBV 28014 (Zeolyst) | Very low-alumina zeolite | 17.4 | 74.7 | 92.0 |
| Zeolyst CBV 901 (Zeolyst) | Low-alumina zeolite | 5.4 | 64.8 | 70.1 |
| Hisiv 3000 Silicalite (UOP Honeywell) | Hydrophobic silicalite | 15.3 | 23.7 | 39.1 |
| Lipidex 5000 (Packard Instrument Co.) | Alkylated sephadex gel | 0.00 | 18.6 | 18.6 |
| Norit ROW 0.8 (Fluka) | Extruded activated charcoal | 40.2 | 71.8 | 112.1 |

Elution of free fatty acids from the hydrophobic adsorbents was also investigated. Dowex®Optipore®V503, Zeolyst CBV 28014, Zeolyst CBV 901, and Norit®ROW were incubated with 1.0 mL of spike solution per mg of adsorbent as described above. After the incubation period, the adsorbents were rinsed and combined with 0.1, 0.5, or 1.0 mL methanol per mg of adsorbent and shaken gently at room temperature for 4 hours. The methanol eluates and post-adsorption spikes were analyzed for free fatty acid concentration by gas chromatography. The results are listed in Table 10-2 below.

TABLE 10-2

Desorption of Free Fatty Acids in Methanol

| mL MeOH/mg Resin | % Desorption 0.1 mL/mg | 0.5 mL/mg | 1.0 mL/mg |
|---|---|---|---|
| Dowex Optipore ® V503 | 92% | 84% | 100% |
| CBV 28014 | 53% | 76% | 84% |
| CBV 901 | 78% | 76% | 57% |
| Norit ® ROW | 44% | 85% | 77% |

The effect of pH on adsorbent capacity was studied utilizing Dowex® Optipore® V503. 40 mg of the resin were combined with 40 mL of BG-11 media spiked with 150 mg/L of octanoic and decanoic acid and adjusted to a pH of 10.0, 7.5, 4.8, or 2.8. The pH 10 spike was buffered with 5 mM CAPS. The pH 7.5 and 2.8 spikes were buffered with 5 mM phosphate, and the pH 4.8 was buffered naturally by the dissolved fatty acids, with 5 mM NaCl added to maintain consistent conductivity. The spikes were incubated with resin as described above. Free fatty acid concentrations were measured with an enzymatic assay purchased from Zen-bio. The results are displayed in Table 10-3 below. From these results, it is clear that hydrophobic adsorption of free fatty acids is possible over a wide range of pH.

TABLE 10-3

Adsorption Capacity of Dowex® Optipore® V503
at Various pH Values

| pH | Adsorption Capacity (mg FFA/g resin) |
|---|---|
| 10 | 42 ± 13 |
| 7.5 | 64 ± 4 |
| 4.8 | 172 ± 4 |
| 2.8 | 259 ± 1 |

Reported values are the mean of two experimental replicates, +/− one standard deviation.

EXAMPLE 11

In Vivo Capture of Free Fatty Acids from Cultures of *Synechocystis* Strain SGC-YC10-5

*Synechocystis* sp. strain SGC-YC10-5, which contains the ChFatB2-7942 gene as described in Example 1, was cultured in BG-11 with and without Dowex® Optipore® V503 resin. 400 mL of fresh culture was induced with 5 mM IPTG and incubated at room temperature for 1 hour to allow for uptake of the inducer. The culture was then divided into four 1,000 mL baffled Erlenmeyer flasks with PTFE vent caps. To two of the flasks, approximately 400 mg of Dowex® Optipore® V503 were added. The adsorbent resin in the test flasks was recovered and exchanged for fresh resin daily for 10 days. The recovered resin was washed liberally with deionized water and eluted with 2 mL of methanol. Samples of culture medium from the test flasks and control flasks were also taken daily. The samples were measured for $OD_{730nm}$ and filtered over a Whatman® GF/B glass fiber filter and analyzed for octanoic acid and decanoic acid content by gas chromatography as previously described in Example 2. The results are presented in Table 11-1.

TABLE 11-1

In vivo capture of free fatty acids from
*Synechocystis* SGC-YC10-5 cultures

|  | Avg. Specific Growth Rate (d$^{-1}$) | Average Free Fatty Acid Productivity (mg L$^{-1}$ d$^{-1}$) |
|---|---|---|
| Without Dowex | 0.090 ± 0.005 | 16 ± 0.8 |
| With Dowex | 0.090 ± 0.010 | 31 ± 3 |

Reported values are the mean of two biological duplicates +/− one standard deviation.

EXAMPLE 12

Figure 5:
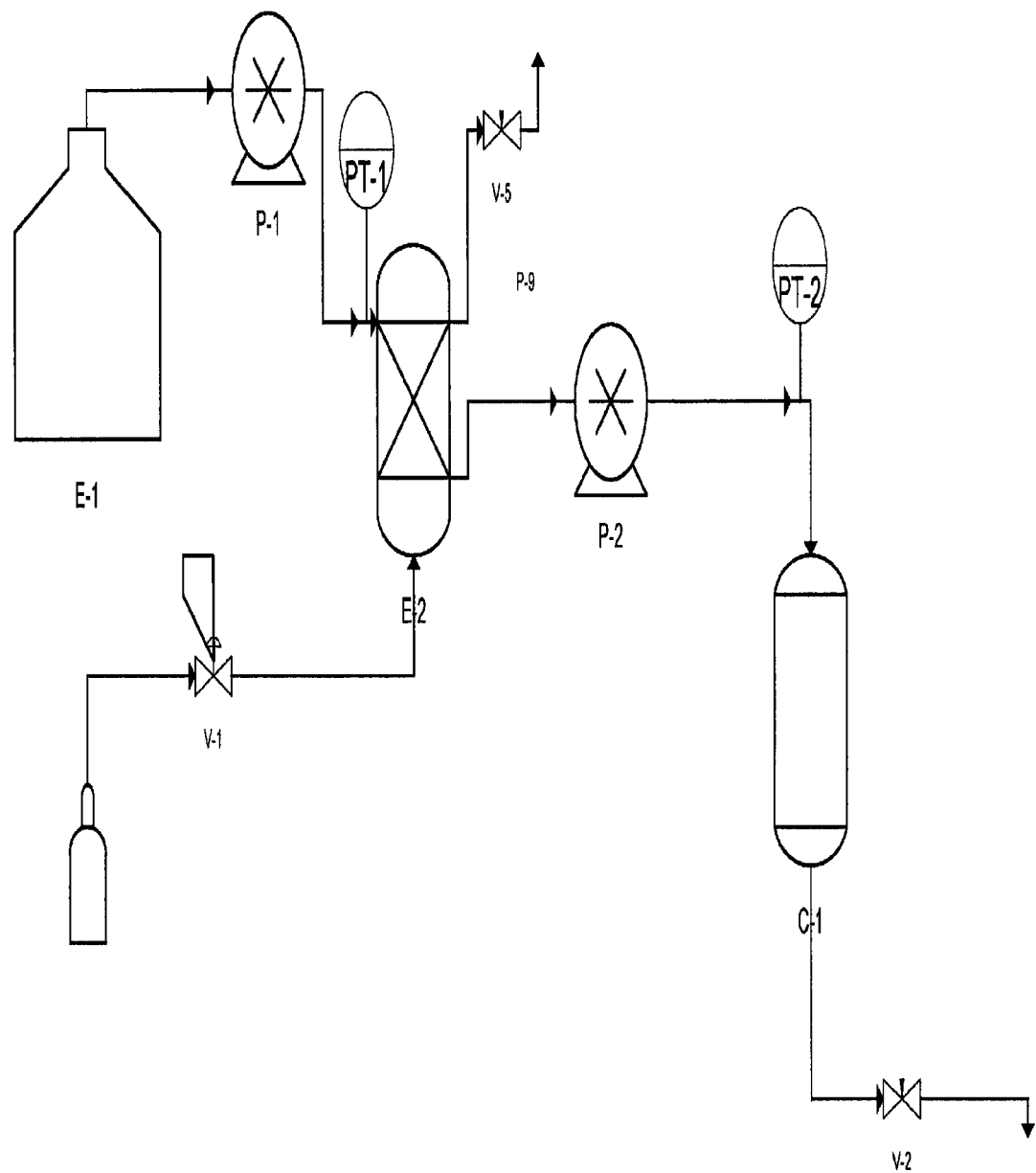
FIG. 5 shows an experimental system based on the principles in FIG. 4.

Integration of $CO_2$ Delivery and Product Recovery as a Means for Enhancing the Efficiency and Economy of Both Table 10-3 above reveals a clear relationship between free fatty acid adsorption capacity and pH. This relationship results from the inefficiency of extraction of the ionized form of the free fatty acids. Many potential production hosts require a pH significantly higher than the pKa of free fatty acids in order to survive and reproduce. An extreme example of this would be the alkalophilic cyanobacteria such as those belonging to the genera *Synechococcus*, *Synechocystis*, *Spirulina*, and many others, which prefer a pH between 9 and 11 for optimum growth. FIG. 5 outlines an embodiment of the invention wherein this problem is solved by recycling a portion of the culture first through a vessel where it is contacted with concentrated $CO_2$ gas to lower the pH, then through a stationary adsorbent column wherein the protonated free fatty acids are captured.

The $CO_2$-enriched, free fatty acid-depleted suspension is then returned to the bulk culture. The pressure inside the gas-liquid contactor can be controlled independently to provide a constant pH in the stream exiting the adsorption column. Further, the pressure of the post-column flash vessel can be controlled so as to provide a supply of $CO_2$ which is titrated to the $CO_2$ consumption rate of the bulk culture through PID control of pH, dissolved $CO_2$, off-gas $CO_2$, or any combination of the three. The excess $CO_2$ can then be recycled.

In order to demonstrate proof of concept for the invention described above, an experimental system was constructed as displayed in FIG. 5.

Vessel E-1 was filled with 4 L of a spike solution containing 700 mg/L octanoic acid dissolved in 100 mM NaCl, pH 11.1. Column C1 was filled with 45.2 g of Dowex®Optipore®V503 polymeric resin. The resin was activated with two column volumes of methanol, followed by a wash of three column volumes of 100 mM NaCl, pH 11.1. Liquid-gas contact vessel E2 was then filled with 200 mL of spike solution and 34.7 psia of $CO_2$. When the pH of the spike solution inside E-2 had decreased to between 5 and 6 (as determined by a slip of pH paper contained within E-2) peristaltic pumps P-1 and P-2 were set to the same flow rate and column loading was initiated. Valve V-2 was adjusted as needed to increase the column pressure and prevent the formation of gas bubbles.

Fractions of the flowthrough were taken at periodic intervals of 70-100 mL and assayed for octanoic acid by a commercially-available free fatty acid assay purchased from Zen-Bio. Two superficial linear flow rates were evaluated: 16.3 cm/min and 6.1 cm/min. For both flow rates, a control run was performed whereby vessel E-2 was bypassed and the column was loaded directly at a pH of 11.1. Table 12-1 below displays the results of this experiment. For both flow rates, column dynamic binding capacity was approximately 4-fold greater when $CO_2$ was used to lower the pH of the load.

TABLE 12-1

Dynamic binding capacity with and without
$CO_2$-mediated load acidification

| | Dynamic Binding Capacity (mg/g) | |
|---|---|---|
| Flow velocity (cm/min) | +34.7 psia $CO_2$ | Control (pH 11.1) 0 psia $CO_2$ |
| 6.1 | 43.5 | 10.5 |
| 16.3 | 7.2 | 1.9 |

EXAMPLE 13

Secretion of Oleic Acid by Photosynthetic Microorganisms

A synthetic gene that encodes a derivative of a FatA-type plant acyl-ACP TE enzyme with specificity for oleoyl-ACP is expressed in various photosynthetic microorganisms by constructing and utilizing expression vectors comprising a FatA gene operably linked to gene regulatory regions (promoters and terminators) that function in the host photosynthetic microorganism. The gene is optimized for expression in the host photosynthetic microorganism and the portion of the gene that encodes the plastid transit peptide region of the native FatA protein is removed for expression in cyanobacteria or replaced with a plastid transit peptide that functions effectively in the host eukaryotic photosynthetic microorganisms.

Genes that could be used for this purpose include, but are not limited to, those that encode the following acyl-ACP TEs (referred to by GenPept Accession Numbers): NP_189147.1, AAC49002, CAA52070.1, CAA52069.1, 193041.1, CAC39106, CAO17726, AAC72883, AAA33020, AAL79361, AAQ08223.1, AAB51523, AAL77443, AAA33019, AAG35064, and AAL77445.

What is claimed is:

1. A method to produce fatty acids, comprising:
   (i) incubating a cell culture of a recombinant cyanobacterium in a culture medium that provides inorganic carbon as substantially the sole carbon source for conversion to fatty acids by the cyanobacterium, wherein the cyanobacterium is modified to contain a nucleic acid molecule comprising at least one recombinant expression system that produces at least one exogenous acyl-acyl carrier protein (acyl-ACP) thioesterase, wherein said acyl-ACP thioesterase liberates a fatty acid chain that contains 6-20 carbons,
   wherein the recombinant cyanobacterium secretes the fatty acid formed from inorganic carbon into the culture medium; and
   (ii) recovering the secreted fatty acids from the culture medium.

2. The method of claim 1, wherein the fatty acids are recovered from the culture by contacting the medium with particulate adsorbents.

3. The method of claim 2, wherein the particulate adsorbents circulate in the medium.

4. The method of claim 2, wherein the particulate adsorbents are contained in a chromatographic column.

5. The method of claim 4, wherein the pH of the medium is lowered during said contacting.

6. The method of claim 5, wherein said pH lowering comprises adding $CO_2$.

7. The method of claim 6, wherein the medium is recirculated to the culture.

8. The method of claim 2, wherein the particulate adsorbents are lipophilic.

9. The method of claim 2, wherein the particulate adsorbents are ion exchange resins.

10. The method of claim 1, wherein the at least one exogenous acyl-ACP thioesterase is a Fat B thioesterase.

11. The method of claim 10, wherein the at least one exogenous acyl-ACP thioesterase is a Fat B thioesterase derived from the genus *Cuphea*.

12. The method of claim 11, wherein the at least one exogenous acyl-ACP thioesterase is *Cuphea hookeriana* FatB2 (ChFatB2).

13. The method of claim 1, further comprising inducing expression of the recombinant expression system that produces at least one exogenous acyl-acyl carrier protein (acyl-ACP) thioesterase.

14. The method of claim 1, wherein the recombinant cyanobacterium has further been modified to produce an exogenous β-ketoacyl synthase (KAS).

15. The method of claim 14, wherein the exogenous KAS produces acyl-ACPs having a chain length for which the thioesterase has activity.

16. The method of claim 1, wherein the recombinant cyanobacterium has further been modified to produce an exogenous acetyl-CoA carboxylase (ACCase).

17. The method of claim 1, wherein the recombinant cyanobacterium is further modified so that one or more genes encoding acyl-ACP synthetases are inactivated by gene disruption or downregulated by antisense RNA.

18. The method of claim 1, wherein the recombinant cyanobacterium is further modified so that one or more genes encoding a 1,4-alpha-glucan branching enzyme are inactivated by gene disruption or downregulated by antisense RNA.

19. A method to convert inorganic carbon to fatty acids, comprising:

(i) incubating a cell culture of a recombinant cyanobacterium in a culture medium that contains a carbon source consisting essentially of inorganic carbon, wherein the cyanobacterium is modified to contain a nucleic acid molecule comprising at least one recombinant expression system that produces at least one exogenous acyl-acyl carrier protein (acyl-ACP) thioesterase, wherein said acyl-ACP thioesterase liberates a fatty acid chain that contains 6-20 carbons, further wherein the recombinant cyanobacterium secretes the fatty acid into the culture;

and (ii) recovering the secreted fatty acids from the culture medium.

20. The method of claim 19, wherein the cyanobacterium is further modified to include means for inactivating or downregulating one or more genes encoding acyl-ACP synthetases.

21. The method of claim 19, wherein the cyanobacterium is further modified to include means for inactivating or downregulating one or more genes encoding a 1,4-alpha-glucan branching enzyme.

* * * * *

SEQUENCE LISTING

<160> NUMBER OF SEQ ID NOS: 46

<210> SEQ ID NO 1
<211> LENGTH: 723
<212> TYPE: DNA
<213> ORGANISM: Thalassiosira pseudonana

<400> SEQUENCE: 1

```
atatcgtgga gtatatcaat ggtggggagg tgtggtgtag tagttgcgag caaagatgac      60
acttggtaaa ctgatgcgac gtggatactg cgacgaagat tggccgtaca cacgtcggat     120
ttgaatgaac atatgtgttt tattcaaacc aatttgacta gtttgaggaa ccttcacgtg     180
tttcgctctc aaactttgag acaacagcct ccgaatccaa atgaatgact tttaaacaca     240
agctaggagc tggtgatata taatatgctg gttgtatgaa agagactaat cgtgtgaaat     300
aaatgatggc tcgccctagt gaatgctcct cagagacgct cattcgtcca agtgttcgtc     360
acttctgtca ttgtttcctc cgaggccaag gtggtcgagt aggtagatac cagctattct     420
cttgcttctt ttactttatc tccctctacc aaaaacagca cgttattatc tcctttccat     480
tccacgcaat aacaagaggc aatcggtaaa gaggcacaaa caagagaaca aagacccccgg    540
ctgcttctct cgtccgtccg ccgcccctaa acttcaagtt ttacttcaag ttcaatctgt     600
tttttggcgc aaaaagcgcc gttgctccgc cgtcctccgc acttttcagt tctctgtcgt     660
cgaggactgt tatcaacttc caagatctcc atctcttctc ctatcctccc ctaacaaagt     720
acg                                                                    723
```

<210> SEQ ID NO 2
<211> LENGTH: 700
<212> TYPE: DNA
<213> ORGANISM: Thalassiosira pseudonana

<400> SEQUENCE: 2

```
gttcaatgcc tttggtgttg tcgtcaatag gcacttcgac tttgctcttg gttccgttat      60
cccaaacttg aacgagcgcc acgtcctct cggtttcggt ggtatcccag gacctctcgt     120
agttgatgca gggttcagaa tcgagataac tcatgttgtc gtttgttgtt ttgttgattt     180
taccttgctt ccagctttcg gtctgtaatt acagtgacac gctgtactag aaatgatgta     240
cgtttgatgg aatctctaaa attatgagct atttatgaac acaggagttc tcatcaactt     300
tccatcgaaa tccgtaggag aattctaatg tcctcttcgg acgagagaca gacgtatcag     360
gagtcacttg aaggttccaa gattctatct tcatgaggtc tggatatgac agtcctgcct     420
tcgaggcaag ccctgtcact gtgacctttt cgcgtcgtca ataatttag gaacgcaagg     480
atagggattc tccatagtaa ggactattgt ttgaccctg aaacttcaac ctttacccca     540
agaatggggc attcataagt gaaaaacgtt tgttatgtat gccccaattc ctacacagga     600
ataggtattg aatcacgtag aaaatgatcg ttgcgccgca agcaaacaca ccggctctct     660
tccgccgcac tctcttccaa tccaacaaac aaacgcaacc                          700
```

<210> SEQ ID NO 3
<211> LENGTH: 700
<212> TYPE: DNA
<213> ORGANISM: Thalassiosira pseudonana

<400> SEQUENCE: 3

```
acgcagatag tgtatatttg cgtcacagtc tcttgtcgtc ataggagagg agaactagag     60
aacaaaaagc gtcatgtaat aaatgttgga tgttggcatg tcgtcccagc cagtatccaa    120
aacaccgaat tgtcgaggtt cgtgagcttg cagcactcat ggcaacggct aatttcatat    180
ctatgttatc aatgttatct gtaacactaa tgctaagtaa tgcgtcaaca acttatctcc    240
tccggctctt cactccactt cgctgacgtc gtttgatatt ttatctgctc tattattcaa    300
gttgaatctg cagttgaggc attctctaac ttagccgaga atcaagacg tgactttga     360
atttacaagt acagttacgc ttacacaaga tacctttctc acaaaaaaga ttccgttggc    420
tcccactgcg cattgctact tggtactatt cccatgtgga actggatttg ggggaaagag    480
ggagtctgag tttgtaaatg tacatttgtt attcccttca ttatcgacaa catcactaac    540
tcatcgtgca tacagagaaa aacaatctcc actttctcaa caaaagtggc cacaatgtgc    600
ctccgacaca gcctcaagag ccgaccgatc gttgcatttt tcactctcga acacacacac    660
acacacacac ccacacacca ccacctctct ttatccaacc                          700
```

<210> SEQ ID NO 4
<211> LENGTH: 779
<212> TYPE: DNA
<213> ORGANISM: Phaeodactylum tricornutum

<400> SEQUENCE: 4

```
agtcggattg aaaacagcga atgtacgcca ttccaaaggc gctcagcaaa aggagacata     60
tgcacacatc cagcggaagt aagtacgaca cttgaacaag agcatgacct gtcaaagcat    120
gctgccatcg tcgcttcgct tctattccca atgacacttt ggtcaccacg acttgaaaaa    180
cggcaatcag caaaataagc gatagaccct gaccaacggc agctttcatc ttttatgaac    240
ggcagatatt cgcatcctct tttatcgata cagcaaacac gcagaatttc tgttctcttt    300
caagacgaca agcacgaatt tcggtacgct gtcataattt attgactatg ttagataaca    360
caactctcat gcgctttgaa atctgctta cttcacagta agagacaag ctctttgcac     420
tgactgcgac agagatggaa aaaggaatt ctaccggcaa ttgacagact gatgtgaaaa    480
cagagagtaa ccgtaaacaa gtaccggtaa gtatgcgcgc aacctttact tgttccgttg    540
gcgtctgtca tttgatgtca cgcagacttg aaaagtcgtt cgctccattg tgaaaaatat    600
catgcgacaa cgttcagaaa ggccggcgtg caatcggttt gccttgtttc tgatccgctg    660
cttttgagc aacgacctgc ggaggaccac aatgatcttt ctcttgtcgt gagagctagt    720
tctattacct gttcaattac ctgctttctt gtattactcg aagctctcgt tcttctatc    779
```

<210> SEQ ID NO 5
<211> LENGTH: 807
<212> TYPE: DNA
<213> ORGANISM: Phaeodactylum tricornutum

<400> SEQUENCE: 5

```
ttttgtaatt cgccactacc tttacgcaag taagaacgtt tcatgctgga gtcgtggacc     60
aatcgtaagg tataccgttag tcataccgcg cctgtactat ttacgacacg agagaaagcc   120
actgcagttc tgggatggga tcagatgctt gctcctttca ctgcgctggc aaactgtatg    180
```

| | |
|---|---|
| ctagacacga ctcggatcgg atatcgaaat caaacggcgg agaatgggtt cggatgactg | 240 |
| tccggagcta cctaggaaaa gcttcttttt cgtttcggac caccaagagg gaagcgctgc | 300 |
| ctgtactcgt gcgataggaa gcatcagacg tatttgttcg gatgagatca caccagaact | 360 |
| agccaggcag ccagctagct attgtcatct acagatttcg aaccaaacgt ggatactaga | 420 |
| aagcatggga ttgactgtga ctgtgatttg tgttgcacac tttataccta ccctcgacct | 480 |
| cgtactttgt gtagtagcaa aatgtggatt gtgcgttgaa atgtagaagg gtttggggtt | 540 |
| gacacgggtt cattcatatc cgggtactcg aaaatgaccg caacgatact catcgatcga | 600 |
| gatacggtgt acacgtagac tacgtagaaa acctacgagg aagcagatat gattttccgg | 660 |
| tccgcagcat ccacccagcc aacgtcggca acaaccaaa caacctcgtc gccccttgtt | 720 |
| gttcaagatc tgcattccat tgacagcctt ttcaacgaaa ccgttcgctc gtttgattcc | 780 |
| atacgtcttt gaataccaac agaaaat | 807 |

<210> SEQ ID NO 6
<211> LENGTH: 791
<212> TYPE: DNA
<213> ORGANISM: Phaeodactylum tricornutum

<400> SEQUENCE: 6

| | |
|---|---|
| aaagtatcaa tagcttattc cagattttg tgatgttagc ctacttgtaa agcagcggag | 60 |
| gtctgtcatg acggtgtagt ggctggtttc gctccgaaaa ttaagttctg gttttatatc | 120 |
| tcaacataac tagagataaa gttacaggca cgttactgta agtccgcaga ttgctaatgc | 180 |
| tttgcttcgg tgtccgtaaa gcttatgtta ctgttctaga ttagagtggt atccacgatt | 240 |
| ttcaaacgaa agtgacatat tgcgaattgt gcagtatcag aaaatctcca agcaggagc | 300 |
| atacattagt ttggccgtat tgcaacgagt agctctcctg aagatgcaag taatagaggc | 360 |
| tgtgagcgtg aataatgaat ttgcctgttt agaagctggg gatcacatct cgtgctcccc | 420 |
| aaaagtctct cagtaaatca agaatgttcc tattttcgaa acattgcta tttatttagt | 480 |
| taaccggctt cgtcctccca tttaaataaa gattttcaaa aatgacacca ccaacgtccg | 540 |
| caagatcacg attcgagagg attcttcttt gtcccaacca tggatgacct ctcctattaa | 600 |
| cacgtatatg aagtaccgct gctggtaccc ggaaagaga ggacattcct tgtgggagag | 660 |
| tcatcgatgc gctgccaatc gaaaaaaatg ccaaggcgag aaaagcgcag ttcgttctta | 720 |
| taatccaatt ttgagtttca agacatactc gttgctacct tcccaccttc ccaaccaaac | 780 |
| cactcgcaac c | 791 |

<210> SEQ ID NO 7
<211> LENGTH: 1093
<212> TYPE: DNA
<213> ORGANISM: Artificial Sequence
<220> FEATURE:
<223> OTHER INFORMATION: Synthetic construct

<400> SEQUENCE: 7

| | |
|---|---|
| ccatggcgaa tggttctgca gtctctttga atctggaag cttgaatacg caggaggata | 60 |
| ctagttccag tccccctcct cggacgtttt tgcatcagct gcccgactgg agtcgcttgc | 120 |
| tgaccgccat cacaacagtg tttgtcaaat ctaaacgacc ggacatgcat gatcggaaaa | 180 |
| gcaagcgccc agatatgctc gtcgatagtt tcggactcga gtctactgtg caggacggcc | 240 |
| tggtgttccg tcaatccttc agcatccgaa gctacgagat tggtacggac cgtaccgcta | 300 |
| gcattgaaac gttgatgaac catctccaag aaaccagttt gaaccactgc aagagcacgg | 360 |

```
gcatcctgct ggatggtttt ggccgcacat tggaaatgtg caagcgagac ttgatctggg    420
tggtcattaa aatgcagatc aaagttaatc gatacccggc ctggggagat accgttgaga    480
tcaatacacg cttttcccgt ttgggcaaaa ttggcatggg tcgcgattgg ctgatctccg    540
actgcaacac cggtgagatc ttggtccgtg caacgtctgc gtacgcgatg atgaatcaaa    600
agacgcgtcg gttgagtaag ctgccgtatg aagttcacca agaaattgtt ccattgttcg    660
ttgatagtcc cgttatcgag gattctgacc tcaaagtcca caagtttaaa gtcaagactg    720
gcgattccat ccagaagggc ctgacgccag gttggaacga tctggatgtg aaccaacacg    780
ttagcaacgt taagtatatc ggctggatct tggaaagtat gcctacggaa gtcctggaga    840
cgcaggaact ctgcagtctc gctctggagt accgccgtga gtgtggccgt gattccgtgc    900
tcgagtccgt cactgcgatg gaccctagca aagtgggtgt tcgcagtcaa taccaacacc    960
tcttgcggct cgaagatggg accgccattg tgaacggcgc gaccgaatgg cgccccaaaa   1020
atgccggcgc taacggggca attagtaccg ggaaaacctc caatggaaac agcgtcagct   1080
aatgatagga tcc                                                      1093
```

<210> SEQ ID NO 8  
<211> LENGTH: 359  
<212> TYPE: PRT  
<213> ORGANISM: Artificial Sequence  
<220> FEATURE:  
<223> OTHER INFORMATION: Synthetic construct

<400> SEQUENCE: 8

```
Met Ala Asn Gly Ser Ala Val Ser Leu Lys Ser Gly Ser Leu Asn Thr
  1               5                  10                  15

Gln Glu Asp Thr Ser Ser Pro Pro Arg Thr Phe Leu His Gln
             20                  25                  30

Leu Pro Asp Trp Ser Arg Leu Leu Thr Ala Ile Thr Thr Val Phe Val
         35                  40                  45

Lys Ser Lys Arg Pro Asp Met His Asp Arg Lys Ser Lys Arg Pro Asp
     50                  55                  60

Met Leu Val Asp Ser Phe Gly Leu Glu Ser Thr Val Gln Asp Gly Leu
 65                  70                  75                  80

Val Phe Arg Gln Ser Phe Ser Ile Arg Ser Tyr Glu Ile Gly Thr Asp
                 85                  90                  95

Arg Thr Ala Ser Ile Glu Thr Leu Met Asn His Leu Gln Glu Thr Ser
            100                 105                 110

Leu Asn His Cys Lys Ser Thr Gly Ile Leu Leu Asp Gly Phe Gly Arg
        115                 120                 125

Thr Leu Glu Met Cys Lys Arg Asp Leu Ile Trp Val Val Ile Lys Met
    130                 135                 140

Gln Ile Lys Val Asn Arg Tyr Pro Ala Trp Gly Asp Thr Val Glu Ile
145                 150                 155                 160

Asn Thr Arg Phe Ser Arg Leu Gly Lys Ile Gly Met Gly Arg Asp Trp
                165                 170                 175

Leu Ile Ser Asp Cys Asn Thr Gly Glu Ile Leu Val Arg Ala Thr Ser
            180                 185                 190

Ala Tyr Ala Met Met Asn Gln Lys Thr Arg Arg Leu Ser Lys Leu Pro
        195                 200                 205

Tyr Glu Val His Gln Glu Ile Val Pro Leu Phe Val Asp Ser Pro Val
    210                 215                 220
```

Ile Glu Asp Ser Asp Leu Lys Val His Lys Phe Lys Val Lys Thr Gly
225                 230                 235                 240

Asp Ser Ile Gln Lys Gly Leu Thr Pro Gly Trp Asn Asp Leu Asp Val
            245                 250                 255

Asn Gln His Val Ser Asn Val Lys Tyr Ile Gly Trp Ile Leu Glu Ser
        260                 265                 270

Met Pro Thr Glu Val Leu Glu Thr Gln Glu Leu Cys Ser Leu Ala Leu
    275                 280                 285

Glu Tyr Arg Arg Glu Cys Gly Arg Asp Ser Val Leu Glu Ser Val Thr
290                 295                 300

Ala Met Asp Pro Ser Lys Val Gly Val Arg Ser Gln Tyr Gln His Leu
305                 310                 315                 320

Leu Arg Leu Glu Asp Gly Thr Ala Ile Val Asn Gly Ala Thr Glu Trp
            325                 330                 335

Arg Pro Lys Asn Ala Gly Ala Asn Gly Ala Ile Ser Thr Gly Lys Thr
        340                 345                 350

Ser Asn Gly Asn Ser Val Ser
        355

<210> SEQ ID NO 9
<211> LENGTH: 7259
<212> TYPE: DNA
<213> ORGANISM: Artificial Sequence
<220> FEATURE:
<223> OTHER INFORMATION: Synthetic construct

<400> SEQUENCE: 9
cgccggggct ggcagcttag tcctgcgcaa tctctactac atctgccaac ccagtgaaat      60
tttgatcttt gctggcagta gtcgccgcag tagtgatggc cgccgagttg gctatcgctt     120
ggtcaagggc ggcagcagcc tgcgggtacc tctgctggaa aaagcgctcc gcatggatct     180
gaccaacatg atcattgagt tgcgcgtttc caatgccttc tccaagggcg gcattcccct     240
gactgttgaa ggcgttgcca atatcaagat tgctgggaa gaaccgacca tccacaacgc     300
gatcgagcgg ctgcttggca aaaccgtaa ggaaatcgag caaattgcca aggagaccct     360
cgaaggcaac ttgcgtggtg ttttagccag cctcacgccg gagcagatca acgaggacaa     420
aattgccttt gccaaaagtc tgctggaaga ggcggaggat gaccttgagc agctgggtct     480
agtcctcgat acgctgcaag tccagaacat tccgatgag gtcggttatc tctcggctag     540
tggacgcaag cagcgggctg atctgcagcg agatgcccga attgctgaag ccgatgccca     600
ggctgcctct gcgatccaaa cggccgaaaa tgacaagatc acggccctgc gtcggatcga     660
tcgcgatgta gcgatcgccc aagccgaggc cgagcgccgg attcaggatg cgttgacgcg     720
gcgcgaagcg gtggtggccg aagctgaagc ggacattgct accgaagtcg ctcgtagcca     780
agcagaactc cctgtgcagc aggagcggat caaacaggtg cagcagcaac ttcaagccga     840
tgtgatcgcc ccagctgagg cagcttgtaa acgggcgatc gcggaagcgc gggggccgc     900 cgcccgtatc gtcgaagatg aaaagctca gcggaaggg acccaacggc tggcggaggc     960
ttggcagacc gctggtgcta atgcccgcga catcttcctg ctccagaagc tcgaaattcg    1020
agctcggtac catttacgtt gacaccatcg aatggtgcaa aacctttcgc ggtatggcat    1080
gatagcgccc ggaagagagt caattcaggg tggtgaatgt gaaaccagta acgttatacg    1140
atgtcgcaga gtatgccggt gtctcttatc agaccgtttc ccgcgtggtg aaccaggcca    1200
gccacgtttc tgcgaaaacg cgggaaaaag tggaagcggc gatggcggag ctgaattaca    1260

```
ttcccaaccg cgtggcacaa caactggcgg gcaaacagtc gttgctgatt ggcgttgcca    1320
cctccagtct ggccctgcac gcgccgtcgc aaattgtcgc ggcgattaaa tctcgcgccg    1380
atcaactggg tgccagcgtg gtggtgtcga tggtagaacg aagcggcgtc gaagcctgta    1440
aagcggcggt gcacaatctt ctcgcgcaac gcgtcagtgg gctgatcatt aactatccgc    1500
tggatgacca ggatgccatt gctgtggaag ctgcctgcac taatgttccg gcgttatttc    1560
ttgatgtctc tgaccagaca cccatcaaca gtattatttt ctcccatgaa gacgctacgc    1620
gactgggcgt ggagcatctg gtcgcattgg gtcaccagca aatcgcgctg ttagcgggcc    1680
cattaagttc tgtctcggcg cgtctgcgtc tggctggctg gcataaatat ctcactcgca    1740
atcaaattca gccgatagcg gaacgggaag gcgactggag tgccatgtcc ggttttcaac    1800
aaaccatgca aatgctgaat gagggcatcg ttcccactgc gatgctggtt gccaacgatc    1860
agatggcgct gggcgcaatg cgcgccatta ccgagtccgg gctgcgcgtt ggtgcggata    1920
tctcggtagt gggatacgac gataccgaag acagctcatg ttatatcccg ccgttaacca    1980
ccatcaaaca ggattttcgc ctgctggggc aaaccagcgt ggaccgcttg ctgcaactct    2040
ctcagggcca ggcggtgaag ggcaatcagc tgttgcccgt ctcactggtg aaaagaaaaa    2100
ccaccctggc gcccaatacg caaaccgcct ctccccgcgc gttggccgat tcattaatgc    2160
agctggcacg acaggtttcc cgactggaaa gcgggcagtg agcgcaacgc aattaatgta    2220
agttagcgcg aattgatctg gtttgacagc ttatcatcga ctgcacgtg caccaatgct    2280 tctggcgtca ggcagccatc ggaagctgtg gtatggctgt gcaggtcgta aatcactgca    2340
taattcgtgt cgctcaaggc gcactcccgt tctggataat gttttttgcg ccgacatcat    2400
aacggttctg gcaaatattc tgaaatgagc tgttgacaat taatcatccg gctcgtataa    2460
tgtgtggaat tgtgagcgga taacaatttc acacaggaaa cagcgccgct gagaaaaagc    2520
gaagcggcac tgctctttaa caatttatca gacaatctgt gtgggcactc gaccggaatt    2580
atcgattaac tttattatta aaaattaaag aggtatatat taatgtatcg attaaataag    2640
gaggaataaa ccatggcgaa tggttctgca gtctctttga aatctggaag cttgaatacg    2700
caggaggata ctagttccag tccccctcct cggacgtttt tgcatcagct gcccgactgg    2760
agtcgcttgc tgaccgccat cacaacagtg tttgtcaaat ctaaacgacc ggacatgcat    2820
gatcggaaaa gcaagcgccc agatatgctc gtcgatagtt tcggactcga gtctactgtg    2880
caggacggcc tggtgttccg tcaatccttc agcatccgaa gctacgagat tggtacggac    2940
cgtaccgcta gcattgaaac gttgatgaac catctccaag aaaccagttt gaaccactgc    3000
aagagcacgg gcatcctgct ggatggtttt ggccgcacat tggaaatgtg caagcgagac    3060
ttgatctggg tggtcattaa aatgcagatc aaagttaatc gatacccggc tggggagat    3120 accgttgaga tcaatacacg cttttcccgt ttgggcaaaa ttggcatggg tcgcgattgg    3180
ctgatctccg actgcaacac cggtgagatc ttggtccgtg caacgtctgc gtacgcgatg    3240
atgaatcaaa agacgcgtcg gttgagtaag ctgccgtatg aagttcacca agaaattgtt    3300
ccattgttcg ttgatagtcc cgttatcgag gattctgacc tcaaagtcca caagtttaaa    3360
gtcaagactg gcgattccat ccagaagggc ctgacgccag gttggaacga tctggatgtg    3420
aaccaacacg ttagcaacgt taagtatatc ggctggatct tggaaagtat gcctacggaa    3480
gtcctggaga cgcaggaact ctgcagtctc gctctggagt accgccgtga gtgtggccgt    3540
gattccgtgc tcgagtccgt cactgcgatg gaccctagca aagtgggtgt tcgcagtcaa    3600
taccaacacc tcttgcgggct cgaagatggg accgccattg tgaacggcgc gaccgaatgg    3660
```

```
cgccccaaaa atgccggcgc taacggggca attagtaccg ggaaaacctc caatggaaac    3720
agcgtcagct aatgatagga tccgagctcg agatctgcag ctggtaccat atgggaattc    3780
gaagcttggc tgttttggcg gatgagagaa gattttcagc ctgatacaga ttaaatcaga    3840
acgcagaagc ggtctgataa aacagaattt gcctggcggc agtagcgcgg tggtcccacc    3900
tgaccccatg ccgaactcag aagtgaaacg ccgtagcgcc gatggtagtg tggggtctcc    3960
ccatgcgaga gtagggaact gccaggcatc aaataaaacg aaaggctcag tcgaaagact    4020
gggcctttcg ttttatctgt tgtttgtcgg tgaacgctct cctgagtagg acaaatccgc    4080
cgggagcgga tttgaacgtt gcgaagcaac ggcccgagg gtggcgggca ggacgcccgc    4140
cataaactgc caggcatcaa attaagcaga aggccatcct gacggatggc cttttgcgt    4200 ttctacaaac tcttttgttt attttttctaa atacattcaa atatgtatcc gctcatgggg    4260
atccgactag taggcctcga ggaattcacg cgtacgtaga tctccgcggc cgccgatcct    4320
ctagtatgct tgtaaaccgt tttgtgaaaa aattttttaaa ataaaaaagg ggacctctag    4380
ggtccccaat taattagtaa tataatctat taaaggtcat tcaaaaggtc atccaccgga    4440
tcagcttagt aaagccctcg ctagatttta atgcggatgt tgcgattact cgccaacta    4500 ttgcgataac aagaaaaagc cagccttca tgatatatct cccaatttgt gtagggctta    4560
ttatgcacgc ttaaaaataa taaaagcaga cttgacctga tagtttggct gtgagcaatt    4620
atgtgcttag tgcatctaac gcttgagtta agccgcgccg cgaagcggcg tcggcttgaa    4680
cgaattgtta gacattattt gccgactacc ttggtgatct cgcctttcac gtagtggaca    4740
aattcttcca actgatctgc gcgcgaggcc aagcgatctt cttcttgtcc aagataagcc    4800
tgtctagctt caagtatgac gggctgatac tgggccggca ggcgctccat tgcccagtcg    4860
gcagcgacat ccttcggcgc gattttgccg gttactgcgc tgtaccaaat gcgggacaac    4920
gtaagcacta catttcgctc atcgccagcc cagtcgggcg cgagttcca tagcgttaag    4980 gtttcattta gcgcctcaaa tagatcctgt tcaggaaccg gatcaaagag ttcctccgcc    5040
gctggaccta ccaaggcaac gctatgttct cttgcttttg tcagcaagat agccagatca    5100
atgtcgatcg tggctggctc gaagatacct gcaagaatgt cattgcgctg ccattctcca    5160
aattgcagtt cgcgcttagc tggataacgc cacggaatga tgtcgtcgtg cacaacaatg    5220
gtgacttcta cagcgcggag aatctcgctc tctccagggg aagccgaagt ttccaaaagg    5280
tcgttgatca aagctcgccg cgttgtttca tcaagcctta cggtcaccgt aaccagcaaa    5340
tcaatatcac tgtgtggctt caggccgcca tccactgcgg agccgtacaa atgtacggcc    5400
agcaacgtcg gttcgagatg cgctcgatg acgccaacta cctctgatag ttgagtcgat    5460
acttcggcga tcaccgcttc cctcatgatg tttaactttg ttttagggcg actgccctgc    5520
tgcgtaacat cgttgctgct ccataacatc aaacatcgac ccacggcgta acgcgcttgc    5580
tgcttggatg cccgaggcat agactgtacc ccaaaaaaac agtcataaca agccatgaaa    5640
accgccactg cgccgttacc accgctgcgt tcggtcaagg ttctggacca gttgcgtgag    5700
cgcatacgct acttgcatta cagcttacga accgaacagg cttatgtcca ctgggttcgt    5760
gccttcatcc gtttccacgg tgtgcgtcac ccggcaacct tgggcagcag cgaagtcgag    5820
gcatttctgt cctggctggc gaacgagcgc aaggtttcgg tctccacgca tcgtcaggca    5880
ttggcggcct tgctgttctt ctacggcaag gtgctgtgca cggatctgcc ctggcttcag    5940
gagatcggaa gacctcggcc gtcgcggcgc ttgccggtgg tgctgacccc ggatgaagtg    6000
```

```
gttcgcatcc tcggttttct ggaaggcgag catcgtttgt tcgcccagct tctgtatgga    6060
acgggcatgc ggatcagtga gggttttgcaa ctgcgggtca aggatctgga tttcgatcac    6120
ggcacgatca tcgtgcggga gggcaagggc tccaaggatc gggccttgat gttacccgag    6180
agcttggcac ccagcctgcg cgagcagggg aattgatccg gtggatgacc ttttgaatga    6240
cctttaatag attatattac taattaattg gggaccctag aggtccccct ttttatttta    6300 aaaattttt cacaaaacgg tttacaagca taaagctcta gagtcgacct gcaggcatgc    6360
aagcttcgag tccctgctcg tcacgctttc aggcaccgtg ccagatatcg acgtggagtc    6420
gatcactgtg attggcgaag gggaaggcag cgctacccaa atcgctagct tgctggagaa    6480
gctgaaacaa accacgggca ttgatctggc gaaatcccta ccgggtcaat ccgactcgcc    6540
cgctgcgaag tcctaagaga tagcgatgtg accgcgatcg cttgtcaaga atcccagtga    6600
tcccgaacca taggaaggca agctcaatgc ttgcctcgtc ttgaggacta tctagatgtc    6660
tgtggaacgc acatttattg ccatcaagcc cgatggcgtt cagcggggtt tggtcggtac    6720
gatcatcggc cgctttgagc aaaaaggctt caaactggtg ggcctaaagc agctgaagcc    6780
cagtcgcgag ctggccgaac agcactatgc tgtccaccgc gagcgcccct tcttcaatgg    6840
cctcgtcgag ttcatcacct ctgggccgat cgtggcgatc gtcttggaag gcgaaggcgt    6900
tgtggcggct gctcgcaagt tgatcggcgc taccaatccg ctgacggcag aaccgggcac    6960
catccgtggt gattttggtg tcaatattgg ccgcaacatc atccatggct cggatgcaat    7020
cgaaacagca caacaggaaa ttgctctctg gtttagccca gcagagctaa gtgattggac    7080
ccccacgatt caaccctggc tgtacgaata aggtctgcat tccttcagag agacattgcc    7140
atgcccgtgc tgcgatcgcc cttccaagct gccttgcccc gctgtttcgg gctggcagcc    7200
ctggcgttgg ggctggcgac cgcttgccaa gaaagcagcg ctccgccggc tgccggatc    7259

<210> SEQ ID NO 10
<211> LENGTH: 7113
<212> TYPE: DNA
<213> ORGANISM: Artificial Sequence
<220> FEATURE:
<223> OTHER INFORMATION: Synthetic construct

<400> SEQUENCE: 10
cgccggggct ggcagcttag tcctgcgcaa tctctactac atctgccaac ccagtgaaat      60
tttgatcttt gctggcagta gtcgccgcag tagtgatggc cgccgagttg ctatcgcttt     120
ggtcaagggc ggcagcagcc tgcgggtacc tctgctggaa aaagcgctcc gcatggatct     180
gaccaacatg atcattgagt tgcgcgtttc caatgccttc tccaagggcg gcattcccct     240
gactgttgaa ggcgttgcca atatcaagat tgctggggaa gaaccgacca tccacaacgc     300
gatcgagcgg ctgcttggca aaaaccgtaa ggaaatcgag caaattgcca aggagaccct     360
cgaaggcaac ttgcgtggtg ttttagccag cctcacgccg gagcagatca acgaggacaa     420
aattgccttt gccaaaagtc tgctggaaga ggcgaggat gaccttgagc agctgggtct     480
agtcctcgat acgctgcaag tccagaacat ttccgatgag gtcggttatc tctcggctag     540
tggacgcaag cagcgggctg atctgcagcg agatgcccga attgctgaag ccgatgccca     600
ggctgcctct gcgatccaaa cggccgaaaa tgacaagatc acggccctgc gtcggatcga     660
tcgcgatgta gcgatcgccc aagccgaggc cgagcgccgg attcaggatg cgttgacgcg     720
gcgcgaagcg gtggtggccg aagctgaagc ggacattgct accgaagtcg ctcgtagcca     780
agcagaactc cctgtgcagc aggagcggat caaacaggtg cagcagcaac ttcaagccga     840
```

```
tgtgatcgcc ccagctgagg cagcttgtaa acgggcgatc gcggaagcgc ggggggccgc    900
cgcccgtatc gtcgaagatg gaaaagctca agcggaaggg acccaacggc tggcggaggc    960
ttggcagacc gctggtgcta atgcccgcga catcttcctg ctccagaagc tcgaaattcg   1020
agctcggtac catttacgtt gacaccatcg aatggtgcaa aacctttcgc ggtatggcat   1080
gatagcgccc ggaagagagt caattcaggg tggtgaatgt gaaaccagta acgttatacg   1140
atgtcgcaga gtatgccggt gtctcttatc agaccgtttc ccgcgtggtg aaccaggcca   1200
gccacgtttc tgcgaaaacg cgggaaaaag tggaagcggc gatggcggag ctgaattaca   1260
ttcccaaccg cgtggcacaa caactggcgg gcaaacagtc gttgctgatt ggcgttgcca   1320
cctccagtct ggccctgcac gcgccgtcgc aaattgtcgc ggcgattaaa tctcgcgccg   1380
atcaactggg tgccagcgtg gtggtgtcga tggtagaacg aagcggcgtc gaagcctgta   1440
aagcggcggt gcacaatctt ctcgcgcaac gcgtcagtgg gctgatcatt aactatccgc   1500
tggatgacca ggatgccatt gctgtggaag ctgcctgcac taatgttccg gcgttatttc   1560
ttgatgtctc tgaccagaca cccatcaaca gtattatttt ctcccatgaa gacggtacgc   1620
gactgggcgt ggagcatctg gtcgcattgg gtcaccagca atcgcgctg ttagcgggcc    1680 cattaagttc tgtctcggcg cgtctgcgtc tggctggctg cataaatat ctcactcgca    1740 atcaaattca gccgatagcg gaacgggaag gcgactggag tgccatgtcc ggttttcaac   1800
aaaccatgca aatgctgaat gagggcatcg ttcccactgc gatgctggtt gccaacgatc   1860
agatggcgct gggcgcaatg cgcgccatta ccgagtccgg gctgcgcgtt ggtgcggata   1920
tctcggtagt gggatacgac gataccgaag acagctcatg ttatatcccg ccgttaacca   1980
ccatcaaaca ggattttcgc ctgctggggc aaaccagcgt ggaccgcttg ctgcaactct   2040
ctcagggcca ggcggtgaag ggcaatcagc tgttgcccgt ctcactggtg aaaagaaaaa   2100
ccaccctggc gcccaatacg caaaccgcct ctccccgcgc gttggccgat tcattaatgc   2160
agctggcacg acaggtttcc cgactggaaa gcgggcagtg agcgcaacgc aattaatgta   2220
agttagcgcg aattgatctg gtttgacagc ttatcatcga ctgcacggtg caccaatgct   2280
tctggcgtca ggcagccatc ggaagctgtg gtatggctgt gcaggtcgta atcactgca    2340 taattcgtgt cgctcaaggc gcactcccgt tctggataat gttttttgcg ccgacatcat   2400 aacggtctg gcaaatattc tgaaatgagc tgttgacaat taatcatccg gctcgtataa    2460
tgtgtggaat tgtgagcgga taacaatttc acacaggaaa cagaccatgg cgaatggttc   2520
tgcagtctct ttgaaatctg gaagcttgaa tacgcaggag gatactagtt ccagtccccc   2580
tcctcggacg tttttgcatc agctgcccga ctggagtcgc ttgctgaccg ccatcacaac   2640
agtgtttgtc aaatctaaac gaccggacat gcatgatcgg aaaagcaagc gcccagatat   2700
gctcgtcgat agtttcggac tcgagtctac tgtgcaggac ggcctggtgt ccgtcaatc    2760 cttcagcatc cgaagctacg agattggtac ggaccgtacc gctagcattg aaacgttgat   2820
gaaccatctc caagaaacca gtttgaacca ctgcaagagc acgggcatcc tgctggatgg   2880
ttttggccgc acattggaaa tgtgcaagcg agacttgatc tgggtggtca ttaaaatgca   2940
gatcaaagtt aatcgatacc cggcctgggg agataccgtt gagatcaata cacgcttttc   3000
ccgtttgggc aaaattggca tgggtcgcga ttggctgatc tccgactgca cacoggtga    3060 gatcttggtc cgtgcaacgt ctgcgtacgc gatgatgaat caaaagacgc gtcggttgag   3120
taagctgccg tatgaagttc accaagaaat tgttccattg ttcgttgata gtcccgttat   3180
```

```
cgaggattct gacctcaaag tccacaagtt taaagtcaag actggcgatt ccatccagaa    3240
gggcctgacg ccaggttgga acgatctgga tgtgaaccaa cacgttagca acgttaagta    3300
tatcggctgg atcttggaaa gtatgcctac ggaagtcctg gagacgcagg aactctgcag    3360
tctcgctctg gagtaccgcc gtgagtgtgg ccgtgattcc gtgctcgagt ccgtcactgc    3420
gatggaccct agcaaagtgg gtgttcgcag tcaataccaa cacctcttgc ggctcgaaga    3480
tgggaccgcc attgtgaacg cgcgaccga atggcgcccc aaaaatgccg cgctaacgg      3540
ggcaattagt accgggaaaa cctccaatgg aaacagcgtc agctaatgat aggatccgag    3600
ctcgagatct gcagctggta ccatatggga attcgaagct tggctgtttt ggcggatgag    3660
agaagatttt cagcctgata cagattaaat cagaacgcag aagcggtctg ataaaacaga    3720
atttgcctgg cggcagtagc gcggtggtcc cacctgaccc catgccgaac tcagaagtga    3780
aacgccgtag cgccgatggt agtgtggggt ctccccatgc gagagtaggg aactgccagg    3840
catcaaataa aacgaaaggc tcagtcgaaa gactgggcct ttcgttttat ctgttgtttg    3900
tcggtgaacg ctctcctgag taggacaaat ccgccgggag cggatttgaa cgttgcgaag    3960
caacggcccg gagggtggcg ggcaggacgc ccgccataaa ctgccaggca tcaaattaag    4020
cagaaggcca tcctgacgga tggccttttt gcgtttctac aaactctttt gtttattttt    4080
ctaaatacat tcaaatatgt atccgctcat ggggatccga ctagtaggcc tcgaggaatt    4140
cacgcgtacg tagatctccg cggccgccga tcctctagta tgcttgtaaa ccgttttgtg    4200
aaaaaatttt taaaataaaa aaggggacct ctagggtccc caattaatta gtaatataat    4260
ctattaaagg tcattcaaaa ggtcatccac cggatcagct tagtaaagcc ctcgctagat    4320
tttaatgcgg atgttgcgat tacttcgcca actattgcga taacaagaaa aagccagcct    4380
ttcatgatat atctcccaat ttgtgtaggg cttattatgc acgcttaaaa ataataaaag    4440
cagacttgac ctgatagttt ggctgtgagc aattatgtgc ttagtgcatc taacgcttga    4500
gttaagccgc gccgcgaagc ggcgtcggct tgaacgaatt gttagacatt atttgccgac    4560
taccttggtg atctcgcctt tcacgtagtg gacaaattct tccaactgat ctgcgcgcga    4620
ggccaagcga tcttcttctt gtccaagata agcctgtcta gcttcaagta tgacgggctg    4680
atactgggcc ggcaggcgct ccattgccca gtcggcagcg acatccttcg gcgcgatttt    4740
gccggttact gcgctgtacc aaatgcggga caacgtaagc actacatttc gctcatcgcc    4800
agcccagtcg gcggcgagt tccatagcgt taaggtttca tttagcgcct caaatagatc      4860
ctgttcagga accggatcaa agagttcctc cgccgctgga cctaccaagg caacgctatg    4920
ttctcttgct tttgtcagca agatagccag atcaatgtcg atcgtggctg gctcgaagat    4980
acctgcaaga atgtcattgc gctgccattc tccaaattgc agttcgcgct tagctggata    5040
acgccacgga atgatgtcgt cgtgcacaac aatggtgact tctacagcgc ggagaatctc    5100
gctctctcca ggggaagccg aagtttccaa aaggtcgttg atcaaagctc gccgcgttgt    5160
ttcatcaagc cttacggtca ccgtaaccag caaatcaata tcactgtgtg gcttcaggcc    5220
gccatccact gcggagccgt acaaatgtac ggccagcaac gtcggttcga tggcgctc      5280
gatgacgcca actacctctg atagttgagt cgatacttcg gcgatcaccg cttccctcat    5340
gatgtttaac tttgttttag ggcgactgcc ctgctgcgta acatcgttgc tgctccataa    5400
catcaaacat cgacccacgg cgtaacgcgc ttgctgcttg gatgcccgag gcatagactg    5460
taccccaaaa aaacagtcat aacaagccat gaaaaccgcc actgcgccgt taccaccgct    5520
gcgttcggtc aaggttctgg accagttgcg tgagcgcata cgctacttgc attacagctt    5580
```

-continued

```
acgaaccgaa caggcttatg tccactgggt tcgtgccttc atccgttttcc acggtgtgcg      5640 tcacccggca accttgggca gcagcgaagt cgaggcattt ctgtcctggc tggcgaacga      5700
gcgcaaggtt tcggtctcca cgcatcgtca ggcattggcg gccttgctgt tcttctacgg      5760
caaggtgctg tgcacggatc tgccctggct tcaggagatc ggaagacctc ggccgtcgcg      5820
gcgcttgccg gtggtgctga ccccggatga agtggttcgc atcctcggtt ttctggaagg      5880
cgagcatcgt ttgttcgccc agcttctgta tggaacgggc atgcggatca gtgagggttt      5940
gcaactgcgg gtcaaggatc tggatttcga tcacggcacg atcatcgtgc gggagggcaa      6000
gggctccaag gatcgggcct tgatgttacc cgagagcttg gcacccagcc tgcgcgagca      6060
ggggaattga tccggtggat gacctttgta atgacctttta atagattata ttactaatta      6120
attggggacc ctagaggtcc cctttttttat tttaaaaatt ttttcacaaa acggtttaca      6180
agcataaagc tctagagtcg acctgcaggc atgcaagctt cgagtccctg ctcgtcacgc      6240
tttcaggcac cgtgccagat atcgacgtgg agtcgatcac tgtgattggc gaaggggaag      6300
gcagcgctac ccaaatcgct agcttgctgg agaagctgaa acaaaccacg ggcattgatc      6360
tggcgaaatc cctaccgggt caatccgact cgcccgctgc gaagtcctaa gagatagcga      6420
tgtgaccgcg atcgcttgtc aagaatccca gtgatcccga accataggaa ggcaagctca      6480
atgcttgcct cgtcttgagg actatctaga tgtctgtgga acgcacattt attgccatca      6540
agcccgatgg cgttcagcgg ggtttggtcg gtacgatcat cggccgcttt gagcaaaaag      6600
gcttcaaact ggtgggccta agcagctga agcccagtcg cgagctggcc gaacagcact      6660
atgctgtcca ccgcgagcgc cccttcttca atggcctcgt cgagttcatc acctctgggc      6720
cgatcgtggc gatcgtcttg gaaggcgaag gcgttgtggc ggctgctcgc aagttgatcg      6780
gcgctaccaa tccgctgacg gcagaaccgg gcaccatccg tggtgatttt ggtgtcaata      6840
ttggccgcaa catcatccat ggctcggatg caatcgaaac agcacaacag gaaattgctc      6900
tctggtttag cccagcagag ctaagtgatt ggaccccccac gattcaaccc tggctgtacg      6960
aataaggtct gcattccttc agagagacat tgccatgccc gtgctgcgat cgcccttcca      7020
agctgccttg ccccgctgtt tcgggctggc agccctggcg ttggggctgg cgaccgcttg      7080
ccaagaaagc agcgctccgc cggctgccgg atc                                  7113
```

<210> SEQ ID NO 11
<211> LENGTH: 7173
<212> TYPE: DNA
<213> ORGANISM: Artificial Sequence
<220> FEATURE:
<223> OTHER INFORMATION: Synthetic construct

<400> SEQUENCE: 11

```
cttccgcttc ctcgctcact gactcgctgc gctcggtcgt tcggctgcgg cgagcggtat       60
cagctcactc aaaggcggta atacggttat ccacagaatc aggggataac gcaggaaaga      120
acatgtgagc aaaaggccag caaaaggcca ggaaccgtaa aaaggccgcg ttgctggcgt      180
ttttccatag gctccgcccc cctgacgagc atcacaaaaa tcgacgctca agtcagaggt      240
ggcgaaaccc gacaggacta taaagatacc aggcgtttcc ccctggaagc tccctcgtgc      300
gctctcctgt tccgaccctg ccgcttaccg gatacctgtc cgcctttctc ccttcgggaa      360
gcgtggcgct ttctcatagc tcacgctgta ggtatctcag ttcggtgtag tcgttcgct      420 ccaagctggg ctgtgtgcac gaacccccccg ttcagcccga ccgctgcgcc ttatccggta      480
```

-continued

```
actatcgtct tgagtccaac ccggtaagac acgacttatc gccactggca gcagccactg    540
gtaacaggat tagcagagcg aggtatgtag gcggtgctac agagttcttg aagtggtggc    600
ctaactacgg ctacactaga aggacagtat ttggtatctg cgctctgctg aagccagtta    660
ccttcggaaa aagagttggt agctcttgat ccggcaaaca aaccaccgct ggtagcggtg    720
gtttttttgt ttgcaagcag cagattacgc gcagaaaaaa aggatctcaa gaagatcctt    780
tgatcttttc tacggggtct gacgctcagt ggaacgaaaa ctcacgttaa gggattttgg    840
tcatgagatt atcaaaaagg atcttcacct agatcctttt aaattaaaaa tgaagtttta    900
aatcaatcta agtatatat gagtaaactt ggtctgacag ttaccaatgc ttaatcagtg    960
aggcacctat ctcagcgatc tgtctatttc gttcatccat agttgcctga ctccccgtcg   1020
tgtagataac tacgatacgg gagggcttac catctggccc cagtgctgca atgataccgc   1080
gagacccacg ctcaccggct ccagatttat cagcaataaa ccagccagcc ggaagggccg   1140
agcgcagaag tggtcctgca actttatccg cctccatcca gtctattaat tgttgccggg   1200
aagctagagt aagtagttcg ccagttaata gtttgcgcaa cgttgttgcc attgctacag   1260
gcatcgtggt gtcacgctcg tcgtttggta tggcttcatt cagctccggt tcccaacgat   1320
caaggcgagt tacatgatcc cccatgttgt gcaaaaaagc ggttagctcc ttcggtcctc   1380
cgatcgttgt cagaagtaag ttggccgcag tgttatcact catggttatg gcagcactgc   1440
ataattctct tactgtcatg ccatccgtaa gatgcttttc tgtgactggt gagtactcaa   1500
ccaagtcatt ctgagaatag tgtatgcggc gaccgagttg ctcttgcccg gcgtcaatac   1560
gggataatac cgcgccacat agcagaactt taaaagtgct catcattgga aaacgttctt   1620
cggggcgaaa actctcaagg atcttaccgc tgttgagatc cagttcgatg taacccactc   1680
gtgcacccaa ctgatcttca gcatctttta ctttcaccag cgtttctggg tgagcaaaaa   1740
caggaaggca aaatgccgca aaaaagggaa taagggcgac acggaaatgt tgaatactca   1800
tactcttcct ttttcaatat tattgaagca tttatcaggg ttattgtctc atgagcggat   1860
acatatttga atgtatttag aaaaataaac aaataggggt tccgcgcaca tttccccgaa   1920
aagtgccacc tgacgtctaa gaaaccatta ttatcatgac attaacctat aaaaataggc   1980
gtatcacgag gccctttcgt ctcgcgcgtt tcggtgatga cggtgaaaac ctctgacaca   2040
tgcagctccc ggagacggtc acagcttgtc tgtaagcgga tgccgggagc agacaagccc   2100
gtcagggcgc gtcagcgggt gttggcgggt gtcggggctg gcttaactat gcggcatcag   2160
agcagattgt actgagagtg caccataaaa ttgtaaacgt taatattttg ttaaaattcg   2220
cgttaaattt ttgttaaatc agctcatttt ttaaccaata ggccgaaatc ggcaaaatcc   2280
cttataaatc aaaagaatag cccgagatag ggttgagtgt tgttccagtt tggaacaaga   2340
gtccactatt aaagaacgtg gactccaacg tcaagggcg aaaaaccgtc tatcagggcg    2400
atggcccact acgtgaacca tcacccaaat caagtttttt ggggtcgagg tgccgtaaag   2460
cactaaatcg gaaccctaaa gggagccccc gatttagagc ttgacgggga agcggcga    2520
acgtggcgag aaaggaaggg aagaaagcga aggagcgggc gctagggcg ctggcaagtg    2580
tagcggtcac gctgcgcgta accaccacac ccgccgcgct taatgcgccg ctacagggcg   2640
cgtactatgg ttgctttgac gtatgcggtg tgaaataccg cacagatgcg taaggagaaa   2700
ataccgcatc aggcgccatt cgccattcag gctgcgcaac tgttgggaag ggcgatcggt   2760
gcgggcctct tcgctattac gccagctggc gaaagggga tgtgctgcaa ggcgattaag   2820
ttgggtaacg ccagggtttt cccagtcacg acgttgtaaa acgacggcca gtgccaagct   2880
```

```
attgctgaag cggaatccct ggttaatgcc gccgccgatg ccaattgcat tctccaagtg    2940
gggcacattg aacgcttcaa cccggcattt ttagagctaa ccaaaattct caaaacggaa    3000
gagttattgg cgatcgaagc ccatcgcatg agtccctatt cccagcgggc caatgatgtc    3060
tccgtggtat tggatttgat gatccatgac attgacctgt tgctggaatt ggtgggttcg    3120
gaagtggtta aactgtccgc cagtggcagt cgggcttctg ggtcaggata tttggattat    3180
gtcaccgcta cgttaggctt ctcctccggc attgtggcca ccctcaccgc cagtaaggtc    3240
acccatcgta aaattcgttc catcgccgcc cactgcaaaa attccctcac cgaagcggat    3300
tttctcaata cgaaatttt gatccatcgc caaaccaccg ctgattggag cgcggactat    3360
ggccaggtat tgtatcgcca ggatggtcta atcgaaaagg tttacaccag taatattgaa    3420
cctctccacg ctgaattaga acatttattt cattgtgtta ggggaggtga tcaaccctca    3480 gtgggggggag aacaggccct caaggccctg aagttagcca gtttaattga agaaatggcc    3540
ctggacagtc aggaatggca tggggggggaa gttgtgacag aatatcaaga tgccaccctg    3600
gccctcagtg cgagtgttta aatcaactta attaatgcaa ttattgcgag ttcaaactcg    3660
ataactttgt gaaatattac tgttaatta atctatgact attcaataca ccccctagc    3720 cgatcgcctg ttggcctacc tcgccgccga tcgcctaaat ctcagcgcca agagtagttc    3780
cctcaacacc agtattctgc tcagcagtga cctattcaat caggaagggg gaattgtaac    3840
agccaactat ggctttgatg gttatatggt accatatgca tgcgagctca gatctaccag    3900
gttgtccttg cgcagcgct tcccacgctg agagggtgta gcccgtcacg ggtaaccgat    3960
atcgtcgaca ggcctctaga cccgggctcg agctagcaag cttggccgga tccggccgga    4020
tccggagttt gtagaaacgc aaaaaggcca tccgtcagga tggccttctg cttaatttga    4080
tgcctggcag tttatggcgg gcgtcctgcc cgccaccctc cgggccgttg ctccgcaacg    4140
ttcaaatccg ctcccggcgg atttgtccta ctcaggagag cgttcaccga caaacaacag    4200
ataaaacgaa aggcccagtc tttcgactga gcctttcgtt ttatttgatg cctggcagtt    4260
ccctactctc gcatgggag accccacact accatcggcg ctacggcgtt tcacttctga    4320
gttcggcatg gggtcaggtg gaccaccgc gctactgccg ccaggcaaat tctgttttat    4380
tgagccgtta ccccacctac tagctaatcc catctgggca catccgatgg caagaggccc    4440
gaaggtcccc ctctttggtc ttgcgacgtt atgcggtatt agctaccgtt tccagtagtt    4500 atcccctcc atcaggcagt ttcccagaca ttactcaccc gtccgccact cgtcagcaaa    4560
gaagcaagct tagatcgacc tgcagggggg gggggaaag ccacgttgtg tctcaaaatc    4620
tctgatgtta cattgcacaa gataaaata tatcatcatg aacaataaaa ctgtctgctt    4680
acataaacag taatacaagg ggtgttatga gccatattca acgggaaacg tcttgctcga    4740
ggccgcgatt aaattccaac atggatgctg attatatgg gtataaatgg gctcgcgata    4800
atgtcgggca atcaggtgcg acaatctatc gattgtatgg gaagcccgat gcgccagagt    4860
tgtttctgaa acatggcaaa ggtagcgttg ccaatgatgt tacagatgag atggtcagac    4920
taaactggct gacggaattt atgcctcttc cgaccatcaa gcattttatc cgtactcctg    4980
atgatgcatg gttactcacc actgcgatcc ccggaaaaac agcattccag gtattagaag    5040
aatatcctga ttcaggtgaa aatattgttg atgcgctggc agtgttcctg cgccggttgc    5100
attcgattcc tgtttgtaat tgtccttta acagcgatcg cgtatttcgt ctcgctcagg    5160
cgcaatcacg aatgaataac ggtttggttg atgcgagtga ttttgatgac gagcgtaatg    5220
```

```
gctggcctgt tgaacaagtc tggaaagaaa tgcataagct tttgccattc tcaccggatt    5280
cagtcgtcac tcatggtgat ttctcacttg ataaccttat ttttgacgag gggaaattaa    5340
taggttgtat tgatgttgga cgagtcggaa tcgcagaccg ataccaggat cttgccatcc    5400
tatggaactg cctcggtgag ttttctcctt cattacagaa acggcttttt caaaaatatg    5460
gtattgataa tcctgatatg aataaattgc agtttcattt gatgctcgat gagttttcct    5520
aatcagaatt ggttaattgg ttgtaacact ggcagagcat tacgctgact tgacgggacg    5580
gcggctttgt tgaataaatc gaacttttgc tgagttgaag gatcagatca cgcatcttcc    5640
cgacaacgca gaccgttccg tggcaaagca aaagttcaaa atcaccaact ggtccaccta    5700
caacaaagct ctcatcaacc gtggctccct cactttctgg ctggatgatg gggcgattca    5760
ggcctggtat gagtcagcaa caccttcttc acgaggcaga cctcagcgcc cccccccccc    5820
tgcaggtcga tctggtaacc ccagcgcggt tgctaccaag tagtgacccg cttcgtgatg    5880
caaaatccgc tgacgatatt cgggcgatcg ctgctgaatg ccatcgagca gtaacgtggc    5940
gaattcggta ccggtatgga tggcaccgat gcggaatccc aacagattgc ctttgacaac    6000
aatgtggcct ggaataacct gggggatttg tccaccacca cccaacgggc ctacacttcg    6060
gctattagca cagacacagt gcagagtgtt tatggcgtta atctgaaaaa aaacgataac    6120
attcccattg tttttgcgtg gcccattttt cccaccaccc ttaatcccac agattttcag    6180
gtaatgctta acacggggga aattgtcacc ccggtgatcg cctctttgat tcccaacagt    6240
gaatacaacg aacggcaaac ggtagtaatt acgggcaatt ttggtaatcg tttaaccccca   6300 ggcacggagg gagcgattta tcccgtttcc gtaggcacag tgttggacag tactccttttg   6360 gaaatggtgg gacccaacgg cccggtcagt gcggtgggta ttaccattga tagtctcaac    6420
ccctacgtgg ccggcaatgg tcccaaaatt gtcgccgcta agttagaccg cttcagtgac    6480 ctggggaag gggctcccct ctggttagcc accaatcaaa ataacagtgg cggggattta    6540
tatggagacc aagcccaatt tcgtttgcga atttacacca cgccggtttt tccccccgat    6600
ggcattgcca gtttactacc cacagaattt gaacggtatt ttcaactcca gcggaagat    6660 attacgggac ggacagttat cctaacccaa actggtgttg attatgaaat tcccggcttt    6720
ggtctggtgc aggtgttggg gctggcggat ttggccgggg ttcaggacag ctatgacctg    6780
acttacatcg aagatcatga caactattac gacattatcc tcaaagggga cgaagccgca    6840
gttcgccaaa ttaagagggt tgctttgccc tccgaagggg attattcggc ggtttataat    6900
cccggtggcc ccggcaatga tccagagaat ggtcccccaa attcgtaatc atgtcatagc    6960
tgtttcctgt gtgaaattgt tatccgctca caattccaca caacatacga gccggaagca    7020
taaagtgtaa agcctggggt gcctaatgag tgagctaact cacattaatt gcgttgcgct    7080
cactgcccgc tttccagtcg ggaaacctgt cgtgccagct gcattaatga atcggccaac    7140
gcgcggggag aggcggtttg cgtattgggc gct                                 7173
```

<210> SEQ ID NO 12
<211> LENGTH: 7029
<212> TYPE: DNA
<213> ORGANISM: Artificial Sequence
<220> FEATURE:
<223> OTHER INFORMATION: Synthetic construct

<400> SEQUENCE: 12

```
attgctgaag cggaatccct ggttaatgcc gccgccgatg ccaattgcat tctccaagtg      60
gggcacattg aacgcttcaa cccggcattt ttagagctaa ccaaaattct caaaacggaa     120
```

```
gagttattgg cgatcgaagc ccatcgcatg agtccctatt cccagcgggc caatgatgtc    180
tccgtggtat tggatttgat gatccatgac attgacctgt tgctggaatt ggtgggttcg    240
gaagtggtta aactgtccgc cagtggcagt cgggcttctg ggtcaggata tttggattat    300
gtcaccgcta cgttaggctt ctcctccggc attgtggcca ccctcaccgc cagtaaggtc    360
acccatcgta aaattcgttc catcgccgcc cactgcaaaa attccctcac cgaagcggat    420
tttctcaata cgaaattttt gatccatcgc caaaccaccg ctgattggag cgcggactat    480
ggccaggtat tgtatcgcca ggatggtcta atcgaaaagg tttacaccag taatattgaa    540
cctctccacg ctgaattaga acattttatt cattgtgtta ggggaggtga tcaaccctca    600
gtgggggggag aacaggccct caaggccctg aagttagcca gtttaattga agaaatggcc    660
ctggacagtc aggaatggca tggggggaa gttgtgacag aatatcaaga tgccaccctg    720
gccctcagtg cgagtgttta aatcaactta attaatgcaa ttattgcgag ttcaaactcg    780
ataactttgt gaaatattac tgttgaatta atctatgact attcaataca cccccctagc    840
cgatcgcctg ttggcctacc tcgccgccga tcgcctaaat ctcagcgcca agagtagttc    900
cctcaacacc agtattctgc tcagcagtga cctattcaat caggaagggg gaattgtaac    960
agccaactat ggctttgatg gttatatggt accatatggt gcactctcag tacaatctgc   1020
tctgatgccg catagttaag ccagtataca ctccgctatc gctacgtgac tgggtcatgg   1080
ctgcgccccg acaccgcca acaccgctg acgcgccctg acgggcttgt ctgctcccgg   1140
catccgctta cagacaagct gtgaccgtct ccgggagctg catgtgtcag aggttttcac   1200
cgtcatcacc gaaacgcgcg aggcagcaga tcaattcgcg cgcgaaggcg aagcggcatg   1260
catttacgtt gacaccatcg aatggtgcaa aacctttcgc ggtatggcat gatagcgccc   1320
ggaagagagt caattcaggg tggtgaatgt gaaaccagta acgttatacg atgtcgcaga   1380
gtatgccggt gtctcttatc agaccgtttc ccgcgtggtg aaccaggcca gccacgtttc   1440
tgcgaaaacg cgggaaaaag tggaagcggc gatggcggag ctgaattaca ttcccaaccg   1500
cgtggcacaa caactggcgg gcaaacagtc gttgctgatt ggcgttgcca cctccagtct   1560
ggccctgcac gcgccgtcgc aaattgtcgc ggcgattaaa tctcgcgccg atcaactggg   1620
tgccagcgtg gtggtgtcga tggtagaacg aagcggcgtc gaagcctgta aagcggcggt   1680
gcacaatctt ctcgcgcaac gcgtcagtgg gctgatcatt aactatccgc tggatgacca   1740
ggatgccatt gctgtggaag ctgcctgcac taatgttccg gcgttatttc ttgatgtctc   1800
tgaccagaca cccatcaaca gtattatttt ctcccatgaa gacggtacgc gactgggcgt   1860
ggagcatctg gtcgcattgg gtcaccagca atcgcgctg ttagcgggcc cattaagttc   1920
tgtctcggcg cgtctgcgtc tggctggctg cataaatat ctcactcgca atcaaattca   1980
gccgatagcg gaacgggaag gcgactggag tgccatgtcc ggttttcaac aaaccatgca   2040
aatgctgaat gagggcatcg ttcccactgc gatgctggtt gccaacgatc agatggcgct   2100
gggcgcaatg cgcgccatta ccgagtccgg gctgcgcgtt ggtgcggata tctcggtagt   2160
gggatacgac gataccgaag acagctcatg ttatatcccg ccgttaacca ccatcaaaca   2220
ggattttcgc ctgctgggc aaaccagcgt ggaccgcttg ctgcaactct ctcagggcca   2280
ggcggtgaag gcaatcagc tgttgcccgt ctcactggtg aaaagaaaaa ccaccctggc   2340
gcccaatacg caaaccgcct ctccccgcgc gttggccgat tcattaatgc agctggcacg   2400
acaggtttcc cgactggaaa gcgggcagtg agcgcaacgc aattaatgta agttagcgcg   2460
```

-continued

```
aattgatctg gtttgacagc ttatcatcga ctgcacggtg caccaatgct tctggcgtca    2520
ggcagccatc ggaagctgtg gtatggctgt gcaggtcgta aatcactgca taattcgtgt    2580
cgctcaaggc gcactcccgt tctggataat gttttttgcg ccgacatcat aacggttctg    2640
gcaaatattc tgaaatgagc tgttgacaat taatcatccg gctcgtataa tgtgtggaat    2700
tgtgagcgga taacaatttc acacaggaaa cagcgccgct gagaaaaagc gaagcggcac    2760
tgctctttaa caatttatca gacaatctgt gtgggcactc gaccggaatt atcgattaac    2820
tttattatta aaaattaaag aggtatatat taatgtatcg attaaataag gaggaataaa    2880
ccatggcgaa tggttctgca gtctctttga aatctggaag cttgaatacg caggaggata    2940
ctagttccag tcccctcct cggacgtttt tgcatcagct gcccgactgg agtcgcttgc    3000
tgaccgccat cacaacagtg tttgtcaaat ctaaacgacc ggacatgcat gatcggaaaa    3060
gcaagcgccc agatatgctc gtcgatagtt tcggactcga gtctactgtg caggacggcc    3120
tggtgttccg tcaatccttc agcatccgaa gctacgagat tggtacggac cgtaccgcta    3180
gcattgaaac gttgatgaac catctccaag aaaccagttt gaaccactgc aagagcacgg    3240
gcatcctgct ggatggtttt ggccgcacat tggaaatgtg caagcgagac ttgatctggg    3300
tggtcattaa aatgcagatc aaagttaatc gatacccggc ctggggagat accgttgaga    3360
tcaatacacg cttttcccgt ttgggcaaaa ttggcatggg tcgcgattgg ctgatctccg    3420
actgcaacac cggtgagatc ttggtccgtg caacgtctgc gtacgcgatg atgaatcaaa    3480
agacgcgtcg gttgagtaag ctgccgtatg aagttcacca agaaattgtt ccattgttcg    3540
ttgatagtcc cgttatcgag gattctgacc tcaaagtcca caagtttaaa gtcaagactg    3600
gcgattccat ccagaagggc ctgacgccag gttggaacga tctggatgtg aaccaacacg    3660
ttagcaacgt taagtatatc ggctggatct tggaaagtat gcctacgaa gtcctggaga    3720 cgcaggaact ctgcagtctc gctctggagt accgccgtga gtgtggccgt gattccgtgc    3780
tcgagtccgt cactgcgatg gaccctagca agtgggtgt tcgcagtcaa taccaacacc    3840
tcttgcggct cgaagatggg accgccattg tgaacggcgc gaccgaatgg cgccccaaaa    3900
atgccggcgc taacggggca attagtaccg ggaaaacctc caatggaaac agcgtcagct    3960
aatgatagga tccgagctca gatctaccag gttgtccttg gcgcagcgct tcccacgctg    4020
agagggtgta gcccgtcacg ggtaaccgat atcgtcgaca ggcctctaga cccgggctcg    4080
agctagcaag cttggccgga tccggccgga tccggagttt gtagaaacgc aaaaaggcca    4140
tccgtcagga tggccttctg cttaatttga tgcctggcag tttatggcgg gcgtcctgcc    4200
cgccaccctc cgggccgttg cttcgcaacg ttcaaatccg ctcccggcgg atttgtccta    4260
ctcaggagag cgttcaccga caaacaacag ataaaacgaa aggcccagtc tttcgactga    4320
gcctttcgtt ttatttgatg cctggcagtt ccctactctc gcatggggag accccacact    4380
accatcggcg ctacggcgtt tcacttctga gttcggcatg gggtcaggtg gaccaccgc    4440 gctactgccg ccaggcaaat tctgttttat tgagccgtta ccccacctac tagctaatcc    4500
catctgggca catccgatgg caagaggccc gaaggtcccc ctctttggtc ttgcgacgtt    4560
atgcggtatt agctaccgtt tccagtagtt atcccctcc atcaggcagt ttcccagaca    4620
ttactcaccc gtccgccact cgtcagcaaa gaagcaagct tagatcgacc tgcagggggg    4680 gggggggaaag ccacgttgtg tctcaaaatc tctgatgtta cattgcacaa gataaaaata    4740
tatcatcatg aacaataaaa ctgtctgctt acataaacag taatacaagg ggtgttatga    4800
gccatattca acgggaaacg tcttgctcga ggccgcgatt aaattccaac atggatgctg    4860
```

```
atttatatgg gtataaatgg gctcgcgata atgtcgggca atcaggtgcg acaatctatc   4920
gattgtatgg gaagcccgat gcgccagagt tgtttctgaa acatggcaaa ggtagcgttg   4980
ccaatgatgt tacagatgag atggtcagac taaactggct gacggaattt atgcctcttc   5040
cgaccatcaa gcatttatc cgtactcctg atgatgcatg ttactcacc actgcgatcc     5100
ccgggaaaac agcattccag gtattagaag aatatcctga ttcaggtgaa aatattgttg   5160
atgcgctggc agtgttcctg cgccggttgc attcgattcc tgtttgtaat tgtccttta    5220
acagcgatcg cgtatttcgt ctcgctcagg cgcaatacg aatgaataac ggtttggttg    5280
atgcgagtga ttttgatgac gagcgtaatg gctggcctgt tgaacaagtc tggaaagaaa   5340
tgcataagct tttgccattc tcaccggatt cagtcgtcac tcatggtgat ttctcacttg   5400
ataaccttat ttttgacgag gggaaattaa taggttgtat tgatgttgga cgagtcggaa   5460
tcgcagaccg ataccaggat cttgccatcc tatggaactg cctcggtgag ttttctcctt   5520
cattacagaa acggcttttt caaaaatatg gtattgataa tcctgatatg aataaattgc   5580
agtttcattt tgatgctcgat gagttttcct aatcagaatt ggttaattgg ttgtaacact  5640
ggcagagcat tacgctgact tgacgggacg gcggctttgt tgaataaatc gaacttttgc   5700
tgagttgaag atcagatca cgcatcttcc cgacaacgca gaccgttccg tggcaaagca    5760
aaagttcaaa atcaccaact ggtccaccta caacaaagct ctcatcaacc gtggctccct   5820
cactttctgg ctgatgatg gggcgattca ggcctggtat gagtcagcaa caccttcttc    5880
acgaggcaga cctcagcgcc ccccccccc tgcaggtcga tctggtaacc ccagcgcggt    5940
tgctaccaag tagtgacccg cttcgtgatg caaaatccgc tgacgatatt cgggcgatcg   6000
ctgctgaatg ccatcgagca gtaacgtggc gaattcggta ccggtatgga tggcaccgat   6060
gcggaatccc aacagattgc ctttgacaac aatgtggcct ggaataacct ggggatttg    6120
tccaccacca cccaacgggc ctacacttcg gctattagca cagacacagt gcagagtgtt   6180
tatggcgtta atctggaaaa aaacgataac attcccattg ttttttgcgtg gcccattttt   6240
cccaccaccc ttaatcccac agattttcag gtaatgctta acacgggga aattgtcacc   6300
ccggtgatcg cctctttgat tcccaacagt gaatacaacg aacggcaaac ggtagtaatt   6360
acgggcaatt ttggtaatcg tttaacccca ggcacggagg gagcgattta tcccgtttcc   6420
gtaggcacag tgttggacag tactcctttg gaaatggtgg gacccaacgg cccggtcagt   6480
gcggtgggta ttaccattga tagtctcaac ccctacgtgg ccggcaatgg tcccaaaatt   6540
gtcgccgcta agttagaccg cttcagtgac ctggggaag gggctcccct ctggttagcc    6600
accaatcaaa ataacagtgg cggggattta tatggagacc aagcccaatt tcgtttgcga   6660
atttacacca gcgccggttt ttcccccgat ggcattgcca gtttactacc cacagaattt   6720
gaacggtatt ttcaactcca agcggaagat attacgggac ggacagttat cctaacccaa   6780
actggtgttg attatgaaat tcccggcttt ggtctggtgc aggtgttggg gctggcggat   6840
ttggccgggg ttcaggacag ctatgacctg acttacatcg aagatcatga caactattac   6900
gacattatcc tcaaagggga cgaagccgca gttcgccaaa ttaagagggt tgctttgccc   6960
tccgaagggg attattcggc ggtttataat cccgtggcc ccggcaatga tccagagaat    7020
ggtcccccca                                                         7029
```

<210> SEQ ID NO 13  
<211> LENGTH: 6883  
<212> TYPE: DNA

<213> ORGANISM: Artificial Sequence
<220> FEATURE:
<223> OTHER INFORMATION: Synthetic construct

<400> SEQUENCE: 13

```
attgctgaag cggaatccct ggttaatgcc gccgccgatg ccaattgcat tctccaagtg      60
gggcacattg aacgcttcaa cccggcattt ttagagctaa ccaaaattct caaaacggaa     120
gagttattgg cgatcgaagc ccatcgcatg agtccctatt cccagcgggc caatgatgtc     180
tccgtggtat tggatttgat gatccatgac attgacctgt tgctggaatt ggtgggttcg     240
gaagtggtta aactgtccgc cagtggcagt cgggcttctg ggtcaggata tttggattat     300
gtcaccgcta cgttaggctt ctcctccggc attgtggcca ccctcaccgc cagtaaggtc     360
acccatcgta aaattcgttc catcgccgcc cactgcaaaa attccctcac cgaagcggat     420
tttctcaata cgaaattttt gatccatcgc caaaccaccg ctgattggag cgcggactat     480
ggccaggtat tgtatcgcca ggatggtcta atcgaaaagg tttacaccag taatattgaa     540
cctctccacg ctgaattaga acattttatt cattgtgtta gggaggtga tcaaccctca     600
gtgggggggag aacaggccct caaggccctg aagttagcca gtttaattga agaaatggcc     660
ctggacagtc aggaatggca tggggggaa gttgtgacga aatatcaaga tgccaccctg     720
gccctcagtg cgagtgttta aatcaactta attaatgcaa ttattgcgag ttcaaactcg     780
ataactttgt gaaatattac tgttgaatta atctatgact attcaataca ccccctagc     840
cgatcgcctg ttggcctacc tcgccgccga tcgcctaaat ctcagcgcca agagtagttc     900
cctcaacacc agtattctgc tcagcagtga cctattcaat caggaagggg gaattgtaac     960
agccaactat ggctttgatg gttatatggt accatatggt gcactctcag tacaatctgc    1020
tctgatgccg catagttaag ccagtataca ctccgctatc gctacgtgac tgggtcatgg    1080
ctgcgccccg acaccgcca acacccgctg acgcgccctg acgggcttgt ctgctcccgg    1140
catccgctta cagacaagct gtgaccgtct ccgggagctg catgtgtcag aggttttcac    1200
cgtcatcacc gaaacgcgcg aggcagcaga tcaattcgcg cgcgaaggcg aagcggcatg    1260
catttacgtt gacaccatcg aatggtgcaa aacctttcgc ggtatggcat gatagcgccc    1320
ggaagagagt caattcaggg tggtgaatgt gaaaccagta acgttatacg atgtcgcaga    1380
gtatgccggt gtctcttatc agaccgtttc ccgcgtggtg aaccaggcca gccacgtttc    1440
tgcgaaaacg cgggaaaaag tggaagcggc gatggcggag ctgaattaca ttcccaaccg    1500
cgtggcacaa caactggcgg gcaaacagtc gttgctgatt ggcgttgcca cctccagtct    1560
ggccctgcac gcgccgtcgc aaattgtcgc ggcgattaaa tctcgcgccg atcaactggg    1620
tgccagcgtg gtggtgtcga tggtagaacg aagcggcgtc gaagcctgta aagcggcggt    1680
gcacaatctt ctcgcgcaac gcgtcagtgg gctgatcatt aactatccgc tggatgacca    1740
ggatgccatt gctgtggaag ctgcctgcac taatgttccg gcgttatttc ttgatgtctc    1800
tgaccagaca cccatcaaca gtattatttt ctcccatgaa gacggtacgc gactgggcgt    1860
ggagcatctg gtcgcattgg gtcaccagca atcgcgctg ttagcgggcc cattaagttc    1920
tgtctcggcg cgtctgcgtc tggctggctg cataaatat ctcactcgca atcaaattca    1980
gccgatagcg gaacgggaag cgactggag tgccatgtcc ggttttcaac aaaccatgca    2040
aatgctgaat gagggcatcg ttcccactgc gatgctggtt gccaacgatc agatggcgct    2100
gggcgcaatg cgcgccatta ccgagtccgg gctgcgcgtt ggtgcggata tctcggtagt    2160
gggatacgac gataccgaag acagctcatg ttatatcccg ccgttaacca ccatcaaaca    2220
```

```
ggattttcgc ctgctggggc aaaccagcgt ggaccgcttg ctgcaactct ctcagggcca   2280
ggcggtgaag ggcaatcagc tgttgcccgt ctcactggtg aaaagaaaaa ccaccctggc   2340
gcccaatacg caaaccgcct ctccccgcgc gttggccgat tcattaatgc agctggcacg   2400
acaggtttcc cgactggaaa gcgggcagtg agcgcaacgc aattaatgta agttagcgcg   2460
aattgatctg gtttgacagc ttatcatcga ctgcacggtg caccaatgct tctggcgtca   2520
ggcagccatc ggaagctgtg gtatggctgt gcaggtcgta atcactgca taattcgtgt   2580 cgctcaaggc gcactcccgt tctggataat gttttttgcg ccgacatcat aacggttctg   2640
gcaaatattc tgaaatgagc tgttgacaat taatcatccg gctcgtataa tgtgtggaat   2700
tgtgagcgga taacaatttc acacaggaaa cagaccatgg cgaatggttc tgcagtctct   2760
ttgaaatctg gaagcttgaa tacgcaggag gatactagtt ccagtccccc tcctcggacg   2820
tttttgcatc agctgcccga ctggagtcgc ttgctgaccg ccatcacaac agtgtttgtc   2880
aaatctaaac gaccggacat gcatgatcgg aaaagcaagc gcccagatat gctcgtcgat   2940
agtttcggac tcgagtctac tgtgcaggac ggcctggtgt tccgtcaatc cttcagcatc   3000
cgaagctacg agattggtac ggaccgtacc gctagcattg aaacgttgat gaaccatctc   3060
caagaaacca gtttgaacca ctgcaagagc acgggcatcc tgctggatgg ttttggccgc   3120
acattggaaa tgtgcaagcg agacttgatc tgggtggtca ttaaaatgca gatcaaagtt   3180
aatcgatacc cggcctgggg agataccgtt gagatcaata cacgcttttc ccgtttgggc   3240
aaaattggca tgggtcgcga ttggctgatc tccgactgca caccggtga gatcttggtc   3300 cgtgcaacgt ctgcgtacgc gatgatgaat caaaagacgc gtcggttgag taagctgccg   3360
tatgaagttc accaagaaat tgttccattg ttcgttgata gtcccgttat cgaggattct   3420
gacctcaaag tccacaagtt taaagtcaag actggcgatt ccatccagaa gggcctgacg   3480
ccaggttgga acgatctgga tgtgaaccaa cacgttagca cgttaagta tatcggctgg   3540 atcttggaaa gtatgcctac ggaagtcctg gagacgcagg aactctgcag tctcgctctg   3600
gagtaccgcc gtgagtgtgg ccgtgattcc gtgctcgagt ccgtcactgc gatggaccct   3660
agcaaagtgg gtgttcgcag tcaataccaa cacctcttgc ggctcgaaga tgggaccgcc   3720
attgtgaacg cgcgaccga atggcgcccc aaaaatgccg gcgctaacgg ggcaattagt   3780
accgggaaaa cctccaatgg aaacagcgtc agctaatgat aggatccgag ctcagatcta   3840
ccaggttgtc cttggcgcag cgcttcccac gctgagaggg tgtagcccgt cacgggtaac   3900
cgatatcgtc gacaggcctc tagacccggg ctcgagctag caagcttggc cggatccggc   3960
cggatccgga gtttgtagaa acgcaaaaag gccatccgtc aggatggcct tctgcttaat   4020
ttgatgcctg gcagtttatg gcgggcgtcc tgcccgccac cctccgggcc gttgcttcgc   4080
aacgttcaaa tccgctcccg gcggatttgt cctactcagg agagcgttca ccgacaaaca   4140
acagataaaa cgaaaggccc agtctttcga ctgagccttt cgttttattt gatgcctggc   4200
agttccctac tctcgcatgg ggagacccca cactaccatc ggcgctacgg cgtttcactt   4260
ctgagttcgg catggggtca ggtgggacca ccgcgctact gccgccaggc aaattctgtt   4320
ttattgagcc gttaccccac ctactagcta atcccatctg gcacatccg atggcaagag   4380 gcccgaaggt ccccctcttt ggtcttgcga cgttatgcgg tattagctac cgtttccagt   4440
agttatcccc ctccatcagg cagtttccca gacattactc acccgtccgc cactcgtcag   4500
caaagaagca agcttagatc gacctgcagg ggggggggg aaagccacgt tgtgtctcaa   4560
```

```
aatctctgat gttacattgc acaagataaa aatatatcat catgaacaat aaaactgtct    4620
gcttacataa acagtaatac aagggggtgtt atgagccata ttcaacggga aacgtcttgc    4680
tcgaggccgc gattaaattc caacatggat gctgatttat atgggtataa atgggctcgc    4740
gataatgtcg ggcaatcagg tgcgacaatc tatcgattgt atgggaagcc cgatgcgcca    4800
gagttgtttc tgaaacatgg caaaggtagc gttgccaatg atgttacaga tgagatggtc    4860
agactaaact ggctgacgga atttatgcct cttccgacca tcaagcattt tatccgtact    4920
cctgatgatg catggttact caccactgcg atccccggga aaacagcatt ccaggtatta    4980
gaagaatatc ctgattcagg tgaaaatatt gttgatgcgc tggcagtgtt cctgcgccgg    5040
ttgcattcga ttcctgtttg taattgtcct tttaacagcg atcgcgtatt tcgtctcgct    5100
caggcgcaat cacgaatgaa taacggtttg gttgatgcga gtgattttga tgacgagcgt    5160
aatggctggc ctgttgaaca gtctggaaa gaaatgcata agcttttgcc attctcaccg    5220
gattcagtcg tcactcatgg tgatttctca cttgataacc ttattttga cgaggggaaa    5280
ttaataggtt gtattgatgt tggacgagtc ggaatcgcag accgatacca ggatcttgcc    5340
atcctatgga actgcctcgg tgagttttct ccttcattac agaaacggct ttttcaaaaa    5400
tatggtattg ataatcctga tatgaataaa ttgcagtttc atttgatgct cgatgagttt    5460
ttctaatcag aattggttaa ttggttgtaa cactggcaga gcattacgct gacttgacgg    5520
gacggcggct ttgttgaata atcgaacttt tgctgagtt gaaggatcag atcacgcatc    5580
ttcccgacaa cgcagaccgt tccgtggcaa agcaaaagtt caaaatcacc aactggtcca    5640
cctacaacaa agctctcatc aaccgtggct ccctcacttt ctggctggat gatggggcga    5700
ttcaggcctg gtatgagtca gcaacacctt cttcacgagg cagacctcag cgcccccccc    5760
cccctgcagg tcgatctggt aaccccagcg cggttgctac caagtagtga cccgcttcgt    5820
gatgcaaaat ccgctgacga tattcgggcg atcgctgctg aatgccatcg agcagtaacg    5880
tggcgaattc ggtaccggta tggatggcac cgatgcggaa tcccaacaga ttgcctttga    5940
caacaatgtg gcctggaata acctgggggga tttgtccacc accacccaac gggcctacac    6000
ttcggctatt agcacagaca cagtgcagag tgttatgcc gttaatctgg aaaaaaacga    6060
taacattccc attgttttttg cgtggcccat ttttcccacc acccttaatc ccacagattt    6120
tcaggtaatg cttaacacgg gggaaattgt caccccggtg atcgcctctt tgattcccaa    6180
cagtgaatac aacgaacggc aaacggtagt aattacgggc aattttggta atcgtttaac    6240
cccaggcacg gagggagcga tttatcccgt ttccgtaggc acagtgttgg acagtactcc    6300
tttggaaatg gtgggaccca acggcccggt cagtgcggtg ggtattacca ttgatagtct    6360
caaccccctac gtggccggca atggtcccaa aattgtcgcc gctaagttag accgcttcag    6420
tgacctgggg gaaggggctc ccctctggtt agccaccaat caaaataaca gtggcgggga    6480
tttatatgga gaccaagccc aatttcgttt gcgaatttac accagcgccg gttttttcccc    6540
cgatggcatt gccagtttac tacccacaga atttgaacgg tattttcaac tccaagcgga    6600
agatattacg ggacggacag ttatcctaac ccaaactggt gttgattatg aaattcccgg    6660
ctttggtctg gtgcaggtgt tggggctggc ggatttggcc ggggtcagg acagctatga    6720
cctgacttac atcgaagatc atgacaacta ttacgacatt atcctcaaag gggacgaagc    6780
cgcagttcgc caaattaaga gggttgcttt gccctccgaa ggggattatt cggcggttta    6840
taatcccggt ggccccggca atgatccaga gaatggtccc cca    6883
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
accctggccc tcagtgcgag                                            20

<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
tgcttctttg ctgacgagtg g                                          21

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
gtgactggaa ccgccctcg                                             19

<210> SEQ ID NO 17
<211> LENGTH: 44
<212> TYPE: DNA
<213> ORGANISM: Artificial Sequence
<220> FEATURE:
<223> OTHER INFORMATION: Primer

<400> SEQUENCE: 17
ccatcgagca gtaacgtggc cgatagtgac gctaaaccag gctg                 44

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
cgagtggcgg acgggtgagt ctacgagggc gtgcagaagc                      40

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
caccaagttg ccttcaccga c                                          21

<210> SEQ ID NO 20
<211> LENGTH: 44
<212> TYPE: DNA
<213> ORGANISM: Artificial Sequence
<220> FEATURE:
<223> OTHER INFORMATION: Primer
```

<400> SEQUENCE: 20

```
cagcctggtt tagcgtcact atcggccacg ttactgctcg atgg          44
```

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21

```
gcttctgcac gccctcgtag actcacccgt ccgccactcg              40
```

<210> SEQ ID NO 22
<211> LENGTH: 2840
<212> TYPE: DNA
<213> ORGANISM: Artificial Sequence
<220> FEATURE:
<223> OTHER INFORMATION: Synthetic construct

<400> SEQUENCE: 22

```
gtgactggaa ccgccctcgc gcaacccgc gccattacgc cccacgaaca gcagcttttg    60
gccaaactga aaagctatcg cgatatccaa agcttgtcgc aaatttgggg acgtgctgcc   120
agtcaatttg gatcgatgcc ggctttggtt gcaccccatg ccaaaccagc gatcaccctc   180
agttatcaag aattggcgat tcagatccaa gcgtttgcag ccggactgct cgcgctggga   240
gtgcctacct ccacagccga tgactttccg cctcgcttgg cgcagtttgc ggataacagc   300
ccccgctggt tgattgctga ccaaggcacg ttgctggcag gggctgccaa tgcggtgcgc   360
ggcgcccaag ctgaagtatc ggagctgctc tacgtcttag aggacagcgg ttcgatcggc   420
ttgattgtcg aagacgcggc gctgctgaag aaactacagc ctggtttagc gtcactatcg   480
gccacgttac tgctcgatgg cattcagcag cgatcgcccg aatatcgtca gcggattttg   540
catcacgaag cgggtcacta cttggtagca accgcgctgg ggttaccaga tccgtcgatc   600
atatcgtcaa ttattacctc cacggggaga gcctgagcaa actggcctca ggcatttgag   660
aagcacacgg tcacactgct tccggtagtc aataaaccgg taaaccagca atagacataa   720
gcggctattt aacgaccctg ccctgaaccg acgaccgggt cgaatttgct ttcgaatttc   780
tgccattcat ccgcttatta tcacttattc aggcgtagca ccaggcgttt aagggcacca   840
ataactgcct aaaaaaatt acgccccgcc ctgccactca tcgcagtact gttgtaattc    900
attaagcatt ctgccgacat ggaagccatc acaaacggca tgatgaacct gaatcgccag   960
cggcatcagc accttgtcgc cttgcgtata atatttgccc atggtgaaaa cggggggcgaa  1020
gaagttgtcc atattggcca cgtttaaatc aaaactggtg aaactcaccc agggattggc   1080
tgagacgaaa aacatattct caataaaccc tttagggaaa taggccaggt tttcaccgta   1140
acacgccaca tcttgcgaat atatgtgtag aaactgccgg aaatcgtcgt ggtattcact   1200
ccagagcgat gaaaacgttt cagtttgctc atggaaaacg gtgtaacaag ggtgaacact   1260
atcccatatc accagctcac cgtctttcat tgccatacgg aattccggat gagcattcat   1320
caggcgggca agaatgtgaa taaaggccgg ataaaacttg tgcttatttt tctttacggt   1380
ctttaaaaag gccgtaatat ccagctgaac ggtctggtta taggtacatt gagcaactga   1440
ctgaaatgcc tcaaaatgtt ctttacgatg ccattgggat atatcaacgg tggtatatcc   1500
agtgattttt ttctccattt tagcttcctt agctcctgaa atctcgata actcaaaaaa    1560
tacgcccggt agtgatctta tttcattatg gtgaaagttg gaacctctta cgtgccgatc   1620
```

```
aacgtctcat tttcgccaaa agttggccca gggcttcccg gtatcaacag ggacaccagg    1680
atttatttat tctgcgaagt gatcttccgt cacaggtatt tattcgaaga cgaaagggcc    1740
tcgtgatacg cctattttta taggttaatg tcatgataat aatggtttct tagacgtcag    1800
gtggcacttt tcggggaaat gtgcgcggaa cccctatttg tttatttttc taaatacatt    1860
caaatatgta tccgctcatg agacaataac cctgataaat gcttcaataa tattgaaaaa    1920
ggaagagtat gagtattcaa catttccgtg tcgcccttat tcccttttt gcggcatttt     1980 gccttcctgt ttttgctcac ccagaaacgc tggtgaaagt aaaagatgct gaagatcagt    2040
tgggtgcacg agtgggttac atcgaactgg atctcaacag cggtaagatc cttgagagtt    2100
ttcgccccga agaacgtttt ccaatgatga gcacttttaa agttctgcta tgtggcgcgg    2160
tattatcccg tgtgacggat ctaagcttgc ttctttgctg acgagtggcg gacgggtgag    2220
tctacgaggg cgtgcagaag cagtttcgcg agcaaccggc gaagaaacgt cgcttgatcg    2280
ataccttctt tggcttgagt caacgctatg ttttggcacg cgccgctgg caaggactgg     2340 atttgctggc actgaaccaa tccccagccc agcgcctcgc tgagggtgtc cggatgttgg    2400
cgctagcacc gttgcataag ctgggcgatc gcctcgtcta cggcaaagta cgagaagcca    2460
cgggtggccg aattcggcag gtgatcagtg gcggtggctc actggcactg cacctcgata    2520
ccttcttcga aattgttggt gttgatttgc tggtgggtta tggcttgaca gaaacctcac    2580
cagtgctgac ggggcgacgg ccttggcaca acctacgggg ttcggccggt cagccgattc    2640
caggtacggc gattcggatc gtcgatcctg aaacgaagga aaaccgaccc agtggcgatc    2700
gcggcttggt gctggcgaaa gggccgcaaa tcatgcaggg ctacttcaat aaacccgagg    2760
cgaccgcgaa agcgatcgat gccgaaggtt ggtttgacac cggcgactta ggctacatcg    2820
tcggtgaagg caacttggtg                                                2840

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ctcgagcccc cgtgctatga ctagc                                          25

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
ctcgagcccg gaacgttttt tgtacccc                                       28

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
caattggtca cacgggataa taccgcgcc                                      29
```

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26

```
caattggtcg atcatatcgt caattattac ctccac                               36
```

<210> SEQ ID NO 27
<211> LENGTH: 7224
<212> TYPE: DNA
<213> ORGANISM: Artificial Sequence
<220> FEATURE:
<223> OTHER INFORMATION: Synthetic construct

<400> SEQUENCE: 27

```
cccccgtgct atgactagcg gcgatcgcca taccggccac gaccatttgc attggatccc     60
caacggcggc cacaacttcc atggcattga gatgcgggga atgatgttct agactctgac    120
gcaccaaagc caattttttgt tgatggttgc aatggggatg actactgttc actttgcccc   180
cagcgtcaat gcctagacct agcagtaccc ccagggctgt ggtagtgccc ccaccacgc     240
attcgcttag cactaagtaa ctttcggcat gttcctgggc taactgtgcg ccccactgca    300
aaccctgctg aaaagatgc tccaccaggg ccaacggtaa cgcttgccct gtggaaagac    360
agcgggcggg ttgtccgtct agattgatga ctggcaccgc tggggggaatg ggtaaaccag   420
agttaaataa ataaaccgga gtatggaggg catccaccaa cgctttggtg atgaacactg    480
gggaaacccc agaaatgagg ggaggtaagg gataggttgc ccctgccgta gttcccttga    540
ttaaaaattc cgcatcggcg atcgccgtca attttcgatc agcggggggtt ttacccgccg   600
cagaaatgcc cggaattaaa ccagtttccg taaagcccaa cacacagaca aacaccggtg    660
gacagtggcc atggcgctca atccaggata aagcttggtc agactgggta taaactgtca    720
acatatttct gcaagagtgg gcccaattgg gaaaatcaac ctcaaatcca ttggaatagc    780
ctttttttcaa ccgtaaaaat ccaacttttct ctcttccctt cttccttcca tctgattatg  840
gttacgccaa ttaactacca ttccatccat gcctggcgg atatctgggc tatcaccgga    900
gaaaattttg ccgatattgt ggccctcaac gatcgccata gtcatccccc cgtaacttta    960
acctatgccc aattggtcac acgggataat accgcgccac atagcagaac tttaaaagtg   1020
ctcatcattg gaaacgttc ttcggggcga aaactctcaa ggatcttacc gctgttgaga    1080
tccagttcga tgtaacccac tcgtgcaccc aactgatctt cagcatcttt tactttcacc    1140
agcgtttctg ggtgagcaaa acaggaagg caaaatgccg caaaaaaggg aataagggcg    1200
acacggaaat gttgaatact catactcttc cttttttcaat attattgaag catttatcag    1260
ggttattgtc tcatgagcgg atacatattt gaatgtattt agaaaaataa acaaataggg   1320
gttccgcgca catttccccg aaaagtgcca cctgacgtct aagaaaccat tattatcatg   1380
acattaacct ataaaaatag gcgtatcacg aggccctttc gtcttcgaat aaatacctgt    1440
gacggaagat cacttcgcag aataaataaa tcctggtgtc cctgttgata ccggaagcc     1500
ctgggccaac tttttggcgaa aatgagacgt tgatcggcac gtaagaggtt ccaactttca   1560
ccataatgaa ataagatcac taccgggcgt atttttttgag ttatcgagat tttcaggagc   1620
taaggaagct aaaatggaga aaaaaatcac tggatatacc accgttgata tatcccaatg    1680
gcatcgtaaa gaacattttg aggcatttca gtcagttgct caatgtacct ataaccagac    1740
```

```
cgttcagctg gatattacgg ccttttaaa gaccgtaaag aaaaataagc acaagtttta    1800
tccggccttt attcacattc ttgcccgcct gatgaatgct catccggaat tccgtatggc    1860
aatgaaagac ggtgagctgg tgatatggga tagtgttcac ccttgttaca ccgttttcca    1920
tgagcaaact gaaacgtttt catcgctctg gagtgaatac cacgacgatt tccggcagtt    1980
tctacacata tattcgcaag atgtggcgtg ttacggtgaa aacctggcct atttccctaa    2040
agggtttatt gagaatatgt ttttcgtctc agccaatccc tgggtgagtt tcaccagttt    2100
tgatttaaac gtggccaata tggacaactt cttcgccccc gttttcacca tgggcaaata    2160
ttatacgcaa ggcgacaagg tgctgatgcc gctggcgatt caggttcatc atgccgtttg    2220
tgatggcttc catgtcggca gaatgcttaa tgaattacaa cagtactgcg atgagtggca    2280
gggcggggcg taattttttt aaggcagtta ttggtgccct aaacgcctg gtgctacgcc    2340 tgaataagtg ataataagcg gatgaatggc agaaattcga aagcaaattc gacccggtcg    2400
tcggttcagg gcagggtcgt taaatagccg cttatgtcta ttgctggttt accggtttat    2460
tgactaccgg aagcagtgtg accgtgtgct tctcaaatgc ctgaggccag tttgctcagg    2520
ctctccccgt ggaggtaata attgacgata tgatcgacca attgcgggaa gaaattacag    2580
cttttgccgc tggcctacag agtttaggag ttaccccca tcaacacctg gccatttttcg    2640 ccgacaacag cccccggtgg tttatcgccg atcaaggcag tatgttggct ggagccgtca    2700
acgccgtccg ttctgcccaa gcagagcgcc aggaattact ctacatccta aagacagca    2760 acagccgtac tttaatcgca gaaaatcggc aaacccctaag caaattggcc ctagatggcg    2820
aaaccattga cctgaaacta atcatcctcc tcaccgatga agaagtggca gaggacagcg    2880
ccattcccca atataacttt gcccaggtca tggccctagg ggccggcaaa atccccactc    2940
ccgttccccg ccaggaagaa gatttagcca ccctgatcta cacctccggc accacaggac    3000
aacccaaagg ggtgatgctc agccacggta atttattgca ccaagtacgg gaattggatt    3060
cggtgattat tccccgcccc ggcgatcagg tgttgagcat tttgccctgt tggcactccc    3120
tagaaagaag cgccgaatat tttcttcttt cccggggctg cacgatgaac tacaccagca    3180
ttcgccattt caaggggggat gtgaaggaca ttaaacccca tcacattgtc ggtgtgcccc    3240
ggctgtggga atccctctac gaaggggtac aaaaaacgtt ccgggctaag ggcgaattct    3300
gcagatatcc atcacactgg cggccgctcg agcatgcatc tagagggccc aattcgccct    3360
atagtgagtc gtattacaat tcactggccg tcgttttaca acgtcgtgac tgggaaaacc    3420
ctggcgttac ccaacttaat cgccttgcag cacatccccc tttcgccagc tggcgtaata    3480
gcgaagaggc ccgcaccgat cgccttccc aacagttgcg cagcctgaat ggcgaatgga    3540
cgcgccctgt agcggcgcat taagcgcggc gggtgtggtg gttacgcgca gcgtgaccgc    3600
tacacttgcc agcgccctag cgcccgctcc tttcgctttc ttcccttcct ttctcgccac    3660
gttcgccggc tttccccgtc aagctctaaa tcggggctc ctttagggt tccgatttag    3720 tgctttacgg cacctcgacc ccaaaaaact tgattagggt gatggttcac gtagtgggcc    3780
atcgccctga tagacggttt ttcgcccttt gacgttggag tccacgttct ttaatagtgg    3840
actcttgttc caaactggaa caacactcaa ccctatctcg gtctattctt ttgatttata    3900
agggattttg ccgatttcgg cctattggtt aaaaaatgag ctgatttaac aaaaatttaa    3960
cgcgaatttt aacaaaattc agggcgcaag ggctgctaaa ggaagcggaa cacgtagaaa    4020
gccagtccgc agaaacggtg ctgaccccgg atgaatgtca gctactgggc tatctggaca    4080
```

-continued

```
agggaaaacg caagcgcaaa gagaaagcag gtagcttgca gtgggcttac atggcgatag    4140
ctagactggg cggttttatg gacagcaagc gaaccggaat tgccagctgg ggcgccctct    4200
ggtaaggttg ggaagccctg caaagtaaac tggatggctt tcttgccgcc aaggatctga    4260
tggcgcaggg gatcaagatc tgatcaagag acaggatgag gatcgtttcg catgattgaa    4320
caagatggat tgcacgcagg ttctccggcc gcttgggtgg agaggctatt cggctatgac    4380
tgggcacaac agacaatcgg ctgctctgat gccgccgtgt tccggctgtc agcgcagggg    4440
cgcccggttc tttttgtcaa gaccgacctg tccggtgccc tgaatgaact gcaggacgag    4500
gcagcgcggc tatcgtggct ggccacgacg ggcgttcctt gcgcagctgt gctcgacgtt    4560
gtcactgaag cgggaaggga ctggctgcta ttgggcgaag tgccggggca ggatctcctg    4620
tcatcccacc ttgctcctgc cgagaaagta tccatcatgg ctgatgcaat gcggcggctg    4680
catacgcttg atccggctac ctgcccattc gaccaccaag cgaaacatcg catcgagcga    4740
gcacgtactc ggatggaagc cggtcttgtc gatcaggatg atctggacga agagcatcag    4800
gggctcgcgc cagccgaact gttcgccagg ctcaaggcgc gcatgcccga cggcgaggat    4860
ctcgtcgtga cccatggcga tgcctgcttg ccgaatatca tggtggaaaa tggccgcttt    4920
tctggattca tcgactgtgg ccggctgggt gtggcggacc gctatcagga catagcgttg    4980
gctacccgtg atattgctga agagcttggc ggcgaatggg ctgaccgctt cctcgtgctt    5040
tacggtatcg ccgctcccga ttcgcagcgc atcgccttct atcgccttct tgacgagttc    5100
ttctgaattg aaaaaggaag agtatgagta ttcaacattt ccgtgtcgcc cttattccct    5160
tttttgcggc attttgcctt cctgtttttg ctcacccaga aacgctggtg aaagtaaaag    5220
atgctgaaga tcagttgggt gcacgagtgg gttacatcga actggatctc aacagcggta    5280
agatccttga gagttttcgc cccgaagaac gttttccaat gatgagcact tttaaagttc    5340
tgctatgtgg cgcggtatta cccgtattg acgccgggca agagcaactc ggtcgccgca    5400
tacactattc tcagaatgac ttggttgagt actcaccagt cacagaaaag catcttacgg    5460
atggcatgac agtaagagaa ttatgcagtg ctgccataac catgagtgat aacactgcgg    5520
ccaacttact tctgacaacg atcggaggac cgaaggagct aaccgctttt ttgcacaaca    5580
tgggggatca tgtaactcgc cttgatcgtt gggaaccgga gctgaatgaa gccataccaa    5640
acgacgagcg tgacaccacg atgcctgtag caatggcaac aacgttgcgc aaactattaa    5700
ctggcgaact acttactcta gcttcccggc aacaattaat agactggatg gaggcggata    5760
aagttgcagg accacttctg cgctcggccc ttccggctgg ctggtttatt gctgataaat    5820
ctggagccgg tgagcgtggg tctcgcggta tcattgcagc actggggcca gatggtaagc    5880
cctcccgtat cgtagttatc tacacgacgg ggagtcaggc aactatggat gaacgaaata    5940
gacagatcgc tgagataggt gcctcactga ttaagcattg gtaactgtca gaccaagttt    6000
actcatatat actttagatt gatttaaaac ttcatttta atttaaaagg atctaggtga    6060
agatcctttt tgataatctc atgaccaaaa tcccttaacg tgagttttcg ttccactgag    6120
cgtcagaccc cgtagaaaag atcaaaggat cttcttgaga tcctttttt ctgcgcgtaa    6180
tctgctgctt gcaaacaaaa aaaccaccgc taccagcggt ggtttgtttg ccggatcaag    6240
agctaccaac tctttttccg aaggtaactg gcttcagcag agcgcagata ccaaatactg    6300
ttcttctagt gtagccgtag ttaggccacc acttcaagaa ctctgtagca ccgcctacat    6360
acctcgctct gctaatcctg ttaccagtgg ctgctgccag tggcgataag tcgtgtctta    6420
ccgggttgga ctcaagacga tagttaccgg ataaggcgca gcggtcgggc tgaacggggg    6480
```

```
gttcgtgcac acagcccagc ttggagcgaa cgacctacac cgaactgaga tacctacagc    6540
gtgagctatg agaaagcgcc acgcttcccg aagggagaaa ggcggacagg tatccggtaa    6600
gcggcagggt cggaacagga gagcgcacga gggagcttcc aggggaaac gcctggtatc     6660 tttatagtcc tgtcgggttt cgccacctct gacttgagcg tcgattttg tgatgctcgt     6720 cagggggcg gagcctatgg aaaaacgcca gcaacgcggc ctttttacgg ttcctggcct     6780
tttgctggcc ttttgctcac atgttctttc ctgcgttatc ccctgattct gtggataacc    6840
gtattaccgc ctttgagtga gctgataccg ctcgccgcag ccgaacgacc gagcgcagcg    6900
agtcagtgag cgaggaagcg gaagagcgcc caatacgcaa accgcctctc cccgcgcgtt    6960
ggccgattca ttaatgcagc tggcacgaca ggtttcccga ctggaaagcg ggcagtgagc    7020
gcaacgcaat taatgtgagt tagctcactc attaggcacc ccaggcttta cactttatgc    7080
ttccggctcg tatgttgtgt ggaattgtga gcggataaca atttcacaca ggaaacagct    7140
atgaccatga ttacgccaag cttggtaccg agctcggatc cactagtaac ggccgccagt    7200
gtgctggaat tcgcccttct cgag                                            7224

<210> SEQ ID NO 28
<211> LENGTH: 79
<212> TYPE: DNA
<213> ORGANISM: Artificial Sequence
<220> FEATURE:
<223> OTHER INFORMATION: Synthetic construct

<400> SEQUENCE: 28
gatccgctgt tgacccaaca gcatgagtcg ttatccaagg ggagcttcgg ctccctttt     60 tcatgcgcgg atgcggtga                                                  79

<210> SEQ ID NO 29
<211> LENGTH: 1503
<212> TYPE: DNA
<213> ORGANISM: Artificial Sequence
<220> FEATURE:
<223> OTHER INFORMATION: Synthetic construct

<400> SEQUENCE: 29
ggatccacta gtcctgaggt gttgacaatt aatcatccgg ctcgtataat gtgtggaatt    60
gtgagcggat aacaatttca cagg aaac agaccatggc cgtcgcactg caaccagctc    120
aagaagtcgc aactaagaaa aagcctgcaa tcaaacagcg gcgcgtggtg gttaccggca    180
tgggtgtggt gactccctc gggcatgaac cggatgtgtt ttacaacaat ctcctggatg     240
gcgtgagcgg cattagtgag atcgagaatt ttgactcgac gcagtttccc actcgcattg    300
ccggcgaaat caagagtttc agcaccgacg gctgggtcgc gcccaaattg agcaaacgga    360
tggataaatt gatgctgtat ctgctcaccg caggcaagaa agcgctggcc gatgcgggca    420
tcacggatga tgtgatgaaa gagctggata acgcaaatg tggagttctg attggcagtg    480
gcatgggcgg catgaagctg ttctacgatg cgctcgaagc cctgaagatt tcgtatcgaa    540
agatgaaccc attctgtgtg ccttttgcga ccacgaatat gggtagcgcc atgctggcta    600
tggatttggg gtggatgggg ccgaattata gtatttccac cgcgtgcgca acctcgaact    660
tctgcatctt gaacgcggct aaccacatta tccgtggtga agcagacatg atgctctgcg    720
gcggctccga tgcggtcatt atccctatcg gtttgggcgg cttttgttgct tgccgcgcct    780 tgagccaacg caataacgac ccaaccaagg catcgcgccc gtgggacagc aatcgcgatg    840
```

```
gcttcgtcat gggcgaggga gccggggtgc tgctgttgga ggagctggaa cacgcgaaaa    900
agcgaggcgc gacaatctat gctgagttct tgggagggtc ctttacatgc gatgcctacc    960
acatgacgga gcctcaccca gagggcgcag gcgtgatctt gtgtatcgag aaggcaatgg   1020
ctcaggcagg agtctctcgc gaggatgtta actacattaa tgctcacgca acgtccacgc   1080
cggctggtga catcaaggaa taccaagctc tcgcccattg tttcggccag aactcggagc   1140
tgcgggtcaa tagtacaaag tccatgatcg gtcatctgct gggtgctgcc ggtgcgtcg    1200
aagctgtgac agtcattcaa gccatccgca ccggctggat tcaccctaat ctgaacctgg   1260
aagacccgga caaggccgtt gacgcaaaat tcctcgtcgg accggagaaa gaacgtctca   1320
acgttaaagt cggattgagc aatagtttcg gttttggtgg ccataactct agtatcctgt   1380
ttgcacccta taattgataa tagatctgat ccgctgttga cccaacagca tgagtcgtta   1440
tccaaggga gcttcggctc cctttttca tgcgcggatg cggtgagagc tcacgtgtct    1500
aga                                                                1503

<210> SEQ ID NO 30
<211> LENGTH: 1224
<212> TYPE: DNA
<213> ORGANISM: Artificial Sequence
<220> FEATURE:
<223> OTHER INFORMATION: Synthetic construct

<400> SEQUENCE: 30
ggatccacta gtcctgaggt gttgacaatt aatcatccgg ctcgtataat gtgtggaatt    60
gtgagcggat aacaatttca cacaggaaac agaccatggc aagccgtgtt gttggtaaag   120
gttgtaaact cgttggatgt ggtagtgccg tcccgaagtt ggaggtgagt aacgacgacc   180
tcagtaagat cgtggatact tccgatgaat ggatttctgt tcggacggga atccgcaacc   240
ggcgggtgat tactggtaag gataagatga cggggctggc ggtcgaggca gcccagaaag   300
ccctggaaat ggctgaagtc gatgctgacg atgtggactt gctcctgttg tgcacctcca   360
ccccagatga tctctttgga agtgcgccgc aaatccaggc ggcactcggc tgcaaaggaa   420
accctctggc atttgatatt acagccgctt gtagcggctt cgttctgggt ctggtgagtg   480
cttcctgcta tatccgcggc ggcggggttca agaacgtcct ggttatcggc gcggacgcac   540
tgagccgcta cgtcgattgg actgaccgcg gcacatgcat tctctttggt gacgccgctg   600
gcgctgtgtt ggtccaggcg tgtgagagcg aggacgacgg cgtcttcggg tttgatctgc   660
atagcgatgg agagggttat cgccacctgc atactgggat caaggcgaac gaggagttcg   720
ggacgaacgg ttccgttgtg gattttccgc ccaagcgcag cagctactct tccatccaaa   780
tgaatgggaa agaagtgttc cgtttcgcct gccgcgtcgt gccccagtct attgagatcg   840
cactcgagaa cgcgggcctc acacgttcta gcattgattg gctgctgctc caccaagcaa   900
accaacgaat cttggatgcc gtcgcaacgc gtctggaaat tccgcagac cgcgtgatta    960
gtaacttggc taattacggc aatacttctg ccgccagcat tccgttggca ctggatgaag   1020
ccgtgcgcag cggtaaggtc aaacccggtc agactatcgc aacttcgggg tttggagcag   1080
gcttgacatg gggcagcgcg atcattcgct ggaattaatg atagatctga tccgctgttg   1140
acccaacagc atgagtcgtt atccaagggg agcttcggct cccttttttc atgcgcggat   1200
gcggtgagag ctcacgtgtc taga                                          1224

<210> SEQ ID NO 31
<211> LENGTH: 1613
```

<212> TYPE: DNA
<213> ORGANISM: Artificial Sequence
<220> FEATURE:
<223> OTHER INFORMATION: Synthetic construct

<400> SEQUENCE: 31

| | | | | | |
|---|---|---|---|---|---|
| tgttgacaat | taatcatccg | gctcgtataa | tgtgtggaat | tgtgagcgga | taacaatttc | 60 |
| acacaggaaa | cagcgccgct | gagaaaaagc | gaagcggcac | tgctctttaa | caatttatca | 120 |
| gacaatctgt | gtgggcactc | gaccggaatt | atcgattaac | tttattatta | aaaattaaag | 180 |
| aggtatatat | taatgtatcg | attaaataag | gaggaataaa | ccatggccgt | cgcactgcaa | 240 |
| ccagctcaag | aagtcgcaac | taagaaaaag | cctgcaatca | aacagcggcg | cgtggtggtt | 300 |
| accggcatgg | gtgtggtgac | tcccctcggg | catgaaccgg | atgtgtttta | caacaatctc | 360 |
| ctggatggcg | tgagcggcat | tagtgagatc | gagaattttg | actcgacgca | gtttcccact | 420 |
| cgcattgccg | gcgaaatcaa | gagtttcagc | accgacggct | gggtcgcgcc | caaattgagc | 480 |
| aaacggatga | taaaattgat | gctgtatctg | ctcaccgcag | gcaagaaagc | gctggccgat | 540 |
| gcgggcatca | cggatgatgt | gatgaaagag | ctggataaac | gcaaatgtgg | agttctgatt | 600 |
| ggcagtggca | tgggcggcat | gaagctgttc | tacgatgcgc | tcgaagccct | gaagatttcg | 660 |
| tatcgaaaga | tgaacccatt | ctgtgtgcct | tttgcgacca | cgaatatggg | tagcgccatg | 720 |
| ctggctatgg | atttggggtg | gatggggccg | aattatagta | tttccaccgc | gtgcgcaacc | 780 |
| tcgaacttct | gcatcttgaa | cgcggctaac | cacattatcc | gtggtgaagc | agacatgatg | 840 |
| ctctgcggcg | gctccgatgc | ggtcattatc | cctatcggtt | tgggcggctt | tgttgcttgc | 900 |
| cgcgccttga | gccaacgcaa | taacgaccca | accaaggcat | cgcgcccgtg | ggacagcaat | 960 |
| cgcgatggct | tcgtcatggg | cgagggagcc | ggggtgctgc | tgttggagga | gctggaacac | 1020 |
| gcgaaaaagc | gaggcgcgac | aatctatgct | gagttcttgg | gagggtcctt | tacatgcgat | 1080 |
| gcctaccaca | tgacggagcc | tcacccagag | ggcgcaggcg | tgatcttgtg | tatcgagaag | 1140 |
| gcaatggctc | aggcaggagt | ctctcgcgag | gatgttaact | acattaatgc | tcacgcaacg | 1200 |
| tccacgccgg | ctggtgacat | caaggaatac | caagctctcg | cccattgttt | cggccagaac | 1260 |
| tcggagctgc | gggtcaatag | tacaaagtcc | atgatcggtc | atctgctggg | tgctgccggt | 1320 |
| ggcgtcgaag | ctgtgacagt | cattcaagcc | atccgcaccg | gctggattca | ccctaatctg | 1380 |
| aacctggaag | acccggacaa | ggccgttgac | gcaaaattcc | tcgtcggacc | ggagaaagaa | 1440 |
| cgtctcaacg | ttaaagtcgg | attgagcaat | agtttcggtt | ttggtggcca | taactctagt | 1500 |
| atcctgtttg | caccctataa | ttgataatag | atctgatccg | ctgttgaccc | aacagcatga | 1560 |
| gtcgttatcc | aagggagct | tcggctccct | ttttcatgc | gcggatgcgg | tga | 1613 |

<210> SEQ ID NO 32
<211> LENGTH: 2698
<212> TYPE: DNA
<213> ORGANISM: Artificial Sequence
<220> FEATURE:
<223> OTHER INFORMATION: Synthetic construct

<400> SEQUENCE: 32

| | | | | | |
|---|---|---|---|---|---|
| cctgaggtgt | tgacaattaa | tcatccggct | cgtataatgt | gtggaattgt | gagcggataa | 60 |
| caatttcaca | caggaaacag | cgccgctgag | aaaagcgaa | gcggcactgc | tctttaacaa | 120 |
| tttatcagac | aatctgtgtg | ggcactcgac | cggaattatc | gattaacttt | attattaaaa | 180 |
| attaaagagg | tatatattaa | tgtatcgatt | aaataaggag | gaataaacca | tggccgtcgc | 240 |

```
actgcaacca gctcaagaag tcgcaactaa gaaaaagcct gcaatcaaac agcggcgcgt         300
ggtggttacc ggcatgggtg tggtgactcc cctcgggcat gaaccggatg tgttttacaa         360
caatctcctg gatggcgtga gcggcattag tgagatcgag aattttgact cgacgcagtt         420
tcccactcgc attgccggcg aaatcaagag tttcagcacc gacggctggg tcgcgcccaa         480
attgagcaaa cggatggata aattgatgct gtatctgctc accgcaggca agaaagcgct         540
ggccgatgcg ggcatcacgg atgatgtgat gaaagagctg gataaacgca aatgtggagt         600
tctgattggc agtggcatgg gcggcatgaa gctgttctac gatgcgctcg aagccctgaa         660
gatttcgtat cgaaagatga acccattctg tgtgcctttt gcgaccacga atatgggtag         720
cgccatgctg gctatggatt tggggtggat ggggccgaat tatagtattt ccaccgcgtg         780
cgcaacctcg aacttctgca tcttgaacgc ggctaaccac attatccgtg gtgaagcaga         840
catgatgctc tgcggcggct ccgatgcggt cattatccct atcggtttgg gcggctttgt         900
tgcttgccgc gccttgagcc aacgcaataa cgacccaacc aaggcatcgc gcccgtggga         960
cagcaatcgc gatggcttcg tcatgggcga gggagccggg gtgctgctgt ggaggagct         1020 ggaacacgcg aaaaagcgag gcgcgacaat ctatgctgag ttcttgggag ggtcctttac         1080
atgcgatgcc taccacatga cggagcctca cccagagggc gcaggcgtga tcttgtgtat         1140
cgagaaggca atggctcagg caggagtctc tcgcgaggat gttaactaca ttaatgctca         1200
cgcaacgtcc acgccggctg gtgacatcaa ggaataccaa gctctcgccc attgtttcgg         1260
ccagaactcg gagctgcggg tcaatagtac aaagtccatg atcggtcatc tgctgggtgc         1320
tgccggtggc gtcgaagctg tgacagtcat tcaagccatc cgcaccggct ggattcaccc         1380
taatctgaac ctggaagacc cggacaaggc cgttgacgca aaattcctcg tcggaccgga         1440
gaaagaacgt ctcaacgtta aagtcggatt gagcaatagt ttcggttttg gtggccataa         1500
ctctagtatc ctgtttgcac cctataattg ataatagatc ctgtcgttaa ctgctttgtt         1560
ggtactacct gacttcaccc tcttttaaga tggcaagccg tgttgttggt aaaggttgta         1620
aactcgttgg atgtggtagt gccgtcccga agttggaggt gagtaacgac gacctcagta         1680
agatcgtgga tacttccgat gaatggattt ctgttcggac gggaatccgc aaccggcggg         1740
tgattactgg taaggataag atgacggggc tggcggtcga ggcagcccag aaagccctgg         1800
aaatggctga agtcgatgct gacgatgtgg acttgctcct gttgtgcacc tccaccccag         1860
atgatctctt tggaagtgcg ccgcaaatcc aggcggcact cggctgcaaa ggaaaccctc         1920
tggcatttga tattacagcc gcttgtagcg gcttcgttct gggtctggtg agtgcttcct         1980
gctatatccg cggcggcggg ttcaagaacg tcctggttat cggcgcggac gcactgagcc         2040
gctacgtcga ttggactgac cgcggcacat gcattctctt tggtgacgcc gctggcgctg         2100
tgttggtcca ggcgtgtgag agcgaggacg acggcgtctt cgggtttgat ctgcatagcg         2160
atggagaggg ttatcgccac ctgcatactg ggatcaaggc gaacgaggag ttcgggacga         2220
acggttccgt tgtggatttt ccgcccaagc gcagcagcta ctcttccatc caaatgaatg         2280
ggaaagaagt gttccgtttc gcctgccgcg tcgtgcccca gtctattgag atcgcactcg         2340
agaacgcggg cctcacacgt tctagcattg attggctgct gctccaccaa gcaaaccaac         2400
gaatcttgga tgccgtcgca acgcgtctgg aaattcccgc agaccgcgtg attagtaact         2460
tggctaatta cggcaatact tctgccgcca gcattccgtt ggcactggat gaagccgtgc         2520
gcagcggtaa ggtcaaaccc ggtcagacta tcgcaacttc ggggtttgga gcaggcttga         2580
catggggcag cgcgatcatt cgctggaatt aatgatagat ctgatccgct gttgacccaa         2640
```
cagcatgagt cgttatccaa ggggagcttc ggctcccttt tttcatgcgc ggatgcgg    2698

<210> SEQ ID NO 33
<211> LENGTH: 89
<212> TYPE: DNA
<213> ORGANISM: Artificial Sequence
<220> FEATURE:
<223> OTHER INFORMATION: Synthetic construct

<400> SEQUENCE: 33
gtacgggatc cctgtcgtta actgctttgt tggtactacc tgacttcacc ctcttttaag    60
atggcaagcc gtgttgttgg taaaggttg                                      89

<210> SEQ ID NO 34
<211> LENGTH: 29
<212> TYPE: DNA
<213> ORGANISM: Artificial Sequence
<220> FEATURE:
<223> OTHER INFORMATION: Synthetic construct

<400> SEQUENCE: 34
cacgtgagct ctcaccgcat ccgcgcatg                                      29

<210> SEQ ID NO 35
<211> LENGTH: 1252
<212> TYPE: DNA
<213> ORGANISM: Artificial Sequence
<220> FEATURE:
<223> OTHER INFORMATION: Synthetic construct

<400> SEQUENCE: 35
tcatgaagtt ccttgtcgtc gccgtctcag cacttgcaac tgcatctgct ttcacaacca    60
gtcctgcctc tttcaccact gtcagcagtc cttcggtgaa caatgtgttc ggacaggagg   120
gaaatgctca caggaacagg agagctacca ttgtcatgga tggagctaac ggaagtgcag   180
tcagtttgaa aagtgggtca ttgaatacgc aggaggacac aagttcgtcg ccaccgcccc   240
gtacattcct tcaccaactc cctgattgga gcagattgct cactgccatc acaaccgttt   300
ttgttaaaag taagcgtccg gatatgcatg atcgtaagtc gaaaaggccg acatgctcg    360 tggatagttt cgggttggag agtaccgttc aggatggact cgtgttccgt caaagctttt   420
cgatccgttc atatgagatt ggaactgatc gtacggcttc cattgagact ttgatgaacc   480
atcttcagga gacttccctc aaccattgta agagtacagg aattttgttg gatggattcg   540
gacgcacact cgaaatgtgt aagcgcgatt tgatttgggt cgtcattaaa atgcagatca   600
aggttaatag atacccggcc tggggcgata cagtagaaat caatactagg ttcagcagac   660
ttggtaagat cggcatgggt cgagattggc tcattagcga ctgcaatacc ggtgagatcc   720
tcgtcagggc aaccagcgcc tacgccatga tgaatcagaa gacccgaaga ctctcgaagc   780
ttccgtacga ggtccaccaa gagattgtcc ccctttttgt cgactccccc gtaattgaag   840
attcggatct caaggtccac aaattcaaag ttaaaacggg tgacagcatc cagaagggac   900
ttactcctgg ttggaacgac ctcgatgtga accaacatgt ttcgaacgtg aaatatatcg   960
gctggattct tgagagtatg ccaaccgagg tacttgagac gcaggaattg tgctcgttgg  1020
cattggagta tcgtcgtgag tgtgggcgag actcagtcct cgaaagtgta acagcaatgg  1080
acccaagcaa agttggtgtt cgttcacagt atcaacacct cctccgtctc gaggatggaa  1140
cagccattgt gaacggggcc acagagtgga ggccaaagaa cgctggcgct aacggagcta  1200
tctccacagg aaagaccagc aatggtaact ctgtgagtta atgataggat cc        1252

<210> SEQ ID NO 36
<211> LENGTH: 412
<212> TYPE: PRT
<213> ORGANISM: Artificial Sequence
<220> FEATURE:
<223> OTHER INFORMATION: Synthetic construct

<400> SEQUENCE: 36

Met Lys Phe Leu Val Val Ala Val Ser Ala Leu Ala Thr Ala Ser Ala
1               5                   10                  15

Phe Thr Thr Ser Pro Ala Ser Phe Thr Thr Val Ser Ser Pro Ser Val
            20                  25                  30

Asn Asn Val Phe Gly Gln Glu Gly Asn Ala His Arg Asn Arg Arg Ala
        35                  40                  45

Thr Ile Val Met Asp Gly Ala Asn Gly Ser Ala Val Ser Leu Lys Ser
    50                  55                  60

Gly Ser Leu Asn Thr Gln Glu Asp Thr Ser Ser Pro Pro Pro Pro Arg
65                  70                  75                  80

Thr Phe Leu His Gln Leu Pro Asp Trp Ser Arg Leu Leu Thr Ala Ile
                85                  90                  95

Thr Thr Val Phe Val Lys Ser Lys Arg Pro Asp Met His Asp Arg Lys
            100                 105                 110

Ser Lys Arg Pro Asp Met Leu Val Asp Ser Phe Gly Leu Glu Ser Thr
        115                 120                 125

Val Gln Asp Gly Leu Val Phe Arg Gln Ser Phe Ser Ile Arg Ser Tyr
    130                 135                 140

Glu Ile Gly Thr Asp Arg Thr Ala Ser Ile Glu Thr Leu Met Asn His
145                 150                 155                 160

Leu Gln Glu Thr Ser Leu Asn His Cys Lys Ser Thr Gly Ile Leu Leu
                165                 170                 175

Asp Gly Phe Gly Arg Thr Leu Glu Met Cys Lys Arg Asp Leu Ile Trp
            180                 185                 190

Val Val Ile Lys Met Gln Ile Lys Val Asn Arg Tyr Pro Ala Trp Gly
        195                 200                 205

Asp Thr Val Glu Ile Asn Thr Arg Phe Ser Arg Leu Gly Lys Ile Gly
    210                 215                 220

Met Gly Arg Asp Trp Leu Ile Ser Asp Cys Asn Thr Gly Glu Ile Leu
225                 230                 235                 240

Val Arg Ala Thr Ser Ala Tyr Ala Met Met Asn Gln Lys Thr Arg Arg
                245                 250                 255

Leu Ser Lys Leu Pro Tyr Glu Val His Gln Glu Ile Val Pro Leu Phe
            260                 265                 270

Val Asp Ser Pro Val Ile Glu Asp Ser Asp Leu Lys Val His Lys Phe
        275                 280                 285

Lys Val Lys Thr Gly Asp Ser Ile Gln Lys Gly Leu Thr Pro Gly Trp
    290                 295                 300

Asn Asp Leu Asp Val Asn Gln His Val Ser Asn Val Lys Tyr Ile Gly
305                 310                 315                 320

Trp Ile Leu Glu Ser Met Pro Thr Glu Val Leu Glu Thr Gln Glu Leu
                325                 330                 335

Cys Ser Leu Ala Leu Glu Tyr Arg Arg Glu Cys Gly Arg Asp Ser Val
            340                 345                 350

Leu Glu Ser Val Thr Ala Met Asp Pro Ser Lys Val Gly Val Arg Ser

```
                355                 360                 365
Gln Tyr Gln His Leu Leu Arg Leu Glu Asp Gly Thr Ala Ile Val Asn
            370                 375                 380

Gly Ala Thr Glu Trp Arg Pro Lys Asn Ala Gly Ala Asn Gly Ala Ile
385                 390                 395                 400

Ser Thr Gly Lys Thr Ser Asn Gly Asn Ser Val Ser
                405                 410
```

```
<210> SEQ ID NO 37
<211> LENGTH: 26
<212> TYPE: DNA
<213> ORGANISM: Artificial Sequence
<220> FEATURE:
<223> OTHER INFORMATION: Primer

<400> SEQUENCE: 37
caggatccgg ggaggtgtgg tgtagt                                          26

<210> SEQ ID NO 38
<211> LENGTH: 43
<212> TYPE: DNA
<213> ORGANISM: Artificial Sequence
<220> FEATURE:
<223> OTHER INFORMATION: Primer

<400> SEQUENCE: 38
taggatccag tggtgcccat ggtactttgt taggggagga tag                       43

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
caggatcctc actctgtcgc gctgttg                                         27

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
catctagaga ggattgattt ccgagtc                                         27

<210> SEQ ID NO 41
<211> LENGTH: 573
<212> TYPE: DNA
<213> ORGANISM: Artificial Sequence
<220> FEATURE:
<223> OTHER INFORMATION: Synthetic construct

<400> SEQUENCE: 41
atgggcacca ctctcgacga cacggcttac cgctaccgca ccagtgtgcc ggggacgcc      60 gaggccatcg aggcactgga tggtccttc accaccgaca ccgtcttccg cgtcaccgcc    120
accggggacg gcttcaccct gcgggaggtg ccggtggacc cgcccctgac caaggtgttc   180
cccgacgacg agtcggacga cgagtcggac gacggggagg acggcgaccc ggactcccgg   240
acgttcgtcg cgtacgggga cgacggcgac ctggcggggct tcgtggtcgt ctcgtactcc   300
```

```
ggctggaacc gccggctgac cgtcgaggac atcgaggtcg ccccggagca ccggggggcac    360 ggggtcgggc gcgcgctgat ggggctcgcg acggagttcg cccgcgagcg gggtgccggg    420
cacctctggc tggaggtcac caacgtcaac gcaccggcga tccacgcgta ccggcggatg    480
gggttcaccc tctgcggcct ggacaccgcc ctgtacgacg caccgcctc ggacggcgag    540 caggcgctct acatgtccat gccctgcccc taa                                 573

<210> SEQ ID NO 42
<211> LENGTH: 1198
<212> TYPE: DNA
<213> ORGANISM: Artificial Sequence
<220> FEATURE:
<223> OTHER INFORMATION: Synthetic construct

<400> SEQUENCE: 42
ccatggccgc tatgctcgcc tctaagcagg gcgccttcat gggccgcagc tcctttgccc     60
ccgcccccaa gggcgtcgcc agccgcggct ccctgcaggt ggtggccggc gccaacggca    120
gcgcggtgag cctgaagtcg ggttccctca acactcagga ggacacctcg tcctcgcccc    180
cgccgcgcac gttcctgcac cagctgccgg actggtcccg cctgctgacg gctattacga    240
ccgtgttcgt gaagtcgaag cgccccgaca tgcacgaccg caagagcaag cggcctgata    300
tgctggtgga cagctttggc ctggagtcca cggtgcagga cggcctcgtg ttccggcaaa    360
gcttcagcat ccgcagctac gagatcggca cggaccgcac cgcgtcgatc gagacgctca    420
tgaaccacct ccaggagacg tcgctcaacc actgcaagtc caccggtatc ctgctggacg    480
gctttggccg cacctggag atgtgcaagc gggatctgat ctgggtggtg atcaagatgc    540
agatcaaggt gaaccgctat cccgcctggg gtgacaccgt cgagattaac cccgcttct    600 cgcgcctggg caagatcggc atggggcgcg actggctgat ctcggactgc aacactggcg    660
agatcctggt ccgggccacg tcggcctacg ccatgatgaa ccagaagact cggcggctga    720
gcaagctgcc ttacgaggtg catcaggaga tcgtgccgct cttcgtggac agccccgtga    780
tcgaggacag cgatctgaag gtgcacaagt tcaaggtcaa gaccggcgac agcatccaga    840
agggcctgac tcccggctgg aacgacctgg acgtgaacca gcacgtctcg aacgtgaagt    900
acatcggctg gattctggag tcgatgccca ccgaggtgct ggagacgcag gagctgtgct    960
ccctggcgct ggagtatcgc cgcgagtgcg gccgcgactc cgtgctggag tccgtcaccg   1020
cgatggaccc gtcgaaggtg ggtgtccgca gccagtacca acacctgctg cgcctcgagg   1080
acggcaccgc cattgtgaac ggcgcgacgg agtggcggcc gaagaacgcg ggcgctaacg   1140
gcgccatctc cacgggcaag acctccaacg gcaactcggt gagctaatga taggatcc    1198

<210> SEQ ID NO 43
<211> LENGTH: 394
<212> TYPE: PRT
<213> ORGANISM: Artificial Sequence
<220> FEATURE:
<223> OTHER INFORMATION: Synthetic construct

<400> SEQUENCE: 43

Met Ala Ala Met Leu Ala Ser Lys Gln Gly Ala Phe Met Gly Arg Ser
  1               5                  10                  15

Ser Phe Ala Pro Ala Pro Lys Gly Val Ala Ser Arg Gly Ser Leu Gln
                 20                  25                  30

Val Val Ala Gly Ala Asn Gly Ser Ala Val Ser Leu Lys Ser Gly Ser
         35                  40                  45
```

```
Leu Asn Thr Gln Glu Asp Thr Ser Ser Ser Pro Pro Pro Arg Thr Phe
 50                  55                  60

Leu His Gln Leu Pro Asp Trp Ser Arg Leu Leu Thr Ala Ile Thr Thr
 65              70                  75                      80

Val Phe Val Lys Ser Lys Arg Pro Asp Met His Asp Arg Lys Ser Lys
                 85                  90                  95

Arg Pro Asp Met Leu Val Asp Ser Phe Gly Leu Glu Ser Thr Val Gln
            100                 105                 110

Asp Gly Leu Val Phe Arg Gln Ser Phe Ser Ile Arg Ser Tyr Glu Ile
        115                 120                 125

Gly Thr Asp Arg Thr Ala Ser Ile Glu Thr Leu Met Asn His Leu Gln
130                 135                 140

Glu Thr Ser Leu Asn His Cys Lys Ser Thr Gly Ile Leu Leu Asp Gly
145                 150                 155                 160

Phe Gly Arg Thr Leu Glu Met Cys Lys Arg Asp Leu Ile Trp Val Val
                165                 170                 175

Ile Lys Met Gln Ile Lys Val Asn Arg Tyr Pro Ala Trp Gly Asp Thr
            180                 185                 190

Val Glu Ile Asn Thr Arg Phe Ser Arg Leu Gly Lys Ile Gly Met Gly
        195                 200                 205

Arg Asp Trp Leu Ile Ser Asp Cys Asn Thr Gly Glu Ile Leu Val Arg
210                 215                 220

Ala Thr Ser Ala Tyr Ala Met Met Asn Gln Lys Thr Arg Arg Leu Ser
225                 230                 235                 240

Lys Leu Pro Tyr Glu Val His Gln Glu Ile Val Pro Leu Phe Val Asp
                245                 250                 255

Ser Pro Val Ile Glu Asp Ser Asp Leu Lys Val His Lys Phe Lys Val
            260                 265                 270

Lys Thr Gly Asp Ser Ile Gln Lys Gly Leu Thr Pro Gly Trp Asn Asp
        275                 280                 285

Leu Asp Val Asn Gln His Val Ser Asn Val Lys Tyr Ile Gly Trp Ile
290                 295                 300

Leu Glu Ser Met Pro Thr Glu Val Leu Glu Thr Gln Glu Leu Cys Ser
305                 310                 315                 320

Leu Ala Leu Glu Tyr Arg Arg Glu Cys Gly Arg Asp Ser Val Leu Glu
                325                 330                 335

Ser Val Thr Ala Met Asp Pro Ser Lys Val Gly Val Arg Ser Gln Tyr
            340                 345                 350

Gln His Leu Leu Arg Leu Glu Asp Gly Thr Ala Ile Val Asn Gly Ala
        355                 360                 365

Thr Glu Trp Arg Pro Lys Asn Ala Gly Ala Asn Gly Ala Ile Ser Thr
370                 375                 380

Gly Lys Thr Ser Asn Gly Asn Ser Val Ser
385                 390
```

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
ggtggaaaat gcctatgtgt taacg    25

```
<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
cgtaggcagt gtgcaaccag gagcc                                              25

<210> SEQ ID NO 46
<211> LENGTH: 3418
<212> TYPE: DNA
<213> ORGANISM: Artificial Sequence
<220> FEATURE:
<223> OTHER INFORMATION: Synthetic construct

<400> SEQUENCE: 46
ggtggaaaat gcctatgtgt taacggatct acaaaccagc accaaactct attacgaacc        60
ccacggtttc cactctcccc aactgcaaga cttggggccc attgatgtgg ttttaacccc       120
cgtcattggc atcaatatcc tcggattcct gccggtgctc aatggccaga aaaccaccct       180
ggagctttgt cgcactgtcc atccccaggc gatcgtcccc acctctggag ccgcagaatt       240
gaactatagc ggtttactaa ctaaagtttt acgtttagac ggcgatctca gtcaatttcg       300
ccagtcccta attgacgaag ggatacaagc ttccctatgg aaccccagg tgggagtgcc        360 cctcaatgtg ccccaatcca ccgttggcta ggttggaatg ttcaaatcac tgtgcggtgt       420
gatgcttgat aaatacagtg agccagggaa aactgcaaaa aagtgtataa agtaggttta       480
acttgaatca aaatcctttc tccgcagtca tagccaggag taggaagatt accagcgaag       540
caagttgtct tcccctagct ttgggcgggc aaacccttg cagtattgcc aacgtcaaaa        600
aatcaccata gccgaatgac ctacaccatc aacgctgacc aagtccatca gattgtccat       660
aatcttcacc acgatccctt tgaagtgttg ggctgccatc ccctcggagc tttatgcttg       720
taaaccgttt tgtgaaaaaa ttttaaaat aaaaagggg acctctaggg tccccaatta        780
attagtaata taatctatta aaggtcattc aaaaggtcat ccaccggatc agcttagtaa       840
agccctcgct agattttaat gcggatgttg cgattacttc gccaactatt gcgataacaa       900
gaaaaagcca gcctttcatg atatatctcc caatttgtgt agggcttatt atgcacgctt       960
aaaaataata aaagcagact tgacctgata gtttggctgt gagcaattat gtgcttagtg      1020
catctaacgc ttgagttaag ccgcgccgcg aagcggcgtc ggcttgaacg aattgttaga      1080
cattatttgc cgactacctt ggtgatctcg cctttcacgt agtggacaaa ttcttccaac      1140
tgatctgcgc gcgaggccaa gcgatcttct tcttgtccaa gataagcctg tctagcttca      1200
agtatgacgg gctgatactg ggccggcagg cgctccattg cccagtcggc agcgacatcc      1260
ttcggcgcga ttttgccggt tactgcgctg taccaaatgc gggacaacgt aagcactaca      1320
tttcgctcat cgccagccca gtcggcggc gagttccata gcgttaaggt ttcatttagc       1380
gcctcaaata gatcctgttc aggaaccgga tcaaagagtt cctccgccgc tggacctacc      1440
aaggcaacgc tatgttctct tgcttttgtc agcaagatag ccagatcaat gtcgatcgtg      1500
gctggctcga agatacctgc aagaatgtca ttgcgctgcc attctccaaa ttgcagttcg      1560
cgcttagctg gataacgcca cggaatgatg tcgtcgtgca acaatggt gacttctaca        1620 gcgcggagaa tctcgctctc tccagggga gccgaagttt ccaaaggtc gttgatcaaa        1680 gctcgccgcg ttgtttcatc aagccttacg gtcaccgtaa ccagcaaatc aatatcactg      1740
```

```
tgtggcttca ggccgccatc cactgcggag ccgtacaaat gtacggccag caacgtcggt    1800
tcgagatggc gctcgatgac gccaactacc tctgatagtt gagtcgatac ttcggcgatc    1860
accgcttccc tcatgatgtt taactttgtt ttagggcgac tgccctgctg cgtaacatcg    1920
ttgctgctcc ataacatcaa acatcgaccc acggcgtaac gcgcttgctg cttggatgcc    1980
cgaccgaggc atagactgta ccccaaaaaa acagtcataa caagccatga aaaccgccac    2040
tgcgccgtta ccaccgctgc gttcggtcaa ggttctggac cagttgcgtg agcgcatacg    2100
ctacttgcat tacagcttac gaaccgaaca ggcttatgtc cactgggttc gtgccttcat    2160
ccgtttccac ggtgtgcgtc acccggcaac cttgggcagc agcgaagtcg aggcatttct    2220
gtcctggctg gcgaacgagc gcaaggtttc ggtctccacg catcgtcagg cattggcggc    2280
cttgctgttc ttctacggca aggtgctgtg cacggatctg ccctggcttc aggagatcgg    2340
aagacctcgg ccgtcgcggc gcttgccggt ggtgctgacc ccggatgaag tggttcgcat    2400
cctcggtttt ctggaaggcg agcatcgttt gttcgcccag cttctgtatg aacgggcat    2460 gcggatcagt gagggtttgc aactgcgggt caaggatctg gatttcgatc acggcacgat    2520
catcgtgcgg gagggcaagg gctccaagga tcgggcctgg cacccagcct gcgcgagcag    2580
gggaattgat ccggtggatg accttttgaa tgacctttaa tagattatat tactaattaa    2640
ttggggaccc tagaggtccc cttttttatt ttaaaaattt tttcacaaaa cggtttacaa    2700
gcataaagct tcggggacca cggcaaggtc aatcaatggg tcattcgtgc ctatttaccc    2760
acggctgaag cggtaacggt gttgcttccc accgatcgcc gggaagtgat tatgaccacg    2820
gtccaccatc ccaactttt tgaatgcgtg ttggagttgg aagaaccgaa gaattatcaa     2880
ttaagaatta ccgaaaatgg ccacgaaagg gtaatttatg accccctatgg ttttaaaact    2940 cccaaactga cggattttga cctccatgtg tttggggaag gcaaccacca ccgtatttac    3000
gaaaaactcg gtgctcacct gatgacggtg gatggagtta aaggggttta ttttgctgtg    3060
tgggccccca atgcccgcaa cgtttccatt tgggggatt tcaacaactg ggacggcaga     3120
ttgcaccaaa tgcggaaacg caacaacatg gtgtgggaat tatttatccc tgagttgggg    3180
gtgggcactt cttataagta tgagattaaa aactgggaag gcacatcta cgaaaagact     3240 gaccectacg gttttttacca agaagtacgc cccaaaaccg cttccattgt ggcagacttg    3300
gacggttacc aatggcacga cgaagattgg ttggaagcta ggcgcaccag cgatcccctg    3360
agcaaacccg tttccgttta cgaactccat ttaggctcct ggttgcacac tgcctacg     3418
```